United States Patent
Burckhardt

(10) Patent No.: US 8,252,859 B2
(45) Date of Patent: Aug. 28, 2012

(54) ALDIMINES AND COMPOSITIONS COMPRISING ALDIMINE

(75) Inventor: Urs Burckhardt, Zurich (CH)

(73) Assignee: Sika Technology AG, Baar (CH)

(*) Notice: Subject to any disclaimer, the term of this patent is extended or adjusted under 35 U.S.C. 154(b) by 19 days.

(21) Appl. No.: 12/451,955

(22) PCT Filed: Jul. 16, 2008

(86) PCT No.: PCT/EP2008/059267
§ 371 (c)(1),
(2), (4) Date: Dec. 9, 2009

(87) PCT Pub. No.: WO2009/010522
PCT Pub. Date: Jan. 22, 2009

(65) Prior Publication Data
US 2010/0101455 A1    Apr. 29, 2010

(30) Foreign Application Priority Data
Jul. 16, 2007 (EP) .................................. 07112503

(51) Int. Cl.
*C08K 5/41* (2006.01)
*C07C 275/00* (2006.01)
(52) U.S. Cl. ......... 524/173; 524/237; 564/248; 564/278
(58) Field of Classification Search .................. 524/173, 524/237; 564/248, 278
See application file for complete search history.

(56) References Cited

U.S. PATENT DOCUMENTS

| | | | |
|---|---|---|---|
| 1,824,676 A | 9/1931 | Mannich | |
| 3,849,156 A | 11/1974 | Marlin et al. | |
| 3,862,879 A | 1/1975 | Barron et al. | |
| 4,224,417 A | 9/1980 | Hajek et al. | |
| 4,515,986 A | 5/1985 | Bernhagen et al. | |
| 4,853,454 A | 8/1989 | Merger et al. | |
| 5,168,110 A | 12/1992 | Van Den Elshout et al. | |
| 5,306,605 A | 4/1994 | Odenwalder et al. | |
| 6,136,942 A * | 10/2000 | Pfenninger et al. | 528/73 |
| 7,597,931 B2 | 10/2009 | Jones et al. | |
| 7,629,433 B2 | 12/2009 | Burckhardt | |
| 2005/0282989 A1 | 12/2005 | Rosthauser | |
| 2006/0149025 A1 | 7/2006 | Burckhardt | |
| 2007/0051832 A1 | 3/2007 | Jones et al. | |
| 2007/0066721 A1 | 3/2007 | Kramer et al. | |
| 2007/0105983 A1 | 5/2007 | Kramer et al. | |
| 2010/0190014 A1 * | 7/2010 | Burckhardt | 428/423.1 |

FOREIGN PATENT DOCUMENTS

| | | |
|---|---|---|
| DE | 42 12 795 A1 | 10/1993 |
| DE | 10 2005 042 380 A1 | 3/2007 |
| EP | 0 254 177 A2 | 1/1988 |
| EP | 1 384 709 A1 | 1/2004 |
| EP | 1 772 447 A1 | 4/2007 |
| EP | 1 775 284 A1 | 4/2007 |
| NL | 9000370 A | 9/1991 |
| WO | WO 00/39178 A1 | 7/2000 |
| WO | WO 2004/013088 A1 | 2/2004 |
| WO | WO 2004/055092 A1 | 7/2004 |
| WO | WO 2005/007720 A1 | 1/2005 |
| WO | WO 2007/036571 A1 | 4/2007 |

OTHER PUBLICATIONS

"Methoden der organischen Chemie," Houben-Weyl, Methods of Organic Chemistry, vol. XI/2, p. 73 (w/ translation).
Brown et al., "Modular synthesis of multidentate ligands with variable N-donors: applications to tri- and tetracopper(I) complexes," *Dalton Trans.*, 2007, pp. 3035-3042.
International Search Report issued in International Application No. PCT/EP2008/059267 on Sep. 19, 2008.
Jun. 9, 2011 Office Action issued in Russian Application No. 2010105241/04(007394) with English-language translation.
Johnson et al., "The Chemistry of Hindered Systems. Synthesis and Properties of Tetramethylazacycloheptanes and Related Acyclic Amines," *J. Org. Chem.*, vol. 40, No. 19, 1975, pp. 2710-2720.
Jan. 26, 2009 International Search Report issued in International Application No. PCT/EP2008/061400.
May 4, 2010 International Preliminary Report on Patentability issued in International Application No. PCT/EP2008/061400.

* cited by examiner

Primary Examiner — Ling Choi
Assistant Examiner — John Uselding
(74) Attorney, Agent, or Firm — Oliff & Berridge, PLC

(57) ABSTRACT

Aldimines of formula (I) that are particularly suitable as latent hardeners in curable compositions, particularly compositions having one or two-component isocyanate groups. Due to the presence of the reactive group, they can be converted to compounds of formulas (X) and (XII) having aldimine groups. The aldimines, or the aldimine compounds, can be used primarily in adhesive and sealant materials, but also in coatings, and can be produced easily from readily available source materials, and have good thermal stability. The tertiary amino group thereof has a surprisingly low alkalinity and can in some cases have a catalytic effect in chemical reaction systems.

26 Claims, No Drawings

ALDIMINES AND COMPOSITIONS COMPRISING ALDIMINE

TECHNICAL FIELD

The invention relates to the field of the aldimines.

STATE OF THE ART

Aldimines are condensation products formed from primary amines and aldehydes, and constitute a substance class which has been known for some time. On contact with water, aldimines can be hydrolyzed to the corresponding amines and aldehydes. Owing to this property, they can be used as a protected form of amines, or of aldehydes. For example, aldimines are used in polyurethane chemistry, where they serve as moisture-activable crosslinkers, known as "blocked amines" or "latent hardeners", for one- or two-component compositions having isocyanate groups.

The advantages of the use of aldimines as latent hardeners in systems having isocyanate groups are especially that the formation of undesired gas bubbles can be avoided, since the curing reaction via the blocked amine—in contrast to the direct reaction of isocyanates with moisture—does not proceed with release of carbon dioxide ($CO_2$), and that higher curing rates and/or longer open times can be achieved. The use of aldimines as latent hardeners in compositions having isocyanate groups can, however, also cause problems. In the case of one-component compositions, the storage stability can be restricted significantly as a result of the presence of the aldimine. Depending on the aldehydes used to prepare the aldimine and released again in the curing reaction, the compositions may additionally have a very strong odor, which is intolerable for many applications.

WO 2004/013088 A1 describes odorless polyaldimines which are prepared from primary polyamines and odorless aldehydes. WO 2007/036571 A1 describes odorless aldimines comprising at least one hydroxyl, mercapto or secondary amino group, which are likewise obtainable proceeding from odorless aldehydes. These odorless aldehydes may, in polymer compositions, especially in polyurethane compositions, have a significant plasticizing action, which may be undesired. The relatively high molecular weight of the aldehydes leads, moreover, to a need to use the aldimines prepared therefrom in a relatively large amount as latent hardeners, which can make them expensive to use.

SUMMARY OF THE INVENTION

It is an object of the present invention to provide novel aldimines which can be used as latent hardeners in curable compositions, especially in one- or two-component compositions having isocyanate groups.

It has been found that, surprisingly, aldimines as claimed in claim 1 achieve this object and have advantageous properties. These are usually room temperature liquid compounds which have barely any aldehyde odor and are preparable from readily obtainable base materials in a simple process from primary amines and sterically hindered, aliphatic aldehydes having a tertiary amino group. The aldimines possess good thermal stability. The tertiary amino group thereof has a surprisingly low basicity and can, under some circumstances, display catalytic action in chemical reaction systems.

These aldimines are suitable, for example, as latent hardeners for curable compositions which have groups reactive toward amines, such as epoxide groups, anhydride groups and especially isocyanate groups. Especially in polyurethane compositions, they have very good compatibility and low plasticizing action.

The invention further provides firstly aldimines as claimed in claim 11 and secondly aldimino-containing compounds as claimed in claims 15 and 20, which are reaction products of the aldimines.

The invention further provides curable compositions comprising the aldimines and/or aldimino-containing compounds described as claimed in claims 22 and 23.

Finally, a process for preparing the aldimines as claimed in claim 12, a cured composition as claimed in claim 30 and uses as claimed in claims 31 and 32, and also an article as claimed in claim 33, form further subjects of the present invention.

Further aspects of the invention are the subjects of further independent claims. Particularly preferred embodiments of the invention are the subjects of the dependent claims.

WAYS OF PERFORMING THE INVENTION

The invention provides aldimines of the formula (I)

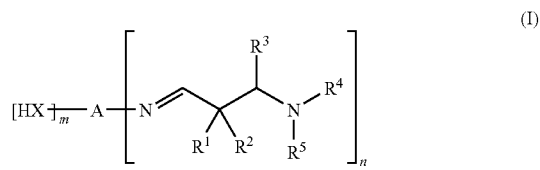

(I)

where
A is either
the radical of an amine after removal of n primary aliphatic amino groups and m HX groups,
or together with $R^7$ is an (n+2)-valent hydrocarbon radical which has 3 to 20 carbon atoms and optionally contains at least one heteroatom, especially in the form of ether oxygen or tertiary amine nitrogen;
n is 1 or 2 or 3 or 4, preferably 1 or 2, and
m is 0 or 1 or 2 or 3 or 4,
with the proviso that m+n is 2 or 3 or 4 or 5;
$R^1$ and $R^2$ are either
each independently a monovalent hydrocarbon radical having 1 to 12 carbon atoms,
or together are a divalent hydrocarbon radical having 4 to 12 carbon atoms which is part of an optionally substituted carbocyclic ring having 5 to 8, preferably 6, carbon atoms;
$R^3$ is a hydrogen atom or an alkyl group or an arylalkyl group or an alkoxycarbonyl group, especially having 1 to 12 carbon atoms;
$R^4$ and $R^5$ are either
each independently a monovalent aliphatic, cycloaliphatic or arylaliphatic radical which has 1 to 20 carbon atoms and is free of hydroxyl groups and optionally contains heteroatoms in the form of ether oxygen or tertiary amine nitrogen,
or together are a divalent aliphatic radical which has 3 to 20 carbon atoms and is part of an optionally substituted heterocyclic ring having 5 to 8, preferably 6, ring atoms, this ring being free of hydroxyl groups and, as well as the nitrogen atom, optionally containing further heteroatoms in the form of ether oxygen or tertiary amine nitrogen;
X is O or S or N—$R^6$ or N—$R^7$, where R⁶ is
either a monovalent hydrocarbon radical which has 1 to 20 carbon atoms and optionally has at least one carboxylic ester, nitrile, nitro, phosphonic ester, sulfone or sulfonic ester group,
or a substituent of the formula (II)

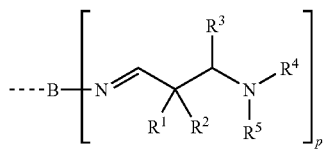
(II)

where
p is 0 or an integer from 1 to 10 000, and
B is a (p+1)-valent hydrocarbon radical which optionally contains ether oxygen, tertiary amine nitrogen, hydroxyl groups, secondary amino groups or mercapto groups; and
R⁷ together with A is an (n+2)-valent hydrocarbon radical which has 3 to 20 carbon atoms and optionally contains at least one heteroatom, especially in the form of ether oxygen or tertiary amine nitrogen.

The broken lines in the formulae in this document each represent the bond between a substituent and the rest of the associated molecule.

The term "primary amino group" in the present document denotes an amino group in the form of an NH₂ group which is bonded to an organic radical. The term "secondary amino group" denotes an amino group in which the nitrogen atom is bonded to two organic radicals which may also together be part of a ring. The term "tertiary amino group" denotes an amino group in which the nitrogen atom is bonded to three organic radicals, where two of these radicals may also together be part of a ring (=tertiary amine nitrogen).

"Aliphatic" refers to an amine or an amino group in which the nitrogen atom is bonded exclusively to aliphatic, cycloaliphatic or arylaliphatic radicals.

The term "active hydrogen" in the present document refers to the hydrogen atom of a hydroxyl, mercapto or secondary amino group.

Preferably, R¹ and R² in formula (I) are each a methyl group.

Preferably, R³ in formula (I) is a hydrogen atom.

Preferably, R⁴ and R⁵ do not have any tertiary amine nitrogen.

In one embodiment of the aldimines of the formula (I), the index m is 1 or 2 or 3 or 4, preferably 1. Such aldimines thus have at least one active hydrogen.

Particularly preferred aldimines of the formula (I) with at least one active hydrogen are aldimines of the formula (Ia)

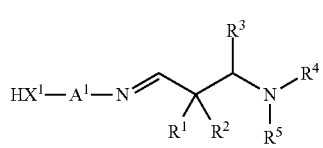
(Ia)

where
A¹ does not have any active hydrogen or any primary amino groups and
is either
a divalent hydrocarbon radical which has 2 to 20 carbon atoms and optionally contains at least one heteroatom, especially in the form of ether oxygen or tertiary amine nitrogen,
or
together with R⁹ is a trivalent hydrocarbon radical which has 3 to 20 carbon atoms and optionally contains at least one heteroatom, especially in the form of ether oxygen or tertiary amine nitrogen;
X¹ is O or S or N—R⁸ or N—R⁹,
where R⁸ is
either a monovalent hydrocarbon radical which has 1 to 20 carbon atoms and optionally has at least one carboxylic ester, nitrile, nitro, phosphonic ester, sulfone or sulfonic ester group,
or a substituent of the formula (IIa)

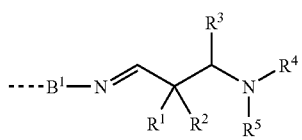
(IIa)

where B¹ is a divalent hydrocarbon radical which has 2 to 12 carbon atoms and optionally has ether oxygen or tertiary amine nitrogen; and
R⁹ together with A¹ is a trivalent hydrocarbon radical which has 3 to 20 carbon atoms and optionally contains at least one heteroatom, especially in the form of ether oxygen or tertiary amine nitrogen,
and R¹, R², R³, R⁴ and R⁵ are each as defined above.

In a further embodiment of the aldimines of the formula (I), the index m is zero and the index n is 2 or 3 or 4. Such aldimines are polyaldimines. Substance names beginning with "poly", such as polyaldimine, polyamine or polyisocyanate, refer in the present document to substances which, in a formal sense, contain two or more of the functional groups which occur in their name per molecule.

Particularly preferred aldimines of the formula (I) where m=0 are aldimines of the formula (Ib)

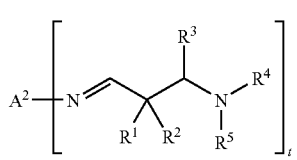
(Ib)

where
t is 2 or 3, preferably 2;
A² is the radical of a polyamine with t primary amino groups after removal of t primary amino groups and does not contain any active hydrogen;
and R¹, R², R³, R⁴ and R⁵ are each as defined above.

The aldimines of the formula (Ib) do not have any active hydrogen.

Aldimines of the formula (I) are obtainable from the reaction of at least one amine B of the formula (III) with at least one sterically hindered aliphatic aldehyde ALD of the formula (IV)

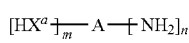 (III)

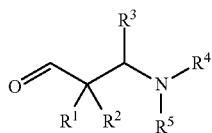 (IV)

where
X$^a$ is O or S or N—R$^{6a}$ or N—R$^7$,
where R$^{6a}$ is either a monovalent hydrocarbon radical which has 1 to 20 carbon atoms and optionally has at least one carboxylic ester, nitrile, nitro, phosphonic ester, sulfone or sulfonic ester group,
or a substituent of the formula (III')

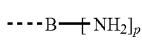 (III')

and m, n, A, B, R$^1$, R$^2$, R$^3$, R$^4$, R$^5$ and p are each as already defined.

The reaction between an amine B of the formula (III) and an aldehyde ALD of the formula (IV) is effected in a condensation reaction with elimination of water. Such condensation reactions are very well known and are described, for example, in Houben-Weyl, "Methoden der organischen Chemie" [Methods of Organic Chemistry], vol. XI/2, page 73 ff. The aldehyde ALD is used here stoichiometrically or in a stoichiometric excess in relation to the primary amino groups of the amine B. Typically, such condensation reactions are performed in the presence of a solvent, by means of which the water which forms in the reaction is removed azeotropically. To prepare the aldimines of the formula (I), however, preference is given to a preparation process without use of solvents, wherein the water formed in the condensation is removed directly from the reaction mixture by means of application of vacuum. By virtue of the solvent-free preparation, there is no need to distill off the solvent on completion of preparation, which simplifies the preparation process. In addition, the aldimine is thus free of solvent residues which could cause a troublesome odor.

Suitable amines B are compounds which, as well as one or more primary amino groups, have at least one reactive group bearing an active hydrogen in the form of a hydroxyl, mercapto or secondary amino group. Examples of amines B with more than one reactive group bearing active hydrogen are
aliphatic amines bearing more than one secondary amino group and one or more primary amino groups, such as N,N'-bis(3-aminopropyl)ethylenediamine, triethylenetetramine (TETA), tetraethylenepentamine (TEPA), pentaethylenehexamine, and higher homologs of linear polyethyleneamines, N,N'-bis(3-aminopropyl)ethylene-diamine, products from the multiple cyanoethylation or cyanobutylation and subsequent hydrogenation of primary di- and polyamines with a plurality of primary amino groups, such as N,N'-bis(3-aminopropyl) ethylenediamine, N,N'-bis(3-aminopropyl)-1,4-diaminobutane, N,N'-bis(3-aminopropyl)-2-methyl-1,5-pentanediamine, N,N'-bis(3-amino-1-ethylpropyl)-2-methyl-1,5-pentanediamine, and also polyethyleneimines of different degrees of polymerization (molar mass range 500 to 1 000 000 g/mol), as obtainable, for example, under the Lupasol® trade name from BASF in pure form or as aqueous solutions, these polyethyleneimines comprising, as well as primary and secondary amino groups, also tertiary amino groups;
hydroxylamines bearing more than one hydroxyl group and one or more primary amino groups, especially derivatives of polyalkoxylated trihydric or higher polyhydric alcohols or of polyalkoxylated polyamines, and also amino sugars, for example glucosamine or galactosamine;
hydroxypolyamines bearing at least one hydroxyl group and at least one secondary amino group from the cyanoethylation or cyanobutylation and subsequent hydrogenation of hydroxylamines such as N-hydroxyethyl-1,2-ethanediamine, N-hydroxypropyl-1,2-ethanediamine, N-hydroxyethyl-1,3-propanediamine, N3-hydroxyethyl-1,3-pentanediamine.

Suitable amines B are additionally polyamines which have two or more primary aliphatic amino groups. Examples of amines B having more than three primary aliphatic amino groups are polyvinylamines or copolymers bearing primary amino groups, for example formed from allylamine and (meth)acrylates.

Particularly suitable amines B are firstly amines B1 of the formula (IIIa)

HX$^{1a}$-A$^1$-NH$_2$ (IIIa)

where
X$^{1a}$ is O or S or N—R$^{8a}$ or N—R$^9$,
where R$^{8a}$ is either a monovalent hydrocarbon radical which has 1 to 20 carbon atoms and optionally has at least one carboxylic ester, nitrile, nitro, phosphonic ester, sulfone or sulfonic ester group,
or a substituent of the formula (IIIa')

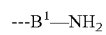 (IIIa')

and A$^1$, B$^1$ and R$^9$ are each as already defined.

The amines B1 are especially suitable for preparing aldimines of the formula (Ia).

Examples of amines B1 are
compounds with one or two primary aliphatic amino groups and one secondary amino group, for example N-methyl-1,2-ethanediamine, N-ethyl-1,2-ethanediamine, N-butyl-1,2-ethanediamine, N-hexyl-1,2-ethanediamine, N-(2-ethylhexyl)-1,2-ethanediamine, N-cyclohexyl-1,2-ethanediamine, 4-aminomethylpiperidine, 3-(4-amino-butyl)piperidine, N-(2-aminoethyl) piperazine, diethylenetriamine (DETA), bishexamethylenetriamine (BHMT), 3-(2-aminoethyl) aminopropylamine; di- and triamines from the cyanoethylation or cyanobutylation and subsequent hydrogenation of primary mono- and diamines, for example N-methyl-1,3-propanediamine, N-ethyl-1,3-propanediamine, N-butyl-1,3-propanediamine, N-hexyl-1,3-propanediamine, N-(2-ethylhexyl)-1,3-propanediamine, N-dodecyl-1,3-propanediamine, N-cyclo-hexyl-1,3-propanediamine, 3-methylamino-1-pentylamine, 3-ethylamino-1-pentylamine, 3-butylamino-1-pentylamine, 3-hexylamino-1-pentylamine, 3-(2-ethylhexyl)amino-1-pentylamine, 3-dodecylamino-1-pentylamine, 3-cyclo-hexylamino-1-pentylamine, dipropylenetriamine (DPTA), N3-(3-aminopentyl)-1,3-pentanediamine, N5-(3-amino-propyl)-2-methyl-1,5-pentanediamine, N5-(3-amino-1-ethylpropyl)-2-methyl-1,5-pentanediamine, and fatty diamines such as N-cocoalkyl-1,3-propanediamine, N-oleyl-1,3-propanediamine, N-soyaalkyl-1,3-propane-diamine, N-tallowalkyl-1,3-propanediamine or N—($C_{16-22}$-alkyl)-1,3-propanediamine, as obtainable, for example, under the trade name Duomeen® from Akzo Nobel; the products from the Michael-type addition of aliphatic primary di- or triamines with acrylonitrile, maleic or fumaric diesters, citraconic diesters, acrylic and methacrylic esters, acryl- and methacrylamides and itaconic diesters, reacted in a molar ratio of 1:1;

aliphatic hydroxylamines, for example 2-aminoethanol, 2-methylaminoethanol (=2-amino-1-propanol), 1-amino-2-propanol, 3-amino-1-propanol, 4-amino-1-butanol, 4-amino-2-butanol, 2-amino-2-methylpropanol, 5-amino-1-pentanol, 6-amino-1-hexanol, 7-amino-1-heptanol, 8-amino-1-octanol, 10-amino-1-decanol, 12-amino-1-dodecanol, 4-(2-aminoethyl)-2-hydroxyethylbenzene, 3-aminomethyl-3,5,5-trimethylcyclohexanol; derivatives bearing one primary amino group of glycols such as diethylene glycol, dipropylene glycol, dibutylene glycol and higher oligomers and polymers of these glycols, for example 2-(2-aminoethoxy)ethanol, triethylene glycol monoamine(=2-(2-(2-aminoethoxy)ethoxy)ethanol), α-(2-hydroxymethylethyl)-ω-(2-aminomethylethoxy)poly(oxy(methyl-1,2-ethane-diyl)); derivatives bearing one hydroxyl group and one primary amino group of polyalkoxylated trihydric or higher polyhydric alcohols; products from the single cyanoethylation and subsequent hydrogenation of glycols, for example 3-(2-hydroxyethoxy)propylamine, 3-(2-(2-hydroxyethoxy)ethoxy)propylamine and 3-(6-hydroxyhexyloxy)propylamine;

aliphatic mercaptoamines, for example 2-aminoethanethiol (cysteamine), 3-aminopropanethiol, 4-amino-1-butanethiol, 6-amino-1-hexanethiol, 8-amino-1-octane-thiol, 10-amino-1-decanethiol, 12-amino-1-dode-canethiol, and amino thiosugars such as 2-amino-2-deoxy-6-thioglucose.

Preferred amines B1 are N-methyl-1,2-ethanediamine, N-ethyl-1,2-ethanediamine, N-cyclohexyl-1,2-ethane-diamine, N-methyl-1,3-propanediamine, N-ethyl-1,3-propanediamine, N-butyl-1,3-propanediamine, N-cyclo-hexyl-1,3-propanediamine, 4-aminomethylpiperidine, 3-(4-aminobutyl)piperidine, DETA, DPTA, BHMT, and fatty diamines such as N-cocoalkyl-1,3-propanediamine, N-oleyl-1,3-propanediamine, N-soyaalkyl-1,3-propane-diamine and N-tallowalkyl-1,3-propanediamine; products from the Michael-type addition reaction of aliphatic primary diamines with maleic and fumaric diesters, acrylic and methacrylic esters, acryl- and meth-acrylamides, preferably with maleic diesters, especially dimethyl, diethyl, dipropyl and dibutyl maleate, and with acrylic esters, especially methyl acrylate, reacted in a molar ratio of 1:1; and also aliphatic hydroxy- or mercaptoamines in which the primary amino group is separated from the hydroxyl or mercapto group by a chain of at least 5 atoms, or by a ring, especially 5-amino-1-pentanol, 6-amino-1-hexanol and higher homologs thereof, 4-(2-aminoethyl)-2-hydroxyethylbenzene, 3-aminomethyl-3,5,5-trimethyl-cyclohexanol, 2-(2-aminoethoxy)ethanol, triethylene glycol monoamine and higher oligomers and polymers thereof, 3-(2-hydroxyethoxy)propylamine, 3-(2-(2-hydroxyethoxy)ethoxy)propylamine and 3-(6-hydroxy-hexyloxy)propylamine.

Particularly preferred amines B1 are amines which are selected from the group consisting of N-methyl-1,2-ethanediamine, N-ethyl-1,2-ethanediamine, N-cyclohexyl-1,2-ethanediamine, N-methyl-1,3-propanediamine, N-ethyl-1,3-propanediamine, N-butyl-1,3-propanediamine, N-cyclohexyl-1,3-propanediamine, 4-aminomethyl-piperidine, 3-(4-aminobutyl)piperidine, DETA, DPTA, BHMT, fatty diamines such as N-cocoalkyl-1,3-propanediamine, N-oleyl-1,3-propanediamine, N-soya-alkyl-1,3-propanediamine and N-tallowalkyl-1,3-propane-diamine, 5-amino-1-pentanol, 6-amino-1-hexanol, 4-(2-aminoethyl)-2-hydroxyethylbenzene, 3-aminomethyl-3,5,5-trimethylcyclohexanol, 2-(2-aminoethoxy)ethanol, triethylene glycol monoamine, 3-(2-hydroxyethoxy)-propylamine, 3-(2-(2-hydroxyethoxy)ethoxy)propylamine and 3-(6-hydroxyhexyloxy)propylamine.

Particularly suitable amines B are secondly amines B2 of the formula (IIIb)

$$A^2\text{---}[NH_2]_t \qquad\qquad (IIIb)$$

where $A^2$ and t are each as already defined.

The amines B2 are especially suitable for preparing aldimines of the formula (Ib).

Examples of amines B2 are aliphatic, cycloaliphatic or arylaliphatic diamines, for example ethylenediamine, 1,2-propanediamine, 1,3-propanediamine, 2-methyl-1,2-propanediamine, 2,2-dimethyl-1,3-propanediamine, 1,3-butanediamine, 1,4-butanediamine, 1,3-pentanediamine (DAMP), 1,5-pentanediamine, 1,5-diamino-2-methylpentane (MPMD), 1,6-hexanediamine, 2,5-dimethyl-1,6-hexanediamine, 2,2,4- and 2,4,4-trimethylhexamethylene-diamine (TMD), 1,7-heptanediamine, 1,8-octanediamine, 1,9-nonane-diamine, 1,10-decanediamine, 1,11-undecanediamine, 1,12-dodecanediamine and methylbis(3-aminopropyl)amine, 1,2-, 1,3- and 1,4-di-aminocyclohexane, bis(4-aminocyclohexyl)methane, bis(4-amino-3-methylcyclo-hexyl)methane, bis(4-amino-3-ethylcyclohexyl)methane, bis(4-amino-3,5-dimethylcyclohexyl)methane, bis(4-amino-3-ethyl-5-methylcyclohexyl)methane (M-MECA), 1-amino-3-aminomethyl-3,5,5-trimethylcyclohexane (=isophoronediamine or IPDA), 2- and 4-methyl-1,3-diaminocyclohexane and mixtures thereof, 1,3- and 1,4-bis(aminomethyl)cyclohexane, 2,5(2,6)bis(aminomethyl)-bicyclo[2.2.1]heptane (NBDA), 3(4),8(9)bis(amino-methyl)tricyclo[5.2.1.0$^{2,6}$]decane, 1,4-diamino-2,2,6-trimethylcyclohexane (TMCDA), 3,9-bis(3-aminopropyl)-2,4,8,10-tetraoxaspiro[5.5]undecane, and 1,3- and 1,4-xylylenediamine;

aliphatic diamines containing ether groups, for example bis(2-aminoethyl)ether, 3,6-dioxaoctane-1,8-diamine, 4,7-dioxadecane-1,10-diamine, 4,7-dioxadecane-2,9-diamine, 4,9-dioxadodecane-1,12-diamine, 5,8-dioxa-dodecane-3,10-diamine and higher oligomers of these diamines, bis(3-aminopropyl)polytetrahydrofurans and other polytetrahydrofurandiamines with molecular weights in the range from, for example, 350 to 5200, and polyoxyalkylenediamines. The latter are typically products from the amination of polyoxyalkylenediols and are obtainable, for example, under the Jeffamine® name (from Huntsman Chemicals), under the Polyetheramine name (from BASF) or under the PC Amine® name (from Nitroil). Especially suitable polyoxyalkylenediamines are Jeffamine® D-230, Jeffamine® D-400, Jeffamine® D-2000, Jeffamine® D-4000, Jeffamine® XTJ-511, Jeffamine® ED-600, Jeffamine® ED-900, Jeffamine® ED-2003, Jeffamine® XTJ-568, Jeffamine® XTJ-569, Jeffamine® XTJ-523, Jeffamine® XTJ-536, Jeffamine XTJ-542, Jeffamine® XTJ-559; Polyetheramine D 230, Polyetheramine D 400 and Polyetheramine D 2000, PC Amine® DA 250, PC Amine® DA 400, PC Amine® DA 650 and PC Amine® DA 2000;

aliphatic triamines such as 4-aminomethyl-1,8-octanediamine, 1,3,5-tris(aminomethyl)benzene, 1,3,5-tris(aminomethyl)cyclohexane;

polyoxyalkylenetriamines, which are typically products from the amination of polyoxyalkylenetriols and are obtainable, for example, under the Jeffamine® trade name (from Huntsman Chemicals), under the Polyetheramine name (from BASF) or under the PC Amine® name (from Nitroil), for example Jeffamine® T-403, Jeffamine® T-5000; Polyetheramine T403, Polyetheramine T5000; and PC Amine® TA 403, PC Amine® TA 5000.

Preferred amines B2 are polyamines which are selected from the group consisting of 1,6-hexamethylenediamine, MPMD, DAMP, IPDA, TMD, 1,3-xylylenediamine, 1,3-bis(aminomethyl)cyclohexane, bis(4-aminocyclohexyl)-methane, bis(4-amino-3-methylcyclohexyl)methane, 3(4),8(9)bis(aminomethyl)tricyclo[5.2.1.0$^{2,6}$]decane, 1,2-, 1,3- and 1,4-diaminocyclohexane, 1,4-diamino-2,2,6-trimethylcyclohexane, 3,6-dioxaoctane-1,8-diamine, 4,7-dioxadecane-1,10-diamine, 4-aminomethyl-1,8-octanediamine and polyoxyalkylenepolyamines having two or three amino groups, especially the D-230, D-400, D-2000, T-403 and T-5000 types obtainable under the Jeffamine® trade name from Huntsman, and analogous compounds from BASF or Nitroil, and mixtures of the polyamines mentioned. Particularly preferred amines B2 are the diamines mentioned.

To prepare an aldimine of the formula (I), at least one sterically hindered aliphatic aldehyde ALD of the formula (IV) is additionally used

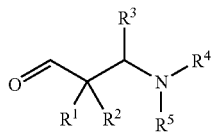

(IV)

where $R^1$, $R^2$, $R^3$, $R^4$ and $R^5$ are each as already defined.

$R^1$ and $R^2$ are preferably each a methyl group, and $R^3$ is preferably a hydrogen atom.

$R^4$ and $R^5$ are preferably each independently ethyl, propyl, isopropyl, butyl, 2-ethylhexyl, cyclohexyl or benzyl, or they form together—including the nitrogen atom—a ring, especially a pyrrolidine, piperidine, morpholine or N-alkylpiperazine ring, which ring is optionally substituted. $R^4$ and $R^5$ more preferably do not have any tertiary amine nitrogen.

Aldehydes ALD of the formula (IV) are obtainable especially as the product of a Mannich reaction or of an α-aminoalkylation analogous to the Mannich reaction, as known from the technical literature; they may therefore also be referred to as Mannich bases. An aldehyde Y1 of formula (V), an aldehyde Y2 of the formula (VI) and a secondary aliphatic amine C of the formula (VII) are converted to an aldehyde ALD with elimination of water

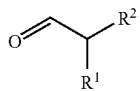

(V)

-continued

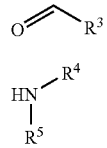

(VI)

(VII)

where $R^1$, $R^2$, $R^3$, $R^4$ and $R^5$ are each as already defined.

This reaction can either be conducted with the free reagents Y1, Y2 and C of the formulae (V), (VI) and (VII), or the reagents can be used partly or completely in derivatized form. For example, the aldehyde Y1 can be used as the enolate, as the enol ether, especially as the silyl enol ether, or as the enamine. The aldehyde Y2 can be used, for example, in the form of an oligomer—in the case of formaldehyde especially as 1,3,5-trioxane or as paraformaldehyde—or as the hydrate, hemiacetal, acetal, N,O-acetal, aminal or hemiaminal. The secondary aliphatic amine C, finally, can be used, for example, as the salt, especially as the amine hydrochloride or as the amine hydrosulfate, or as the silylamine. It is possible to use a portion of the reagents in free form and a portion in derivatized form, or to proceed only from derivatized forms. In the case of use of reagents in derivatized form, the aldehyde ALD is under some circumstances likewise obtained in derivatized form, for example as the salt; in this case, it can be converted by suitable workup to the free form of the formula (IV). According to the circumstances, it may be advisable additionally to use assistants such as Lewis acids or catalysts in such conversion reactions.

In addition, the reaction can be conducted as a one-pot reaction in which all three reagents can react simultaneously with one another; or else a stepwise method can be selected, by first reacting two of the reagents with one another and then reacting the intermediate thus obtained with the third reagent, it being possible to isolate the intermediate or not. Suitable intermediates of this kind are especially iminium salts, which are obtained from the reaction of an aldehyde Y2, in free or derivatized form, with a salt of a secondary aliphatic amine C, and which can be reacted with an aldehyde Y1, in free or derivatized form, to give the corresponding salt of an aldehyde ALD of the formula (IV). Such a stepwise method may have the advantage of enabling milder reaction conditions and hence of providing a higher product yield.

In addition, the reaction can be performed using solvents, especially polar solvents such as water or alcohols, or the reaction can be effected without use of solvents.

In a preferred embodiment, the reaction is conducted as a one-pot reaction with all reagents in free form and the aldehyde ALD is purified by distillation on completion of reaction. Preference is given to using no organic solvents.

Examples of suitable aldehydes Y1 of the formula (V) are the following aldehydes: isobutyraldehyde, 2-methylbutyraldehyde, 2-ethylbutyraldehyde, 2-methyl-valeraldehyde, 2-ethylcapronaldehyde, cyclopentanecarboxaldehyde, cyclohexanecarboxaldehyde, 1,2,3,6-tetrahydrobenzaldehyde, 2-methyl-3-phenyl-propionaldehyde, 2-phenylpropionaldehyde and diphenylacetaldehyde. Preference is given to isobutyraldehyde.

Examples of suitable aldehydes Y2 of the formula (VI) are the following aldehydes: formaldehyde, acetaldehyde, propionaldehyde, butyraldehyde, isobutyraldehyde, phenylacetaldehyde, benzaldehyde and substituted benzaldehydes, and also glyoxylic esters, especially ethyl glyoxylate. Preference is given to formaldehyde.

Examples of suitable amines C of the formula (VII) are the following secondary aliphatic amines: dimethylamine, diethylamine, dipropylamine, diisopropylamine, dibutylamine, diisobutylamine, di-sec-butylamine, dihexylamine, di(2-ethylhexyl)amine, dicyclohexylamine, N-methylbutylamine, N-ethyl-butylamine, N-methylcyclohexylamine, N-ethylcyclo-hexylamine, di-2-methoxyethylamine, pyrrolidine, piperidine, N-methylbenzylamine, N-isopropyl-benzylamine, N-tert-butylbenzylamine, dibenzylamine, morpholine, 2,6-dimethylmorpholine, bis(3-dimethyl-aminopropyl) amine, N-methyl- or N-ethylpiperazine.

Preferred amines C are dimethylamine, diethylamine, diisopropylamine, dibutylamine, diisobutylamine, N-methylcyclohexylamine, N-methylbenzylamine, N-isopropylbenzylamine, N-tert-butylbenzylamine, dibenzylamine, pyrrolidine, piperidine, morpholine and 2,6-dimethylmorpholine.

The aldehyde ALD is preferably prepared by the reaction of isobutyraldehyde as aldehyde Y1 of the formula (V), formaldehyde as aldehyde Y2 of the formula (VI) and one of the amines selected from the group comprising dimethylamine, diethylamine, diisopropylamine, dibutylamine, diisobutylamine, N-methylcyclohexylamine, N-methylbenzylamine, N-isopropylbenzylamine, N-tert-butylbenzylamine, dibenzylamine, pyrrolidine, piperidine, morpholine and 2,6-dimethylmorpholine as amine C of the formula (VII).

Preferred aldehydes ALD are 2,2-dimethyl-3-dimethylaminopropanal, 2,2-dimethyl-3-diethylaminopropanal, 2,2-dimethyl-3-dibutylaminopropanal, 2,2-dimethyl-3-(N-pyrrolidino)propanal, 2,2-dimethyl-3-(N-piperidino)-propanal, 2,2-dimethyl-3-(N-morpholino)propanal, 2,2-dimethyl-3-(N-(2,6-dimethyl)morpholino)propanal, 2,2-dimethyl-3-(N-benzylmethylamino)propanal, 2,2-dimethyl-3-(N-benzylisopropylamino)propanal and 2,2-dimethyl-3-(N-cyclohexylmethylamino)propanal. The preferred aldehydes ALD do not have any additional tertiary amine nitrogen and have a comparatively low basicity.

The aldehydes ALD of the formula (IV) have a series of special properties. For instance, they possess a good thermal stability because the carbon atom in the a position to the aldehyde group does not bear a hydrogen atom, and the elimination of a secondary amine to form an alkene is therefore impossible. They also have a surprisingly good stability with respect to oxidation by atmospheric oxygen. Moreover, the basicity thereof—based on the central tertiary amine nitrogen in the 3 position—is surprisingly significantly lower than expected for aliphatic amines of similar structure; the $pK_a$ measured for the conjugated acid of an aldehyde ALD is about 2 units lower than that of the conjugated acid of the secondary amine C used to prepare this aldehyde ALD. These surprising properties are possibly connected to an intramolecular 1,4 interaction between amine and aldehyde group (orbital overlap between the free electron pair of the nitrogen and the $\pi$ or $\pi^*$ orbital of the carbonyl), as postulated by P. Y. Johnson et al. (J. Org. Chem., vol. 40, 19, 1975; pages 2710-2720) on the basis of NMR and UV spectroscopy studies on β-aminoaldehydes.

Finally, the aldehydes ALD, even in the case of relatively low molecular weight, have only a slight, amine-like odor, if any. This property of low odor intensity, which is surprising for aldehydes, probably results firstly from the intramolecular 1,4 interaction mentioned, but secondly from the steric hindrance of the aldehyde group which is on a tertiary carbon atom.

Aldimines of the formula (I) can be prepared, as already described, directly from amines B and aldehydes ALD.

Aldimines of the formula (I) which have an N—$R^6$ substituent as the substituent X can optionally be prepared by a slightly different route than that described so far. This synthesis route consists in reacting an aldehyde ALD of the formula (IV) with a di- or trifunctional, preferably difunctional, aliphatic primary amine, as already described previously as amine B2, in a first step to give an intermediate which, as well as one or two aldimino groups, also contains one or two primary amino groups, preferably one primary amino group. This intermediate is subsequently converted in a second step to an aldimine of the formula (I), by monoalkylating the primary amino group. The compounds used for the alkylation are especially those with only one activated double bond which can enter into Michael-type addition reactions with primary amines; such compounds are referred to hereinafter as "Michael acceptors".

An aldehyde ALD is reacted with an amine B2 to give the intermediate having a primary amino group in a condensation reaction with elimination of water, as described above for the reaction of an aldehyde ALD with an amine B of the formula (III). However, the stoichiometry between the aldehyde ALD and the amine B2 is selected such that 1 mol of aldehyde ALD is used for 1 mol of amine B2, which contains two primary amino groups, or in such a way that 2 mol of aldehyde ALD are used for 1 mol of amine B2 which contains three primary amino groups. The amine B2 used is preferably asymmetric in relation to the amino groups. Preference is given to a solvent-free preparation process wherein the water formed in the condensation is removed from the reaction mixture by means of application of vacuum.

The intermediate having one primary amino group is reacted with the Michael acceptor, for example, by mixing the intermediate with a stoichiometric or slightly superstoichiometric amount of the Michael acceptor and heating the mixture at temperatures of 20 to 110° C. until complete conversion of the intermediate to the aldimine of the formula (I). The reaction is effected preferably without the use of solvents.

Preferred amines B2 for this preparation are diamines in which the primary amino groups are separated by a chain of at least five atoms, or by a ring, especially 1,5-diamino-2-methylpentane, 1,6-hexamethylenediamine, 2,2,4- and 2,4,4-trimethylhexamethylenediamine and mixtures thereof, 1,10-decanediamine, 1,12-dodecane-diamine, 1,3- and 1,4-diaminocyclohexane, bis(4-aminocyclohexyl)methane, bis (4-amino-3-methylcyclo-hexyl)methane, 1-amino-3-aminomethyl-3,5,5-trimethyl-cyclohexane, 1,3- and 1,4-bis (aminomethyl)cyclohexane, 2,5(2,6)bis(aminomethyl) bicyclo[2.2.1]heptane, 3(4),8(9)bis(aminomethyl)tricyclo [5.2.1.0$^{2,6}$]decane, 1,4-diamino-2,2,6-trimethylcyclohexane (TMCDA), 3,9-bis(3-aminopropyl)-2,4,8,10-tetraoxaspiro [5.5]undecane, 1,3- and 1,4-xylylenediamine, and also the aliphatic diamines containing ether groups and polyoxyalkylenediamines mentioned.

Examples of suitable Michael acceptors are maleic or fumaric diesters such as dimethyl maleate, diethyl maleate, dibutyl maleate, diethyl fumarate; citraconic diesters such as dimethyl citraconate; acrylic or methacrylic esters such as methyl(meth)acrylate, ethyl(meth)acrylate, butyl(meth)acrylate, lauryl(meth)acrylate, stearyl(meth)acrylate, tetrahydrofuryl(meth)acrylate, isobornyl(meth)acrylate; itaconic diesters such as dimethyl itaconate; cinnamic esters such as methyl cinnamate; vinylphosphonic diesters such as dimethyl vinylphosphonate; vinylsulfonic esters, especially aryl vinylsulfonate; vinyl sulfones; vinyl nitriles such as acrylonitrile, 2-pentenenitrile or fumaronitrile; 1-nitroethylenes such as β-nitrostyrene; and Knoevenagel condensation products, for example those formed from malonic diesters and aldehydes such as formaldehyde, acetaldehyde or benzaldehyde. Preference is given to maleic diesters, acrylic esters, phosphonic diesters and vinyl nitriles.

Those embodiments of aldimines of the formula (I) which have at least one HX group may be in equilibrium with cyclic forms, as shown in formula (VIII) by way of example for the case where the index m=1. These cyclic forms are cyclic animals, for example imidazolidines or tetrahydropyrimidines, in the case of amino aldimines, cyclic amino acetals, for example oxazolidines or tetrahydrooxazines, in the case of hydroxyaldimines; cyclic thioaminals, for example thiazolidines or tetrahydrothiazines, in the case of mercaptoaldimines.

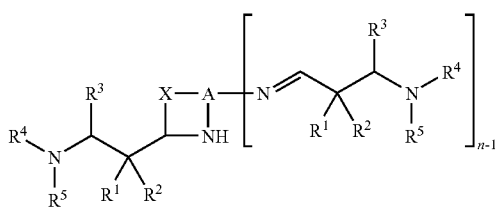

(VIII)

In the formula (VIII), n, A, $R^1$, $R^2$, $R^3$, $R^4$, $R^5$ and X are each as already defined.

Surprisingly, most aldimines of the formula (I) containing HX groups do not tend to cyclize. Especially for amino aldimines, it is possible to show by means of IR and NMR spectroscopy methods that these compounds are present predominantly in the open-chain form, i.e. the aldimine form, whereas the cyclic form, i.e. the aminal form, occurs only in traces, if at all. Hydroxy- and mercaptoamines in which the primary amino group is separated from the hydroxyl group or the mercapto group by a chain of at least 5 atoms, or by a ring, exhibit barely any cyclization.

The aldimines of the formula (I) are novel compounds which have not been described to date and have surprising properties. They contain sterically hindered aldimino groups which do not have a hydrogen atom on the carbon atom in the a position and therefore cannot tautomerize to enamino groups. As a result, these aldimino groups are particularly well-protected ("blocked") primary amino groups which exhibit only low reactivity, if any, with compounds reactive toward amino groups under exclusion of moisture. Moreover, the aldimines of the formula (I) have a tertiary amino group which can display catalytic action in chemical reaction systems under some circumstances; the basicity of the aldimines of the formula (I) originating from the tertiary amino group is, however, surprisingly low. Moreover, the aldimines of the formula (I), even at relatively low molecular weight of the parent aldehyde ALD, have only a slight, amine-like odor, if any.

The aldimines of the formula (I) possess good thermal stability, since the carbon atom in the a position to the aldimino group, as mentioned, does not bear a hydrogen atom and the elimination of a secondary amine to form an alkene is therefore impossible.

The aldimines of the formula (I) are storage-stable under suitable conditions. On ingress of moisture, the aldimino groups thereof can be hydrolyzed in a formal sense via intermediates to amino groups, which releases the corresponding aldehydes ALD of the formula (IV) used to prepare the aldimines, which, as already described, are low-odor or odorless.

Since this hydrolysis reaction is reversible and the chemical equilibrium is clearly to the aldimine side, it can be assumed that, in the absence of compounds reactive toward amines, only some of the aldimino groups hydrolyze partly or completely. Surprisingly, the hydrolysis of the aldimino groups, in spite of the presence of tertiary amino groups, can be catalyzed by means of acids.

The aldimines of the formula (I) are preparable in a relatively simple process from readily obtainable starting substances. If nonviscous amines B of the formula (III) were used in the preparation thereof, some of the corresponding aldimines of the formula (I) are likewise nonviscous compounds.

The aldimines of the formula (I) can be used very widely. They can be used, for example, wherever they can serve as a source of aldehydes ALD of the formula (IV) or of amines B of the formula (III). More particularly, they can be used in the function of protected amines, or protected aldehydes, in aldehyde- and/or amine-reactive systems and be deprotected there selectively if required. More particularly, they find use in systems in which compounds which react with primary amines are present. The deprotection is effected hydrolytically, for example by contact with water or moisture, especially air humidity. Surprisingly, the hydrolysis of the aldimino groups, in spite of the presence of tertiary amino groups, can be catalyzed by means of acids just as well as for aldimines without tertiary amino groups in the molecule.

On the other hand, aldimines of the formula (I) with the index m greater than zero find use in the formation of further-functionalized reaction products of these aldimines. For instance, aldimines of the formula (I) with the index m greater than zero can be reacted with compounds which can react with the HX group, especially in addition reactions. Suitable compounds of this kind which enter into addition reactions bear reactive groups, for example isocyanate groups, epoxide groups, anhydride groups or more or less highly activated double or triple bonds such as (meth)acrylate groups, acrylamide groups, 1-ethynylcarbonyl groups, 1-propynylcarbonyl groups, maleimide groups, citraconimide groups, vinyl groups, isopropenyl groups or allyl groups. The reaction products bearing aldimino groups from such addition reactions can be hydrolyzed if required to aldehydes ALD of the formula (IV) and compounds with primary amino groups, and then be utilized for further reactions, for example for crosslinking reactions, hydrolysis reaction being catalyzable by means of acids.

In addition, the aldimines of the formula (I) with the index m greater than zero can be used to prepare aldimino-containing compounds which are suitable, for example, as latent hardeners or as comonomers for reactive compositions, especially for compositions comprising isocyanate groups.

Moreover, the aldimines of the formula (I) can be used as catalysts for chemical reaction systems, for example in curable compositions comprising isocyanate groups, especially in order to shorten the curing time thereof.

Finally, the aldimines of the formula (I) can be used as a source for cationic compounds, by protonating some or all of the tertiary amino groups to ammonium groups or alkylating some or all to quaternary ammonium groups. By protonating or alkylating aldimines of the formula (I), aldimines of the formula (IX) are obtainable

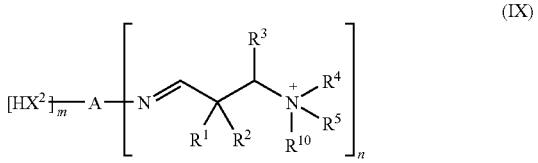
(IX)

where
R¹⁰ is a hydrogen atom or an alkyl, cycloalkyl or arylalkyl radical having 1 to 20 carbon atoms;
X² is O or S or N—R¹¹ or N—R⁷,
where R¹¹ is
either a monovalent hydrocarbon radical which has 1 to 20 carbon atoms and optionally has at least one carboxylic ester, nitrile, nitro, phosphonic ester, sulfone or sulfonic ester group,
or a substituent of the formula (IX');

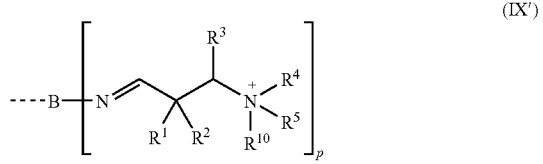
(IX')

and m, n, p, A, B, R¹, R², R³, R⁴ and R⁵ and R⁷ are each as already defined.

Aldimines of the formula (IX) are additionally obtainable proceeding from one of the amines B of the formula (III) mentioned above and an aldehyde ALD of the formula (IV), some or all of the tertiary amino groups of the aldehyde ALD being protonated or alkylated before the reaction with the amine B.

To protonate the aldimines of the formula (I) or the aldehydes ALD, it is possible to use any desired Brønsted acids, for example hydrochloric acid, sulfuric acid, phosphoric acid, carboxylic acids such as acetic acid or benzoic acid, and sulfonic acids such as methanesulfonic acid or p-toluenesulfonic acid. To alkylate the aldimines of the formula (I) or the aldehydes ALD, it is possible to use known alkylating agents, especially methylating agents, for example methyl iodide, dimethyl sulfate, dimethyl phosphonate, diazomethane, methyl fluorosulfate or trimethyloxonium tetrafluoroborate.

It is clear to the person skilled in the art that a cationic aldimine of the formula (IX) also includes an anion which balances the positive charge of the aldimine.

The aldimines of the formula (I) or of the formula (IX) are particularly suitable as a constituent of compositions based on isocyanates or epoxy resins, especially for applications such as adhesives, sealants, potting compositions, coatings, floor coverings, paints, coating materials, primers or foams. Such compositions preferably comprise at least one acid, especially an organic carboxylic or sulfonic acid, or a compound hydrolyzable to these acids, the acid surprisingly catalyzing the hydrolysis of the aldimino groups in spite of the presence of tertiary amino groups.

More particularly, the aldimines of the formula (I) or the aldimines of the formula (IX) are suitable as hardeners or as precursors for hardeners for one- or two-component compositions comprising isocyanate groups, such as adhesives, sealants, potting compositions, coatings, floor coverings, paints, coating materials, primers or foams.

As already mentioned, the aldimines of the formula (I) contain sterically hindered aldimino groups which are not tautomerizable to enamino groups and are particularly well-protected ("blocked") primary amino groups. Together with compounds having isocyanate groups, the aldimines of the formula (I) can form storage-stable mixtures, i.e. of substantially constant viscosity, with exclusion of moisture. Particularly storage-stable mixtures are those comprising compounds having free aliphatic isocyanate groups and/or those comprising compounds having blocked aromatic isocyanate groups—blocked, for example, with phenols.

An isocyanate group or an isocyanate is referred to as "aliphatic" when the isocyanate group is bonded to an aliphatic, cycloaliphatic or arylaliphatic radical, in contrast to an aromatic isocyanate or an aromatic isocyanate group where the isocyanate group is bonded to an aromatic radical.

Compositions composed of compounds having isocyanate groups and aldimines of the formula (I) react on contact with water with hydrolysis of the aldimino groups to give compounds having urea groups. The isocyanate groups react with the primary amino groups which are released in a formal sense by the hydrolysis of the aldimino groups, which releases an aldehyde ALD. Excess isocyanate groups relative to the aldimino groups react directly with moisture and likewise form urea groups. In the case of suitable stoichiometry between isocyanate groups and aldimino groups, the composition cures as a result of these reactions; this process is also referred to as crosslinking. The reaction of the isocyanate groups with the aldimino groups being hydrolyzed need not necessarily proceed via free amino groups. It will be appreciated that reactions with intermediates of the hydrolysis reaction are also possible. For example, it is conceivable that an aldimino group being hydrolyzed reacts directly with an isocyanate group in the form of a hemiaminal. Surprisingly, the acid-catalyzed hydrolysis of the aldimino groups is not impaired by the presence of tertiary amino groups.

The tertiary amino group of the aldimines of the formula (I) may have a catalytic effect on the reaction of the isocyanate groups and may therefore accelerate the crosslinking. This accelerating action is additionally promoted by the fact that the tertiary amino group is localized in the aldehyde part of the aldimine. It is, however, advantageous that the basicity of the tertiary amino groups is comparatively low, since strongly basic tertiary amines can excessively accelerate the direct reaction of the isocyanate groups, especially with water, which can have a disruptive effect in the curing. The hydrolysis of the aldimino groups releases aldehydes ALD of the formula (IV) containing the tertiary amino group. Owing to their relatively small size, the aldehydes ALD have quite good mobility in the curing composition, which potentially additionally increases the catalytic effect thereof on further isocyanate groups. On completion of curing, the aldehydes ALD released remain in the cured composition. They have excellent compatibility there, have no tendency to be sweated out and have only a minor plasticizing effect, which is often very advantageous.

It is also possible to store the aldimines of the formula (I) together with water, with the prerequisite that the aldimines are stored separately from isocyanate groups. Only when the water-aldimine mixture comes into contact with isocyanate groups does the hydrolysis proceed to completion. This is because the reaction between aldimines of the formula (I) and isocyanate groups is highly retarded compared to the reaction of the corresponding primary amines even when the aldimines are stored together with water.

It is likewise possible to use aldimines of the formula (I) or of the formula (IX) in compositions which cure under the influence of heat, for example by the use of compounds with thermally labile, blocked isocyanate groups. It is additionally possible to use aldimines of the formula (I) or of the formula (IX) in compositions which constitute reactive warm- or hot-melt adhesives. Such adhesives comprise meltable compounds especially having isocyanate groups; they are solid at room temperature and are applied warm or hot.

The present invention further provides aldimino-containing compounds AV which are addition products from the reaction of at least one aldimine of the formula (I) where m=1, especially at least one aldimine of the formula (Ia), with at least one compound D which has at least one reactive group, preferably at least two reactive groups, which can enter into addition reactions with the HX group. The HX group of the aldimine of the formula (I) reacts in an addition reaction with one or more reactive groups of the compound D to give an aldimino-containing compound AV.

When the compound D bears at least two reactive groups and this reaction is conducted stoichiometrically, i.e. with one molar equivalent of active hydrogen of the aldimine of the formula (I) for one molar equivalent of reactive groups of the compound D—which completely converts the reactive groups thereof—the aldimino-containing compound AV obtained is a polyaldimine. Polyaldimines are thus obtainable in a simple manner without needing to resort to the corresponding primary polyamines, the availability of which is only limited for technical and commercial reasons, for preparation thereof. Depending on the structure, functionality and molecular weight of the compounds D and of the aldimines of the formula (I), these polyaldimines may have very different properties; they can thus be tailored to the requirements of a particular application. These polyaldimines are especially suitable as latent hardeners for compositions having isocyanate groups.

By virtue of a substoichiometric reaction of the aldimines of the formula (I) with compounds D, it is also possible to prepare aldimino-containing compounds AV which, as well as one or more aldimino groups, also have one or more other reactive groups amenable to poly reactions, known as heterofunctional compounds AV. In this case, less than one molar equivalent of active hydrogen of the aldimine of the formula (I) is used for one molar equivalent of reactive groups of a compound D which bears at least two reactive groups. The compound D itself may be homo- or heterofunctional. Such heterofunctional compounds AV are, for example, useable as comonomers or as latent hardeners for reactive polymer compositions; or, in the case that a heterofunctional compound AV, in addition to at least one aldimino group, has at least one reactive group which can react with aldimino groups being hydrolyzed to link the molecules, also as the reactive polymer composition itself. This is especially true in the case of aldimino-containing compounds AV which additionally have isocyanate groups.

Suitable compounds D are substances which bear at least one, preferably more than one, of the following reactive groups which can enter into addition reactions and which are selected from the group consisting of isocyanate, isothiocyanate, cyclocarbonate, epoxide, episulfide, aziridine, acryloyl, methacryloyl, 1-ethynylcarbonyl, 1-propynylcarbonyl, maleimide, citraconimide, vinyl, isopropenyl and allyl groups. It is also possible that the compound D has different reactive groups among those mentioned above. Preference is given to isocyanate, epoxide, acryloyl, maleimide, vinyl, isopropenyl and allyl groups. Particular preference is given to isocyanate groups.

Examples of suitable compounds D are di- or polyfunctional, monomeric and/or oligomeric, aliphatic, cycloaliphatic, arylaliphatic and aromatic polyisocyanates such as 1,6-hexamethylene diisocyanate (HDI), 2-methylpentamethylene 1,5-diisocyanate, 2,2,4- and 2,4,4-trimethyl-1,6-hexamethylene diisocyanate (TMDI), 1,12-dodecamethylene diisocyanate, lysine and lysine ester diisocyanate, cyclohexane 1,3- and 1,4-diisocyanate and any desired mixtures of these isomers, 1-isocyanato-3,3,5-trimethyl-5-isocyanatomethylcyclo-hexane (=isophorone diisocyanate or IPDI), perhydro-2,4'- and -4,4'-diphenylmethane diisocyanate (HMDI), 1,4-diisocyanato-2,2,6-trimethylcyclohexane (TMCDI), 1,3- and 1,4-bis(isocyanatomethyl)cyclohexane, m- and p-xylylene diisocyanate (m- and p-XDI), 1,3,5-tris(iso-cyanatomethyl)benzene, m- and p-tetramethyl-1,3- and 1,4-xylylene diisocyanate (m- and p-TMXDI), bis(1-isocyanato-1-methylethyl)naphthalene, α,α,α',α',α",α"-hexamethyl-1,3,5-mesitylene triisocyanate, dimer and trimer fatty acid isocyanates such as 3,6-bis(9-isocyanatononyl)-4,5-di(1-heptenyl)-cyclohexene (dimeryl diisocyanate), 2,4- and 2,6-tolylene diisocyanate and any desired mixtures of these isomers (TDI), 4,4'-, 2,4'- and 2,2'-diphenylmethane diisocyanate and any desired mixtures of these isomers (MDI), mixtures of MDI and MDI homologs (polymeric MDI or PMDI), 1,3- and 1,4-phenylene diisocyanate, 2,3,5,6-tetramethyl-1,4-diisocyanatobenzene, naphthalene 1,5-diisocyanate (NDI), 3,3'-dimethyl-4,4'-diisocyanato-diphenyl (TODI), tris(4-isocyanatophenyl)methane, tris(4-isocyanatophenyl)thiophosphate; oligomers of these isocyanates containing uretdione, isocyanurate or iminooxadiazinedione groups; modified di- and polyfunctional isocyanates containing ester, urea, urethane, biuret, allophanate, carbodiimide, uretonimine or oxadiazinetrione groups; and also isocyanate-containing polyurethane polymers, i.e. reaction products, having more than one isocyanate group, of polyisocyanates with substances having two or more hydroxyl groups (known as "polyols"), for example di- or polyfunctional alcohols, glycols or amino alcohols, poly-hydroxy-functional polyethers, polyesters, polyacrylates, polycarbonates or polyhydrocarbons, especially polyethers;

di- or polyfunctional epoxides (polyepoxides) such as bis (2,3-epoxycyclopentyl)ether, polyglycidyl ethers of polyhydric aliphatic and cycloaliphatic alcohols such as 1,4-butanediol, polypropylene glycols and 2,2-bis(4-hydroxycyclohexyl)propane; polyglycidyl ethers of polyhydric phenols such as resorcinol, bis(4-hydroxyphenyl)methane (bisphenol F), 2,2-bis(4-hydroxy-phenyl) propane (bisphenol A), 2,2-bis(4-hydroxy-3,5-dibromophenyl)propane, 1,1,2,2-tetrakis(4-hydroxyphenyl)ethane, condensation products of phenols with formaldehyde which are obtained under acidic conditions, such as phenol novolacs and cresol novolacs, and also polyglycidyl ethers pre-extended with these alcohols and phenols, or with polycarboxylic acids, for example dimeric fatty acids, or a mixture thereof; polyglycidyl esters of polybasic carboxylic acids such as phthalic acid, terephthalic acid, tetra-hydrophthalic acid and hexahydrophthalic acid; N-glycidyl derivatives of amines, amides and heterocyclic nitrogen bases such as N,N-diglycidyl-aniline, N,N-diglycidyltoluidine, N,N,O-triglycidyl-4-aminophenol, N,N,N',N'-tetraglycidyl-bis(4-amino-phenyl)methane, triglycidyl cyanurate and triglycidyl isocyanurate;

di- or polyfunctional compounds bearing acryloyl, methacryloyl or acrylamide groups, such as tris(2-hydroxyethyl)isocyanurate tri(meth)acrylate, tris(2-hydroxyethyl)cyanurate tri(meth)acrylate, N,N',N''-tris(meth)acryloylperhydrotriazine; di- or polyfunctional acrylates and methacrylates of aliphatic polyethers, polyesters, novolacs, phenols, aliphatic or cycloaliphatic alcohols, glycols and polyester glycols, and also mono- and polyalkoxylated derivatives of the aforementioned compounds, for example ethylene glycol di(meth)acrylate, tetraethylene glycol di(meth)acrylate, tripropylene glycol di(meth)acrylate, polyethylene glycol di(meth)acrylate, polypropylene glycol di(meth)acrylate, 1,4-butanediol di(meth)acrylate, 1,6-hexanediol di(meth)acrylate, neopentyl glycol di(meth)acrylate, trimethylolpropane tri(meth)acrylate, pentaerythritol tetra(meth)acrylate, dipentaerythritol tetra(meth)acrylate, dipenta-erythritol penta(meth)acrylate, dipentaerythritol hexa(meth)acrylate; di- or polyfunctional acryloyl- or methacryloyl-functional polybutadienes, polyisoprenes or block copolymers thereof; adducts of di- or polyfunctional epoxides, such as the abovementioned epoxides, with acrylic and methacrylic acid; di- or polyfunctional polyurethane (meth)acrylates; di- or polyfunctional acrylamides such as N,N'-methylene-bisacrylamide;

di- or polyfunctional compounds bearing 1-ethynylcarbonyl or 1-propynylcarbonyl groups;

di- or polyfunctional compounds bearing maleimide or citraconimide groups, such as the bis- and polykismaleimides of aliphatic, cycloaliphatic or aromatic di- and polyamines and maleic or citraconic anhydride, for example α,ω-dimer fatty acid bis(maleimide), 4,4'-diphenylmethanebis(maleimide), 1,3-xylylenebis(citraconimide); bis- and polykismale-imides of amino-terminated butadiene/acrylonitrile copolymers (obtainable, for example, under the Hycar® ATBN name from Noveon) and maleic or citraconic anhydride; di- or polyfunctional adducts of di- and polyisocyanates with N-hydroxyethylmaleimide; esters of di- or polyfunctional alcohols and 6-maleimidohexanoic acid;

di- or polyfunctional compounds bearing vinyl and/or isopropenyl groups, such as 1,3- and 1,4-divinylbenzene, divinyl sulfone, vinyl crotonate, diallylidenepentaerythritol acetal, 1,3-diisopropenyl-benzene and 1,3,5-triisopropenylbenzene, 3-(2-vinyloxy-ethoxy)styrene, divinyldimethylsilane, trivinylmethyl-silane, trivinylmethoxysilane, divinyltetramethyl-disiloxane, 1,3-divinyl-1,3-diphenyl-1,3-dimethyl-disiloxane, 1,3-divinyltetraethoxydisiloxane, trivinyl-pentamethyltrisiloxane, 4-vinyloxybutoxytrivinylsilane, tris(4-vinyloxybutoxy)vinylsilane; di- or polyfunctional vinyl and isopropenyl ethers such as divinyl ether, isopropenyl vinyl ether, triethylene glycol divinyl ether, butanediol divinyl ether, hexane-diol divinyl ether, octadecanediol divinyl ether, dimer fatty acid diol divinyl ether and divinyl butyral; divinyl esters of dicarboxylic acids, for example divinyl adipate;

di- or polyfunctional compounds bearing allyl groups, such as triallyl cyanurate, triallyl isocyanurate, triallyl phosphate; di- or polyfunctional allyl ethers of alcohols and glycols and mono- and polyalkoxylated derivatives thereof, for example 1,4-bis(allyloxy)butane, 1,6-bis(allyloxy)hexane, triethylene glycol diallyl ether, bisphenol A diallyl ether, 3,3'-diallyl bisphenol A diallyl ether, 3,3'-diallyl bisphenol A, trimethylolpropane diallyl ether, glyceryl triallyl ether, trimethylolpropane triallyl ether, pentaerythritol tetraallyl ether; di- or polyfunctional allyl esters and amides of carboxylic acids, for example diallyl phthalate, diallyl iso- and terephthalate, diallyl oxalate, diallyl sebacate, diallyl maleate, diallyl fumarate, diallyl itaconate; difunctional allyl carbonates such as diallyl carbonate, di- and triethylene glycol bis(allyl carbonate); di- or polyfunctional adducts of di- and polyisocyanates with glycidol, allyl alcohol or allyl glycols, for example 1,6-hexamethylenebis(allyl carbamate);

and also di- or polyfunctional heterofunctional compounds, i.e. those bearing at least two different reactive groups among the aforementioned, such as 4-allyloxyphenyl isocyanate, 1-alkenyl isocyanates such as vinyl isocyanate, propenyl isocyanate and isopropenyl isocyanate, 2-isocyanatoethyl methacrylate, 1,2-dimethyl-3-isocyanatopropyl acrylate, p-isocyanato-styrene, m- and p-isopropenyl-α,α-dimethylbenzyl isocyanate (m- and p-TMI), m- and p-ethenyl-α,α-dimethylbenzyl isocyanate, isopropenyl-α,α,α',α'-tetramethylxylylene diisocyanate, glycidyl allyl ether, glycidoxytrivinylsilane, triglycidoxy-vinylsilane, N-(trivinylsilyloxymethyl)maleimide; heterofunctional adducts of di- and polyisocyanates with glycidol, allyl alcohol, allyl glycols, N-hydroxyethylmaleimide, hydroxyfunctional acrylates and methacrylates such as 2-hydroxyethyl acrylate and methacrylate; heterofunctional adducts of mono- and polycarbodiimides of di- and polyisocyanates with acrylic or methacrylic acid; heterofunctional adducts of di- or polyfunctional epoxides with acrylic or methacrylic acid, vinyl allyl ether, ethylene glycol vinyl allyl ether, vinyl allyl phthalate, ethylene glycol 2-allylphenyl vinyl ether, allyl(meth)acrylate, vinyl acrylate, 2-vinyloxyethyl(meth)acrylate.

Especially suitable compounds D are di- or polyfunctional aliphatic, cycloaliphatic, arylaliphatic and aromatic isocyanates such as the monomeric and oligomeric polyisocyanates mentioned, and also the reaction products of polyisocyanates with polyols, said reaction products having more than one isocyanate group, especially polyetherpolyols, polyesterpolyols, polyacrylatepolyols, polycarbonatepolyols, polyhydro-carbonpolyols and mixtures of these polyols.

According to the reactive groups of the compound D and the group of the aldimine of the formula (I) which bears the active hydrogen, the addition reaction which leads to the aldimino-containing compound AV may proceed nucleophilically or free-radically. For reasons of simplicity, the term "addition reaction" in the present document shall also embrace ring-opening substitution reactions, as entered into, for example, by epoxides with nucleophiles, because the result of such a substitution reaction which does not release the nucleofuge as a separate molecule equates to that of an addition reaction. The addition reaction proceeds nucleophilically when the reactive group of the aldimine which bears the active hydrogen, as a nucleophile, attacks an electrophilic reactive group of the compound D, for example in the case of the attack of an amino or hydroxyl group on an isocyanate group. An example which can be specified for a free-radical addition reaction is the reaction of a mercapto group on an acryloyl group, a free-radical-forming initiator generally being required for this kind of addition reaction.

The reaction between the aldimine of the formula (I) and the compound D to give the aldimino-containing compound AV proceeds under known conditions, as are typically used for reactions between the reactive groups involved in the particular reaction, for example at 20 to 100° C. The reaction is effected using a solvent or preferably without solvent. If appropriate, it is possible to use assistants, for example catalysts, initiators or stabilizers. For amino aldimines the reaction with isocyanates is preferably performed at room temperature and without catalyst, for hydroxy-, mercapto- and ureaaldimines at 40 to 100° C. and with use of a catalyst as used for the urethanization reaction between isocyanates and alcohols, for example an organotin compound, a bismuth complex, a tertiary amine compound or a combination of such catalysts.

The aldimino-containing compounds AV obtained in the manner described are, like the aldimines of the formula (I), virtually or completely odorless. They are storage-stable under suitable conditions, especially with exclusion of moisture. Heterofunctional aldimino-containing compounds AV which, as well as aldimino groups, contain additional reactive groups amenable to poly reactions are storage-stable when they are kept away from factors which induce reactions of these reactive groups, for example heat or UV radiation.

On ingress of moisture, the aldimino groups of the aldimino-containing compounds AV can be hydrolyzed in a formal sense via intermediates to amino groups, which releases the corresponding aldehyde ALD of the formula (IV) which is used to prepare the aldimine and is likewise virtually or completely odorless. Since this hydrolysis reaction is reversible and the chemical equilibrium is clearly to the aldimine side, it can be assumed that, in the absence of groups reactive toward amines, only some of the aldimino groups will be hydrolyzed partially or completely. In the specific case of heterofunctional aldimino-containing compounds AV which contain groups reactive toward amines, especially isocyanate groups, the aldimino groups which hydrolyze, in contrast, react further, for example with isocyanate groups to give urea groups. In this case, the result is crosslinking of the heterofunctional aldimino-containing compound AV, which can also lead directly to a cured polymer composition without involvement of further substances. The reaction of the groups reactive toward amines with the aldimino groups being hydrolyzed need not necessarily proceed via amino groups. It will be appreciated that reactions with intermediates of the hydrolysis reaction are also possible. For example, it is conceivable that the aldimino group being hydrolyzed reacts directly with the groups reactive toward amines in the form of a hemiaminal.

The aldimino-containing compounds AV can be used, for example, as a source for cationic aldimino-containing compounds, by protonating some or all of the tertiary amino groups to give ammonium groups or alkylating some or all to give quaternary ammonium groups.

A preferred embodiment of an aldimino-containing compound AV is the aldimino-containing compound AV1 of the formula (X)

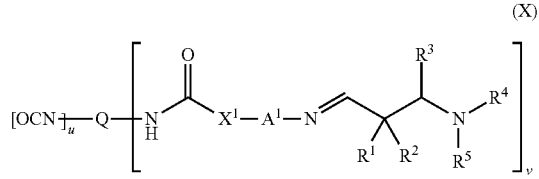

wherein
u is 0 or 1 or 2 or 3 or 4 or 5,
v is 1 or 2 or 3 or 4 or 5 or 6,
with the proviso that (u+v) is 2 or 3 or 4 or 5 or 6;

Q is the radical of a polyisocyanate having (u+v) isocyanate groups after removal of all isocyanate groups;
and $A^1$, $X^1$, $R^1$, $R^2$, $R^3$, $R^4$ and $R^5$ are each as already defined.

An aldimino-containing compound AV1 of the formula (X) is obtainable by the reaction of at least one polyisocyanate of the formula (XI) with at least one aldimine having only one active hydrogen of the formula (Ia) already mentioned.

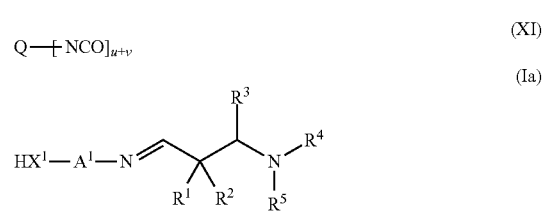

In the formula (XI), Q, u and v are each defined as already described.

A suitable polyisocyanate of the formula (XI) is, in one embodiment, a polyurethane polymer PUP having isocyanate groups.

In the present document, the term "polymer" firstly embraces a collective of macromolecules which are chemically homogeneous but different in relation to degree of polymerization, molar mass and chain length, which has been prepared by a poly reaction (polymerization, polyaddition, polycondensation). The term secondly also embraces derivatives of such a collective of macromolecules from poly reactions, i.e. compounds which have been obtained by reactions, for example additions or substitutions, of functional groups on given macromolecules, and which may be chemically homogeneous or chemically inhomogeneous. The term further also comprises what are known as prepolymers, i.e. reactive oligomeric preliminary adducts whose functional groups are involved in the formation of macromolecules.

The term "polyurethane polymer" embraces all polymers prepared by what is known as the diisocyanate polyaddition process. This also includes those polymers which are virtually or entirely free of urethane groups. Examples of polyurethane polymers are polyetherpolyurethanes, polyesterpolyurethanes, polyetherpolyureas, polyureas, polyesterpolyureas, polyisocyanurates and polycarbodiimides.

A suitable polyurethane polymer PUP having isocyanate groups is obtainable by the reaction of at least one polyol with at least one polyisocyanate.

The polyols used for the preparation of a polyurethane polymer PUP may, for example, be the following polyols or mixtures thereof:

polyetherpolyols, also known as polyoxyalkylene-polyols or oligoetherols, which are polymerization products of ethylene oxide, 1,2-propylene oxide, 1,2- or 2,3-butylene oxide, tetrahydrofuran or mixtures thereof, possibly polymerized with the aid of a starter molecule, for example water, ammonia, 1,2-ethanediol, 1,2- and 1,3-propanediol, neopentyl glycol, diethylene glycol, triethylene glycol, the isomeric dipropylene glycols and tripropylene glycols, the isomeric butanediols, pentanediols, hexanediols, heptanediols, octanediols, nonanediols, decanediols, undecanediols, 1,3- and 1,4-cyclohexanedimethanol, bisphenol A, hydrogenated bisphenol A, 1,1,1-trimethylolethane, 1,1,1-trimethylolpropane, glycerol, aniline, and mixtures of the aforementioned compounds. It is possible to use either polyoxyalkylenepolyols which have a low degree of unsaturation (measured to ASTM D-2849-69 and reported in milliequivalents of unsaturation per gram of polyol (meq/g)), prepared, for example, with the aid of double metal cyanide complex catalysts (DMC catalysts), or polyoxy-alkylenepolyols with a higher degree of unsaturation, prepared, for example, with the aid of anionic catalysts such as NaOH, KOH, CsOH or alkali metal alkoxides.

Particularly suitable polyetherpolyols are polyoxyalkylenediols and -triols, especially polyoxy-alkylenediols. Particularly suitable polyoxyalkylenedi- and -triols are polyoxyethylenedi- and -triols and polyoxypropylenedi- and -triols.

Particularly suitable polyoxypropylenediols and -triols have a degree of unsaturation lower than 0.02 meq/g and a molecular weight in the range from 1000 to 30 000 g/mol, and also polyoxypropylenediols and -triols with a molecular weight of 400 to 8000 g/mol. In the present document, "molecular weight" or "molar mass" is always understood to mean the molecular weight average $M_n$. Especially suitable are polyoxypropylene-diols with a degree of unsaturation less than 0.02 meq/g and a molecular weight in the range from 1000 to 12 000 and especially between 1000 and 8000 g/mol. Such polyetherpolyols are sold, for example, under the trade name Acclaim® by Bayer.

Likewise particularly suitable are so-called "EO-endcapped" (ethylene oxide-endcapped) polyoxy-propylenediols and -triols. The latter are specific polyoxypropylenepolyoxyethylenepolyols which are obtained, for example, by alkoxylating pure polyoxy-propylenepolyols with ethylene oxide on completion of the polypropoxylation, and have primary hydroxyl groups as a result.

Styrene-acrylonitrile- or acrylonitrile-methyl methacrylate-grafted polyetherpolyols.

Polyesterpolyols, also known as oligoesterols, prepared by known processes, especially the polycondensation of hydroxycarboxylic acids or the polycondensation of aliphatic and/or aromatic polycarboxylic acids with di- or polyhydric alcohols.

Especially suitable polyesterpolyols are those prepared from di- to trivalent, especially divalent, alcohols, for example ethylene glycol, diethylene glycol, propylene glycol, dipropylene glycol, neopentyl glycol, 1,4-butanediol, 1,5-pentanediol, 3-methyl-1,5-hexane-diol, 1,6-hexanediol, 1,8-octanediol, 1,10-decanediol, 1,12-dodecanediol, 1,12-hydroxystearyl alcohol, 1,4-cyclohexanedimethanol, dimer fatty acid diol (dimer diol), neopentyl glycol hydroxypivalate, glycerol, 1,1,1-trimethylolpropane or mixtures of the aforementioned alcohols, with organic di- or tricarboxylic acids, especially dicarboxylic acids, or the anhydrides or esters thereof, for example succinic acid, glutaric acid, adipic acid, trimethyladipic acid, suberic acid, azelaic acid, sebacic acid, dodecanedicarboxylic acid, maleic acid, fumaric acid, dimer fatty acid, phthalic acid, phthalic anhydride, isophthalic acid, terephthalic acid, dimethyl terephthalate, hexahydrophthalic acid, trimellitic acid and trimellitic anhydride, or mixtures of the aforementioned acids, and also polyesterpolyols formed from lactones, for example from ε-caprolactone, and starters such as the aforementioned di- or trihydric alcohols.

Particularly suitable polyesterpolyols are polyesterdiols.

Polycarbonatepolyols, as obtainable by reaction, for example, of the abovementioned alcohols—used to form the polyesterpolyols—with dialkyl carbonates such as dimethyl carbonate, diaryl carbonates such as diphenyl carbonate, or phosgene.

Particularly suitable substances are polycarbonate-diols.

Block copolymers which bear at least two hydroxyl groups and have at least two different blocks with polyether, polyester and/or polycarbonate structure of the type described above.

Polyacrylate- and polymethacrylatepolyols.

Poly-hydroxy-functional fats and oils, for example natural fats and oils, especially castor oil; or polyols—known as oleochemical polyols—obtained by chemical modification of natural fats and oils, for example the epoxy polyesters or epoxy polyethers obtained by epoxidation of unsaturated oils and subsequent ring opening with carboxylic acids or alcohols, or polyols obtained by hydroformylation and hydrogenation of unsaturated oils; or polyols obtained from natural fats and oils by degradation processes such as alcoholysis or ozonolysis and subsequent chemical linkage, for example by transesterification or dimerization, of the degradation products or derivatives thereof thus obtained. Suitable degradation products of natural fats and oils are especially fatty acids and fatty alcohols, and also fatty acid esters, especially the methyl esters (FAME), which can be derivatized, for example, by hydroformylation and hydrogenation to hydroxy fatty acid esters.

Polyhydrocarbonpolyols, also known as oligohydro-carbonols, for example poly-hydroxy-functional polyolefins, polyisobutylenes, polyisoprenes; poly-hydroxy-functional ethylene-propylene, ethylene-butylene or ethylene-propylene-diene copolymers, as produced, for example, by Kraton Polymers, poly-hydroxy-functional polymers of dienes, especially of 1,3-butadiene, which can especially also be prepared from anionic polymerization; poly-hydroxy-functional copolymers of dienes such as 1,3-butadiene or diene mixtures, and vinyl monomers such as styrene, acrylonitrile, vinyl chloride, vinyl acetate, vinyl alcohol, isobutylene and isoprene, for example poly-hydroxy-functional acrylonitrile/butadiene copolymers, which can be prepared, for example, from carboxyl-terminated acrylonitrile/butadiene copolymers (commercially available under the Hycar® CTBN name from Noveon) and epoxides or amino alcohols; and hydrogenated poly-hydroxy-functional polymers or copolymers of dienes.

These polyols mentioned preferably have a mean molecular weight of 250-30 000 g/mol, especially of 400-20 000 g/mol, and preferably have a mean OH functionality in the range from 1.6 to 3.

In addition to these polyols mentioned, small amounts of low molecular weight di- or polyhydric alcohols, for example 1,2-ethanediol, 1,2- and 1,3-propanediol, neopentyl glycol, diethylene glycol, triethylene glycol, the isomeric dipropylene glycols and tripropylene glycols, the isomeric butanediols, pentanediols, hexanediols, heptanediols, octanediols, nonanediols, decanediols, undecanediols, 1,3- and 1,4-cyclohexanedimethanol, hydrogenated bisphenol A, dimeric fatty alcohols, for example dimer fatty acid diols, 1,1,1-trimethylolethane, 1,1,1-trimethylol-propane, glycerol, pentaerythritol, low molecular weight alkoxylation products of the aforementioned di- and polyhydric alcohols, and mixtures of the aforementioned alcohols, can be used additionally in the preparation of a polyurethane polymer PUP.

The polyisocyanates used for the preparation of a polyurethane polymer PUP may be aliphatic, cycloaliphatic or aromatic polyisocyanates, especially diisocyanates, for example the following:

monomeric aliphatic diisocyanates, for example 1,6-hexamethylene diisocyanate (HDI), 2-methyl-pentamethylene 1,5-diisocyanate, 2,2,4- and 2,4,4-trimethyl-1,6- hexamethylene diisocyanate (TMDI), 1,10-decamethylene diisocyanate, 1,12-dodeca-methylene diisocyanate, lysine diisocyanate and lysine ester diisocyanate, cyclohexane 1,3- and 1,4-diisocyanate and any desired mixtures of these isomers, 1-methyl-2,4- and -2,6-diisocyanato-cyclohexane and any desired mixtures of these isomers (HTDI or $H_6$TDI), 1-isocyanato-3,3,5-trimethyl-5-isocyanatomethylcyclohexane (=iso-phorone diisocyanate or IPDI), perhydro-2,4'- and -4,4'-diphenylmethane diisocyanate (HMDI or $H_{12}$MDI), 1,4-diisocyanato-2,2,6-trimethylcyclo-hexane (TMCDI), 1,3- and 1,4-bis(isocyanato-methyl)cyclohexane, m- and p-xylylene diisocyanate (m- and p-XDI), m- and p-tetramethyl-1,3- and -1,4-xylylene diisocyanate (m- and p-TMXDI), bis(1-isocyanato-1-methylethyl)naphthalene.

Monomeric aromatic diisocyanates, for example 2,4- and 2,6-tolylene diisocyanate and any desired mixtures of these isomers (TDI), 4,4'-, 2,4'- and 2,2'-diphenylmethane diisocyanate and any desired mixtures of these isomers (MDI), 1,3- and 1,4-phenylene diisocyanate, 2,3,5,6-tetramethyl-1,4-diisocyanatobenzene, naphthalene 1,5-diisocyanate (NDI), 3,3'-dimethyl-4,4'-diisocyanatodiphenyl (TODI), dianisidine diisocyanate (DADI).

Oligomers and polymers of the aforementioned monomeric aliphatic or aromatic diisocyanates.

Any desired mixtures of the aforementioned polyisocyanates.

Preference is given to monomeric diisocyanates, especially MDI, TDI, HDI and IPDI.

A polyurethane polymer PUP is prepared in a known manner directly from the polyisocyanates and the polyols, or by stepwise adduction processes, as also known as chain extension reactions.

In a preferred embodiment, the polyurethane polymer PUP is prepared via a reaction of at least one polyisocyanate and at least one polyol, the isocyanate groups being present in a stoichiometric excess relative to the hydroxyl groups. The ratio between isocyanate and hydroxyl groups is advantageously 1.3 to 5, especially 1.5 to 3.

The reaction is advantageously performed at a temperature at which the polyols and polyisocyanates used and the polyurethane polymer formed are present in liquid form.

The polyurethane polymer PUP has a molecular weight of preferably more than 500 g/mol, especially one between 1000 and 50 000 g/mol, preferably one between 2000 and 30 000 g/mol.

Moreover, the polyurethane polymer PUP preferably has a mean functionality in the range from 1.8 to 3.

In a further embodiment, a polyisocyanate of the formula (XI) suitable for reaction with an aldimine of the formula (Ia) is a polyisocyanate PI in the form of a monomeric diisocyanate or of an oligomer of a monomeric diisocyanate or of a derivative of a monomeric diisocyanate, for which suitable diisocyanates are the same monomeric diisocyanates as have already been specified as suitable for preparation of a polyurethane polymer PUP.

Suitable polyisocyanates PI are in particular oligomers or derivatives of monomeric diisocyanates, especially of HDI, IPDI, TDI and MDI. Commercially available types are especially HDI biurets, for example as Desmodur® N 100 and N 3200 (Bayer), Tolonate® HDB and HDB-LV (Rhodia) and Duranate® 24A-100 (Asahi Kasei); HDI isocyanurates, for example as Desmodur® N 3300, N 3600 and N 3790 BA (all from Bayer), Tolonate® HDT, HDT-LV and HDT-LV2 (Rhodia), Duranate® TPA-100 and THA-100 (Asahi Kasei) and Coronate® HX (Nippon Polyurethane); HDI uretdiones, for example as Desmodur® N 3400 (Bayer); HDI iminooxadiazinediones, for example as Desmodur® XP 2410 (Bayer); HDI allophanates, for example as Desmodur® VP LS 2102 (Bayer); IPDI isocyanurates, for example in solution as Desmodur® Z 4470 (Bayer) or in solid form as Vestanat® T1890/100 (Degussa); TDI oligomers, for example as Desmodur® IL (Bayer); and mixed isocyanurates based on TDI/HDI, for example as Desmodur® HL (Bayer). Additionally particularly suitable are room temperature liquid forms of MDI (known as "modified MDI"), which are mixtures of MDI with MDI derivatives, for example MDI carbodiimides or MDI uretonimines or MDI urethanes, known for example under trade names such as Desmodur® CD, Desmodur® PF, Desmodur® PC (all from Bayer), and mixtures of MDI and MDI homologs (polymeric MDI or PMDI), obtainable under trade names such as Desmodur® VL, VL50, VL R10, VL R20 and Desmodur® VKS 20F (all from Bayer), Isonate® M 309, Voranate® M 229, Voranate M® 580 (all from Dow) or Lupranat® M 10 R (from BASF).

Preferred polyisocyanates PI are the oligomers of HDI and/or IPDI, especially the isocyanurates.

The aforementioned oligomeric polyisocyanates PI are typically mixtures of substances with different degrees of oligomerization and/or chemical structures. They preferably have a mean NCO functionality of 2.1 to 4.0 and contain especially isocyanurate, iminooxadiazine-dione, uretdione, urethane, biuret, allophanate, carbodiimide, uretonimine or oxadiazinetrione groups. These oligomers preferably have a low content of monomeric diisocyanates.

It is likewise possible that a polyisocyanate of the formula (XI) suitable for reaction with an aldimine of the formula (Ia) is a mixture consisting of at least one polyurethane polymer PUP and at least one polyisocyanate PI.

To prepare an aldimino-containing compound AV1 of the formula (X), at least one polyisocyanate of the formula (XI) is reacted with at least one aldimine of the formula (Ia). Suitable for this purpose are the above-described aldimines of the formula (Ia), or the preferred embodiments thereof, as have already been described in detail above.

The reaction of a polyisocyanate of the formula (XI) with an aldimine of the formula (Ia) to give an aldimino-containing compound AV1 of the formula (X) is effected under conditions as typically used for reactions between the reactive groups involved in the particular reaction, as have been described above.

When this addition reaction is performed stoichiometrically, i.e. with one molar equivalent of active hydrogen of the aldimine of the formula (Ia) for one molar equivalent of isocyanate groups of the polyisocyanate of the formula (XI)—which completely converts the reactive groups thereof—the addition product obtained is an aldimino-containing compound AV1 of the formula (X) with the index u equal to zero. Such a compound AV1 is a polyaldimine.

When this addition reaction, in contrast, is conducted substoichiometrically, i.e. with less than one molar equivalent of active hydrogen of the aldimine of the formula (Ia) for one molar equivalent of isocyanate groups of the polyisocyanate of the formula (XI)—which only partly converts the isocyanate groups—the addition product obtained is a heterofunctional compound, i.e. an aldimino-containing compound AV1 of the formula (X) which, as well as one or more aldimino groups, also has at least one isocyanate group. The index u in the formula (X) in this case is greater than zero.

An aldimino-containing compound AV1 of the formula (X) which has isocyanate groups—i.e. which has an index u in the formula (X) greater than zero—owing to storage stability is preferably prepared proceeding from a polyisocyanate of the formula (XI) which has exclusively aliphatic isocyanate groups.

The aldimino-containing compounds AV1 of the formula (X) are storage-stable under suitable conditions, especially with exclusion of moisture.

In the substoichiometric reaction of a polyurethane polymer PUP with an aldimine of the formula (Ia), the HX group reacts preferentially with the monomeric diisocyanates typically present in the polyurethane polymer PUP. In this way, the content of monomeric diisocyanates in the polyurethane polymer PUP is greatly reduced.

A further preferred embodiment of an aldimino-containing compound AV is an aldimino-containing compound AV2 of the formula (XII)

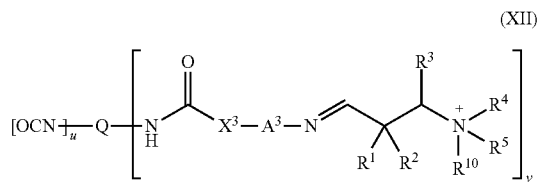

where
$A^3$ does not have any active hydrogen or any primary amino groups and is either
  a divalent hydrocarbon radical which has 2 to 20 carbon atoms and optionally contains at least one heteroatom, especially in the form of ether oxygen or tertiary amine nitrogen,
or
  together with $R^{12}$ is a trivalent hydrocarbon radical which has 3 to 20 carbon atoms and optionally contains at least one heteroatom, especially in the form of ether oxygen or tertiary amine nitrogen; and
$X^3$ is O or S or N—$R^{11}$ or N—$R^{12}$,
  where $R^{12}$ together with $A^3$ is a trivalent hydrocarbon radical which has 3 to 20 carbon atoms and optionally contains at least one heteroatom, especially in the form of ether oxygen or tertiary amine nitrogen;
and Q, u, v, $R^1$, $R^2$, $R^3$, $R^4$, $R^5$, $R^{10}$ and $R^{11}$ are each as already defined.

In one embodiment, an aldimino-containing compound AV2 of the formula (XII) is obtainable proceeding from an aldimino-containing compound AV1 of the formula (X) which is protonated or alkylated. For protonation or alkylation, it is possible to use the same Brønsted acids or alkylating agents as already described for preparation of aldimines of the formula (IX).

In a further embodiment, an aldimino-containing compound AV2 of the formula (XII) is obtainable proceeding from an aldimine of the formula (IX) where m=1 and n=1, which is reacted with a polyisocyanate of the formula (XI) already specified.

The invention further provides curable compositions, also referred to hereinafter as polyurethane compositions, which comprise at least one polyisocyanate and either at least one aldimine of the formula (I) or of the formula (IX) or at least one aldimino-containing compound AV.

The term "polyisocyanate" in the present document encompasses compounds having two or more isocyanate groups, irrespective of whether they are monomeric diisocyanates, oligomeric polyisocyanates or polymers which contain isocyanate groups and have a relatively high molecular weight.

Suitable aldimines of the formula (I) are the aldimines of the formula (I) already described in detail above, or the preferred embodiments thereof, especially the aldimines of the formula (Ia) or the aldimines of the formula (Ib). Suitable aldimines of the formula (IX) have already been described above. Suitable aldimino-containing compounds AV are the aldimino-containing compounds AV described in detail above, or the preferred embodiments thereof, especially the aldimino-containing compounds AV1 of the formula (X). Particularly suitable aldimino-containing compounds AV1 are those in which the index u is zero, i.e. polyaldimines.

Particularly suitable aldimines of the formula (I) are additionally those obtainable proceeding from aldehydes ALD with relatively low basicity. These are in turn products from amines C with relatively low basicity, such as especially morpholines and N-alkylbenzylamines. Aldehydes ALD with relatively low basicity are especially 2,2-dimethyl-3-(N-morpholino)propanal, 2,2-dimethyl-3-(N-(2,6-dimethyl)morpholino)propanal, 2,2-dimethyl-3-(N-benzylmethylamino) propanal and 2,2-dimethyl-3-(N-benzylisopropylamino) propanal.

Preference is given to curable compositions comprising at least one polyisocyanate and either at least one aldimine of the formula (I) or at least one aldimino-containing compound AV.

In one embodiment, the curable composition has one component.

In the present document, a "one-component" composition refers to a curable composition in which all constituents of the composition are stored mixed in the same container, and which is storage-stable over a prolonged period at room temperature, i.e. the performance or use properties thereof change only insignificantly, if at all, as a result of the storage, and which cures through the action of moisture and/or heat after application.

The one-component curable composition comprises at least one polyisocyanate. The isocyanate groups thereof may be present in the composition either as free isocyanate groups or as blocked isocyanate groups, or in mixed form.

A "blocked isocyanate group" in the present document is understood to mean an isocyanate group whose reactivity toward nucleophiles, as a result of the above reaction of a free isocyanate group with a blocking agent known from the prior art, for example a phenol, a ketoxime, a pyrazole or a malonic diester, has been reduced to such a degree that it is storage-stable together with suitable hardeners at room temperature and only begins to react with these hardeners under the action of heat and/or moisture, the blocking agent being released or not being released according to the type.

The one-component curable composition may be moisture-curing and/or heat-curing.

A "heat-curing composition" in the present document is understood to mean a composition comprising blocked isocyanate groups, in which the isocyanate groups, in the course of heating to a suitable temperature, typically in the range from 120 to 200° C., in special cases even at temperatures from 80° C., are activated to such an extent that crosslinking and hence curing occur with suitable hardeners. This operation is also referred to as baking and is typically effected after the application of the composition.

The isocyanate groups of the polyisocyanate in the one-component moisture-curing composition are preferably present as free isocyanate groups, especially as free aliphatic isocyanate groups.

In the one-component curable composition, the ratio between aldimino groups and isocyanate groups is especially 0.1 to 1.1, preferably 0.3 to 0.9, more preferably 0.4 to 0.8, equivalent of aldimino groups per equivalent of isocyanate groups, it being possible for the isocyanate groups to be present either in free or blocked form.

A preferred one-component curable composition is a one-component curable composition which comprises at least one polyisocyanate P1 having aliphatic isocyanate groups and either at least one aldimine of the formula (I) or at least one aldimino-containing compound AV.

Suitable polyisocyanates P1 are firstly polyurethane polymers PUP1 having aliphatic isocyanate groups. A polyurethane polymer PUP1 is obtainable in this way from polyols and polyisocyanates, as described above for the polyurethane polymer PUP. Suitable polyols are the polyols already mentioned, and suitable polyisocyanates are the aliphatic polyisocyanates already mentioned, preference being given to monomeric aliphatic diisocyanates, especially IPDI, HDI, TMDI and HMDI.

Suitable polyisocyanates P1 are secondly polyisocyanates PI1 in the form of a monomeric aliphatic diisocyanate or of an oligomer thereof, as already mentioned above, especially an oligomer of HDI or IPDI.

Further suitable polyisocyanates P1 are mixtures comprising at least one polyurethane polymer PUP1 and at least one polyisocyanate PI1.

The one-component moisture-curing composition comprises, as well as at least one polyisocyanate P1, additionally either at least one aldimine of the formula (I) or at least one aldimino-containing compound AV. Preferred aldimines of the formula (I) are the aldimines of the formula (Ib), and preferred aldimino-containing compounds AV are aldimino-containing compounds AV1 of the formula (X). An aldimino-containing compound AV1 of the formula (X) can also be formed in situ in the composition, by adding an aldimine of the formula (Ia) in a suitable substoichiometric amount to a composition comprising at least one polyisocyanate P1, the aldimino-containing compound AV1 being formed in the manner described above. This incorporates a portion of the polyisocyanate P1 as the polyisocyanate of the formula (XI) into the aldimino-containing compound AV1.

Optionally, the one-component moisture-curing composition comprises further constituents, especially the assistants and additives typically used in polyurethane compositions, for example the following:

plasticizers, for example carboxylic esters such as phthalates, for example dioctyl phthalate, diisononyl phthalate or diisodecyl phthalate, adipates, for example dioctyl adipate, azelates and sebacates, organic phosphoric and sulfonic esters or polybutenes;

nonreactive thermoplastic polymers, for example homo- or copolymers of unsaturated monomers, especially from the group comprising ethylene, propylene, butylene, isobutylene, isoprene, vinyl acetate and alkyl(meth) acrylates, especially polyethylenes (PE), polypropylenes (PP), polyisobutylenes, ethylene-vinyl acetate copolymers (EVA) and atactic poly-α-olefins (APAOs);

solvents;

inorganic and organic fillers, for example ground or precipitated calcium carbonates optionally coated with fatty acids, especially stearates, barite ($BaSO_4$, also known as heavy spar), quartz flours, calcined kaolins, aluminum oxides, aluminum hydroxides, silicas, especially finely divided silicas from pyrolysis processes, carbon blacks, especially industrially produced carbon blacks (referred to hereinafter as "carbon black"), PVC powders or hollow spheres;

fibers, for example of polyethylene;

pigments, for example titanium dioxide or iron oxides;

catalysts which accelerate the hydrolysis of the aldimino groups, especially acids, for example organic carboxylic acids such as benzoic acid, salicylic acid or 2-nitrobenzoic acid, organic carboxylic anhydrides such as phthalic anhydride, hexahydrophthalic anhydride and hexahydromethyl-phthalic anhydride, silyl esters of organic carboxylic acids, organic sulfonic acids such as methanesulfonic acid, p-toluenesulfonic acid or 4-dodecylbenzenesulfonic acid, sulfonic esters, other organic or inorganic acids, or mixtures of the aforementioned acids and acid esters;

catalysts which accelerate the reaction of the isocyanate groups, for example organotin compounds such as dibutyltin diacetate, dibutyltin dilaurate, dibutyltin dichloride, dibutyltin diacetylacetonate and dioctyltin dilaurate, bismuth compounds such as bismuth trioctoate and bismuth tris(neodecanoate), and compounds containing tertiary amino groups, such as 2,2'-dimorpholinodiethyl ether and 1,4-diaza-bicyclo[2.2.2]octane;

rheology modifiers, for example thickeners or thixotropic agents, for example urea compounds, polyamide waxes, bentonites or fumed silicas;

reactive diluents and crosslinkers, for example monomeric diisocyanates such as MDI, PMDI, TDI, HDI, 1,12-dodecamethylene diisocyanate, cyclohexane 1,3- or 1,4-diisocyanate, IPDI, perhydro-2,4'- and -4,4'-diphenylmethane diisocyanate, 1,3- and 1,4-tetramethylxylylene diisocyanate, and also oligomers and derivatives of these polyisocyanates, especially in the form of isocyanurates, carbodiimides, uretonimines, biurets, allophanates or iminooxadiazinediones, adducts of monomeric polyisocyanates with short-chain polyols, and also adipic dihydrazide and other dihydrazides, and also polyisocyanates with blocked aromatic isocyanate groups, for example the Desmocap® products 11, 12 and XP 2540 (all from Bayer) and the Trixene® products BI 7641, BI 7642, BI 7770, BI 7771, BI 7772, BI 7774 and BI 7779 (all from Baxenden);

blocked amines, for example in the form of ketimines, oxazolidines, enamines or other aldimines;

desiccants, for example molecular sieves, calcium oxide, high-reactivity isocyanates such as p-tosyl isocyanate, orthoformic esters, alkoxysilanes such as tetraethoxysilane, organoalkoxysilanes such as vinyltrimethoxysilane, and organoalkoxysilanes which have a functional group in the a position to the silane group;

adhesion promoters, especially organoalkoxysilanes ("silanes"), for example epoxysilanes, vinylsilanes, (meth) acrylsilanes, isocyanato-silanes, carbamatosilanes, alkylsilanes, S-(alkylcarbonyl)mercaptosilanes and aldimino-silanes, and oligomeric forms of these silanes;

stabilizers against heat, light and UV radiation;

flame-retardant substances;

surface-active substances, for example wetting agents, leveling agents, devolatilizers or defoamers;

biocides, for example algicides, fungicides or substances which inhibit fungal growth.

When such further constituents are used, it is advantageous to ensure that they do not significantly impair the storage stability of the composition. This means that these constituents must not trigger the reactions which lead to crosslinking, such as hydrolysis of the aldimino groups or crosslinking of the isocyanate groups, to a significant degree during storage. More particularly, this means that all of these constituents should contain at most traces of water, if any. It may be advisable to chemically or physically dry certain constituents before they are mixed into the composition.

The one-component moisture-curing composition preferably comprises at least one catalyst. The catalyst is especially one of the acids mentioned, such as benzoic acid or salicylic acid, or one of the metal compounds mentioned, or one of the tertiary amines mentioned. It may quite possibly be advantageous to use different catalysts or different catalyst types.

The one-component moisture-curing composition is produced and stored with exclusion of moisture. It is storage-stable, i.e. it can be stored with exclusion of moisture in a suitable package or arrangement, for example a drum, a bucket, a pouch, a cartridge or a bottle, over a period of several months for example, without its performance properties or its properties after curing changing to a degree relevant for the use thereof. According to the consistency of the composition, it is customary to determine the storage stability via the measurement of the viscosity.

The aldimino groups of the aldimine of the formula (I) and/or of the aldimino-containing compound AV have the property of being hydrolyzed on contact with moisture. The primary amino groups that this releases in a formal sense react at the same time with the isocyanate groups present in the composition to give urea groups, and the corresponding aldehyde ALD of the formula (IV) is released. Excess isocyanate groups in relation to the aldimino groups react directly with moisture and likewise form urea groups. Any blocked isocyanate groups present generally react with release of the blocking agent likewise to give urea groups, which reaction may proceed only under the action of heat. As a result of these reactions, the composition cures to give a solid material; this process is also referred to as crosslinking. This reaction of the isocyanate groups with the aldimine being hydrolyzed need not necessarily proceed via free amino groups. It will be appreciated that reactions with intermediates of the hydrolysis reaction are also possible. For example, it is conceivable that an aldimino group being hydrolyzed reacts directly with an isocyanate group in the form of a hemiaminal.

The water required for the curing reaction may either originate from the air (air humidity), or else the composition may be contacted with a water-containing component, for example by spraying, or a water-containing component can be added to the composition in the course of application.

The one-component moisture-curing composition cures on contact with moisture generally without the formation of bubbles. The curing rate can be influenced via the type and amount of one or more catalysts which may be present, via the temperature which exists in the course of curing and via the air humidity or the amount of water added.

In a further embodiment, the curable composition has two components and comprises at least one polyisocyanate P2 and either at least one aldimine of the formula (I) or at least one aldimino-containing compound AV.

In the present document, a "two-component" composition is understood to mean a curable composition in which the constituents of the composition are present in two separate components which are stored in separate containers and which are each storage-stable. The two components are referred to as component K1 and as component K2. Only just before or during the application of the composition are the two components mixed with one another, and the mixed composition then cures, the curing under some circumstances proceeding or being completed only through the action of moisture and/or heat.

The aldimine of the formula (I) or the aldimino-containing compound AV may be a constituent of component K1, or a constituent of component K2, or a constituent of both components K1 and K2.

Component K1 of the two-component polyurethane composition comprises at least one polyisocyanate P2 as the polyisocyanate.

A suitable polyisocyanate P2 is a polyisocyanate PI2 in the form of a monomeric diisocyanate or of an oligomer of a monomeric diisocyanate or of a derivative of a monomeric diisocyanate. Suitable polyisocyanates PI2 are the abovementioned polyisocyanates PI, preference being given to technical forms of oligomeric IPDI, HDI and TDI, and especially PMDI and room temperature liquid forms of MDI.

A further suitable polyisocyanate P2 is a polyurethane polymer PUP as described above.

Suitable polyisocyanates P2 are finally also mixtures of polyurethane polymers PUP and polyisocyanates PI2, especially mixtures of at least one MDI-based polyurethane polymer PUP and at least one monomeric and/or polymeric MDI.

In addition to the polyisocyanate P2, component K1 may comprise at least one aldimine of the formula (I) or at least one aldimino-containing compound AV. In this case, the polyisocyanate P2 preferably has aliphatic isocyanate groups. Component K1, however, preferably comprises neither an aldimine of the formula (I) nor an aldimino-containing compound AV.

Component K2 of the two-component polyurethane composition comprises at least one constituent reactive toward isocyanate groups, especially selected from the group comprising water, polyamines, polyols, amino alcohols, polythiols or blocked amines. Component K2 preferably comprises at least one blocked amine in the form of at least one aldimine of the formula (I) or in the form of at least one aldimino-containing compound AV. Suitable for this purpose are the aldimines of the formula (I) described above in detail, or the preferred embodiments thereof, especially aldimines of the formula (I) with the sum of the indices m+n of 2 or 3, and aldimino-containing compounds AV which are free of isocyanate groups and have a functionality in relation to the reaction with isocyanate groups of 2 or 3. Particular preference is given to aldimines of the formulae (Ia) and (Ib), and aldimino-containing compounds AV1 of the formula (X) with the index u=0 and the index v=2 or 3.

Suitable polyamines in component K2 are primary aliphatic polyamines as already described as amines B2 of the formula (IIIb); secondary aliphatic polyamines, for example N,N'-dibutylethylenediamine; N,N'-di-tert-butylethylenediamine, N,N'-diethyl-1,6-hexanediamine, 1-(1-methylethylamino)-3-(1-methylethylaminomethyl)-3,5,5-trimethylcyclohexane (Jefflink® 754 from Huntsman), N4-cyclohexyl-2-methyl-N2-(2-methylpropyl)-2,4-pentanediamine, N,N'-dialkyl-1,3-xylylenediamine, bis(4-(N-alkylamino)cyclohexyl)methane, N-alkylated polyetheramines, for example the Jeffamine® products SD-231, SD-401, SD-404 and SD-2001 (all from Huntsman), products from the Michael-type addition of the primary aliphatic polyamines mentioned by way of example onto Michael acceptors such as maleic diesters, fumaric diesters, citraconic diesters, acrylic esters, methacrylic esters, cinnamic esters, itaconic diesters, vinylphosphonic diesters, aryl vinylsulfonates, vinyl sulfones, vinyl nitriles, 1-nitroethylenes or Knoevenagel condensation products, for example those formed from malonic diesters and aldehydes such as formaldehyde, acetaldehyde or benzaldehyde; aliphatic polyamines with primary and secondary amino groups, for example N-butyl-1,6-hexanediamine; primary and/or secondary aromatic polyamines, for example m- and p-phenylenediamine, 4,4'-diaminodiphenylmethane (MDA), 3,3'-dichloro-4,4'-diaminodiphenylmethane (MOCA), mixtures of 3,5-dimethylthio-2,4- and -2,6-toluylene-diamine (obtainable as Ethacure® 300 from Albemarle), mixtures of 3,5-diethyl-2,4- and -2,6-toluylenediamine (DETDA), 3,3',5,5'-tetraethyl-4,4'-diaminodiphenyl-methane (M-DEA), 3,3',5,5'-tetraethyl-2,2'-dichloro-4,4'-diaminodiphenylmethane (M-CDEA), 3,3'-diisopropyl-5,5'-dimethyl-4,4'-diaminodiphenylmethane (M-MIPA), 3,3',5,5'-tetraisopropyl-4,4'-diaminodiphenylmethane (M-DIPA), 4,4'-diaminodiphenyl sulfone (DDS), 4-amino-N-(4-aminophenyl)benzenesulfonamide, 5,5'-methylene-dianthranilic acid, dimethyl (5,5'-methylene-dianthranilate), 1,3-propylenebis(4-aminobenzoate), 1,4-butylenebis(4-aminobenzoate), polytetramethylene oxide bis(4-aminobenzoate) (obtainable as Versalink® from Air Products), 1,2-bis(2-aminophenylthio)ethane, N,N'-dialkyl-p-phenylenediamine, N,N'-dialkyl-4,4'-diaminodiphenylmethane, 2-methylpropyl (4-chloro-3,5-diaminobenzoate), and tert-butyl (4-chloro-3,5-diaminobenzoate); and polyamines having more than three amino groups.

Suitable polyols in component K2 are the same polyols as have already been mentioned as suitable for preparing a polyurethane polymer PUP, and those low molecular weight di- or polyhydric alcohols as mentioned above as suitable for additional use in the preparation of a polyurethane polymer PUP.

Suitable amino alcohols in component K2 are compounds which have at least one primary or secondary amino group and at least one hydroxyl group, for example the aliphatic hydroxylamines as already mentioned above as suitable amines B1 for preparing the aldimines of the formula (I), and additionally, for example, diethanolamine, 2-(methylamino)ethanol, 2-(ethylamino)-ethanol, 2-(butylamino)ethanol and 2-(cyclohexyl-amino)ethanol.

Suitable polythiols in component K2 are, for example, liquid mercapto-terminated polymers known under the Thiokol® brand name, for example the products LP-3, LP-33, LP-980, LP-23, LP-55, LP-56, LP-12, LP-31, LP-32 and LP-2 (Morton Thiokol; obtainable, for example, from SPI Supplies, USA, or from Toray Fine Chemicals, Japan), and polyesters of thiocarboxylic acids, for example pentaerythritol tetramercaptoacetate, trimethylolpropane trimercaptoacetate, glycol dimercaptoacetate, pentaerythritol tetra(3-mercaptopropionate), trimethylolpropane tri(3-mercaptopropionate) and glycol di(3-mercaptopropionate).

In addition to the aldimines of the formula (I) and the aldimino-containing compounds AV, it is also possible to use further blocked amines as a constituent of component K2, especially ketimines, oxazolidines, enamines and other aldimines. Such other aldimines are obtainable proceeding from aldehydes other than the abovementioned aldehydes ALD of the formula (IV), for example isobutyraldehyde or the products from the esterification of carboxylic acids, such as especially lauric acid, with 3-hydroxypivalaldehyde. Ketimines are obtainable, for example, from the reaction of the above-described amines B of the formula (III) with ketones. Suitable oxazolidines are especially polyoxazolidines, for example OZ hardener (Bayer). Suitable enamines are obtainable, for example, from the reaction of amines having a plurality of secondary amino groups with aliphatic or cycloaliphatic aldehydes or ketones which have at least one hydrogen atom on the carbon atom in the a position to the carbonyl group.

Component K2 optionally comprises water, especially the amount of water required to hydrolyze the aldimino groups and other blocked amino groups, or a portion thereof.

Component K2 preferably further comprises at least one catalyst in the form of an organometallic compound and/or of a tertiary amine and/or of an acid, especially of an organic carboxylic or sulfonic acid.

The two-component polyurethane composition optionally comprises further constituents. In the case of component K1, these are especially the assistants and additives as mentioned above for a one-component moisture-curing composition. In the case of component K2, in addition to the former, further assistants and additives are also possible, which are storable together with free isocyanate groups only briefly, if at all. In particular, these are catalysts such as: compounds of zinc, manganese, iron, chromium, cobalt, copper, nickel, molybdenum, lead, cadmium, mercury, antimony, vanadium, titanium, zirconium or potassium, such as zinc(II) acetate, zinc (II) 2-ethylhexanoate, zinc(II) laurate, zinc(II) oleate, zinc(II) naphthenate, zinc(II) acetylacetonate, zinc(II) salicylate, manganese(II) 2-ethylhexanoate, iron(III) 2-ethylhexanoate, iron(III) acetylacetonate, chromium(III) 2-ethylhexanoate, cobalt(II) naphthenate, cobalt(II) 2-ethylhexanoate, copper (II) 2-ethyl-hexanoate, nickel(II) naphthenate, phenylmercuric neodecanoate, lead(II) acetate, lead(II) 2-ethylhexanoate, lead(II) neodecanoate, lead(II) acetylacetonate, aluminum lactate, aluminum oleate, aluminum(III) acetylacetonate, diisopropoxytitanium bis(ethylacetoacetate), dibutoxytitanium bis(ethyl-acetoacetate), dibutoxytitanium bis(acetylacetonate), potassium acetate, potassium octanoate; tertiary amine compounds, such as triethylamine, tributylamine, N-ethyldiisopropylamine, N,N,N',N'-tetramethylethylenediamine, pentamethyldiethylenetriamine and higher homologs thereof, N,N,N',N'-tetramethylpropylene-diamine, pentamethyldipropylenetriamine and higher homologs thereof, N,N,N',N'-tetramethyl-1,3-butane-diamine, N,N,N',N'-tetramethyl-1,6-hexanediamine, bis(dimethylamino)methane, N,N-dimethylbenzylamine, N,N-dimethylcyclohexylamine, N-methyldicyclohexylamine, N,N-dimethylhexadecylamine, bis(N,N-diethylaminoethyl)adipate, N,N-dimethyl-2-phenylethylamine, tris(3-dimethylaminopropyl)amine, 1,4-diazabicyclo[2.2.2]-octane (DABCO), 1,8-diazabicyclo[5.4.0]undec-7-ene (DBU), 1,5-diazabicyclo[4.3.0]non-5-ene (DBN), N-methylmorpholine, N-ethylmorpholine, N-cocomorpholine, N,N'-dimethylpiperazine, N-methyl-N'-dimethylaminoethylpiperazine, bis (dimethylaminoethyl)piperazine, 1,3,5-tris(dimethylaminopropyl)hexahydrotriazine or bis(2-dimethylaminoethyl)ether; aromatic nitrogen compounds, such as 4-dimethylaminopyridine, N-methylimidazole, N-vinylimidazole or 1,2-dimethylimidazole; amidines and guanidines, such as 1,1,3,3-tetramethylguanidine; tertiary amine compounds containing active hydrogen atoms, such as triethanolamine, triisopropanolamine, N-methyldiethanolamine, N,N-dimethylethanolamine, 3-(dimethylamino)propyldiisopropanolamine, bis(3-(dimethylamino)propyl)isopropanolamine, bis(3-dimethyl-aminopropyl)amine, 3-(dimethylamino)propylurea, Mannich bases of phenols such as 2,4,6-tris(dimethyl-aminomethyl)phenol or 2,4,6-tris(3-(dimethylamino)-propylaminomethyl)phenol, imidazoles, for example N-hydroxypropylimidazole, N-(3-aminopropyl)imidazole, and alkoxylation and polyalkoxylation products of these compounds, for example dimethylaminoethoxyethanol; organic ammonium compounds, such as benzyltrimethylammonium hydroxide, or alkoxylated tertiary amines; so-called "delayed action" catalysts, which are modifications of known metal or amine catalysts, such as reaction products of tertiary amines and carboxylic acids or phenols, for example of 1,4-diazabicyclo[2.2.2]octane or DBU and formic acid or acetic acid; and combinations of the compounds mentioned, especially of metal compounds and tertiary amines.

The two components K1 and K2 are prepared separately from one another, for component K1 with the exclusion of moisture. The two components K1 and K2 are storage-stable separately from one another, i.e. they can each be stored in a suitable package or arrangement, for example a drum, a pouch, a bucket, a cartridge or a bottle, over several months up to one year and longer before use, without their particular properties changing to a degree relevant for the use thereof.

For use of the two-component polyurethane composition, the two components K1 and K2 are mixed with one another. It should be ensured that the mixing ratio is selected such that the constituents reactive toward isocyanate groups are in a suitable ratio to the isocyanate groups of component K1. More particularly, the ratio is 0.1 to 1.1, preferably 0.5 to 0.95, more preferably 0.6 to 0.9, equivalents of the sum of the hydroxyl groups, amino groups, mercapto groups and protected amino groups present per equivalent of isocyanate groups, protected amino groups in the form of oxazolidino groups being counted double. In the course of curing, excess isocyanate groups react with moisture, especially with air humidity.

The two components K1 and K2 are mixed by a suitable process, for example by means of a static mixer. The mixing can be effected continuously or batchwise. The mixed composition is then applied to a substrate, optionally by means of a suitable application aid. In doing so, it has to be ensured that not too much time passes between the mixing of the components and the application, since excessive prereaction of the constituents of the mixed composition before application can disrupt the function of the cured composition, for example by virtue of the adhesion to the substrate being built up only in an inadequate or retarded manner. The maximum period of time within which the mixed composition should be applied is referred to as "pot life".

After the mixing of components K1 and K2, the curing commences. The aldimino groups begin to react with the isocyanate groups in the manner already described as soon as they come into contact with water. Either the water is already present in the mixed composition—by virtue of it having been a constituent of component K2, or by virtue of it having been added to the composition before or during the mixing of the two components K1 and K2—or the water diffuses into the mixed composition in the form of air humidity. In the latter case, the aldimino groups react with the isocyanate groups from the outside inward, parallel to the penetration of the moisture from the air into the composition. As already described, the reaction of the isocyanate groups with the aldimino groups being hydrolyzed need not necessarily proceed via free amino groups, but can also proceed via intermediates of the hydrolysis reaction. In the same way, the reactive groups of further blocked amines which may be present in the composition are released. In addition, after the mixing of components K1 and K2, the hydroxyl, mercapto and amino groups present in the composition react with the isocyanate groups. Excess isocyanate groups react directly with water in particular. As a result of these reactions, the mixed composition crosslinks and ultimately cures to give a solid material.

The curing of the curable compositions described generally proceeds without the formation of bubbles, even at high curing rate. The curing rate can be influenced via the type and amount of one or more catalysts which may be present, via the temperature which exists in the course of curing and via the air humidity or the amount of water added.

As already mentioned above, the tertiary amino group of the aldimines of the formula (I), or of the aldimino-containing compounds AV, may have a catalytic effect on the reaction of the isocyanate groups and therefore accelerate the curing. It is advantageous in this context that the basicity thereof is comparatively low, since strongly basic tertiary amines can disrupt the acid-catalyzed hydrolysis of the aldimino groups and/or accelerate the direct reaction of the isocyanate groups, especially with water, to an excessive degree, which can be disruptive for the curing. The accelerating action of the tertiary amino groups on the reaction of the isocyanate groups, especially on the reaction of the isocyanate groups remaining after the depletion of the aldimino groups, with water present is additionally promoted by the fact that the tertiary amino group is localized in the aldehyde moiety of the aldimine. The hydrolysis of the aldimino groups releases aldehydes ALD of the formula (IV) containing the tertiary amino group. Owing to their relatively small size, the aldehydes ALD have quite good mobility in the composition as it cures, which potentially increases the catalytic effect thereof on further isocyanate groups. The aldehydes ALD released remain substantially in the cured composition, have excellent compatibility there, do not tend to sweat out and have only a minor plasticizing effect, which is often very advantageous. A further advantage of the compositions described lies in the comparatively low odor of the aldimines described and of the aldehydes ALD released in the curing. As a result, the compositions have only low odor before, during and after the curing.

As a result of these reactions with water, especially in the form of air humidity, the composition crosslinks and ultimately cures to give a solid material.

Preferred applications of the curable compositions described are one- or two-component adhesives, sealants, potting compositions, coatings, floor coverings, paints, coating materials, primers or foams. Some applications will be described briefly hereinafter, which, however, is in no way intended to restrict another use of these compositions.

In a preferred embodiment, one of the curable compositions described is used as an elastic adhesive or sealant. In this application, the content of the polyisocyanate, preferably in the form of a polyurethane polymer having isocyanate groups, is especially in the range of 10-80% by weight, preferably of 15-70% by weight, based on the overall composition.

In addition, the curable composition in the application as an elastic adhesive or sealant advantageously comprises at least one filler, which influences both the rheological properties of the uncured composition and the mechanical properties and the surface characteristics of the cured composition. Suitable fillers are the inorganic and organic fillers already mentioned. Preference is given to carbon black, calcium carbonates, calcined kaolins, finely divided silicas, PVC powder and flame-retardant fillers such as hydrates or hydroxides, especially aluminum hydroxide. The filler content is especially in the range from 10 to 70% by weight, preferably from 20 to 60% by weight, based on the overall composition. It may be advantageous to use a mixture of different fillers.

In addition, the curable composition in the application as an elastic adhesive or sealant advantageously comprises at least one of the catalysts already mentioned, which accelerate the hydrolysis of the aldimino groups or the reaction of the isocyanate groups. Especially suitable are mixtures of organic acids and of an organometallic compound or a metal complex, of an organic acid and of a compound containing tertiary amino groups, or mixtures of organic acids, of an organometallic compound or a metal complex, and of a compound containing tertiary amino groups. A typical content of catalysts is typically 0.005 to 2% by weight, based on the overall composition, it being clear to the person skilled in the art what use amounts are advisable for which catalysts.

An elastic adhesive or sealant may be present in the form of a one-component or two-component composition, each of which is produced and applied in the manner already described. A one-component elastic adhesive or sealant preferably comprises at least one polyurethane polymer PUP1.

Suitable applications of a one- or two-component elastic adhesive are, for example, the bonding of components in construction or civil engineering and in the manufacture or repair of industrial goods or consumer goods, especially of windows, domestic appliances or modes of transport such as water or land vehicles, preferably automobiles, buses, trucks, trains or ships, and the bonding of articles in the furniture, textile or packaging industry; or the sealing of joints, seams or cavities in industrial manufacture or repair, or in construction or civil engineering.

Suitable applications of a one- or two-component elastic sealant are, for example, the sealing of a built structure, especially joints in construction or civil engineering, or the sealing of part of a built structure, for example of a window or of a floor, or the sealing of an industrial good, for example of a domestic appliance or of a mode of transport, especially a water or land vehicle, or of a part thereof.

In a further preferred embodiment, one of the curable compositions described is used as an elastic coating. In this application, the polyisocyanate content is especially in the range of 10-80% by weight, preferably of 15-70% by weight, based on the overall composition.

In addition, the curable composition in the application as an elastic coating advantageously comprises at least one filler, which influences both the rheological properties of the uncured composition and the mechanical properties, and the surface characteristics of the cured composition. Suitable fillers are the inorganic and organic fillers already mentioned. Preference is given to calcium carbonates, barite and quartz flours, and flame-retardant fillers such as hydrates or hydroxides, especially aluminum hydroxide. The filler content is especially in the range from 10 to 70% by weight, preferably from 20 to 60% by weight, based on the overall composition. It may be advantageous to use a mixture of different fillers.

In addition, the curable composition in the application as an elastic coating advantageously comprises at least one catalyst. Suitable catalysts are the same catalysts in the same amounts as already mentioned as suitable constituents of elastic adhesives and sealants.

In addition, the curable composition in the application as an elastic coating advantageously comprises at least another of the assistants and additives already mentioned, especially selected from the group comprising pigments, leveling agents, defoamers and stabilizers.

An elastic coating may be present in the form of a one-component or two-component composition, each of which is produced and applied in the manner already described.

The composition advantageously has a liquid consistency with good leveling properties. As a result, it can be applied in a simple manner as a self-leveling coating to predominantly flat surfaces, for example as floor covering.

A finished floor covering is frequently a construction composed of several different layers. A typical construction may begin, for example, with a primer which has the task of preparing the substrate for the elastic polyurethane coating. Subsequently, for example, the composition described is applied as an elastic layer, which application can be effected in one or more steps according to the nature of the substrate and desired layer thickness. Typically, a layer thickness of 0.5 to 3 mm, especially 0.5 to 2 mm, is applied per layer. Finally, a seal can subsequently be applied, which also influences the surface nature of the floor covering in a thin layer, for example in a thickness of a few micrometers to a few tenths of a millimeter. This may be a transparent or pigmented seal.

In the case of a two-component coating, the two components K1 and K2 are mixed with one another in a suitable manner before application and the mixed composition is applied within the pot life.

The curable composition is applied in the form of an elastic coating typically by pouring it onto the substrate to be coated and is distributed homogeneously in the liquid state with the aid, for example, of a coating knife or of a notched trowel. In addition, the material can be leveled and deaerated with a spiked roller. However, machine application is also possible, for example in the form of a spray application.

A suitable substrate to which the composition is typically applied is, for example, concrete, cement, asphalt, steel, wood, ceramic or a plastic, which substrate can be pretreated by cleaning, brushing or sandblasting, and/or may have a primer. Examples of useful primers include adhesion promoter solutions.

The elastic coating described can advantageously be used in the interior or exterior of a building or of a built structure, for example as a floor covering for interiors such as offices, industrial halls, gymnasiums or chill rooms, or outdoors for balconies, terraces, bridges, parking decks, or sports grounds and playgrounds.

In a further preferred embodiment, one of the curable compositions described is used as a paint, coating material or primer. In this application, the polyisocyanate is preferably either a polyisocyanate PI1 or a polyisocyanate PI2.

A "primer" is understood in the present document to mean a composition which is suitable as an undercoat and comprises, as well as nonreactive volatile substances and optionally solid additives, at least one polymer and/or at least one substance with reactive groups, and which is capable of curing, when applied to a substrate, to give a solid film with good adhesion in a layer thickness of typically at least 5 µm, the curing resulting either solely through the evaporation of the nonreactive volatile substances, for example solvents or water, or through a chemical reaction, or through a combination of these factors, and which builds up good adhesion to a layer applied subsequently, for example an adhesive or sealant.

In the application as a paint, coating material or primer, preference is given to one-component compositions, which, for reasons of storage stability, preferably comprise exclusively polyisocyanates with aliphatic isocyanate groups.

In addition, the curable composition in the application as a paint, coating material or primer advantageously comprises at least one further assistant and additive among those already mentioned, especially at least one solvent. Suitable solvents are, for example, ketones such as acetone, methyl ethyl ketone, methyl isobutyl ketone, diisobutyl ketone and mesityl oxide, and cyclic ketones such as cyclohexanone and methylcyclohexanone; esters such as methyl acetate, ethyl acetate, propyl acetate, butyl acetate, tert-butyl acetate, formates, propionates or malonates; ethers such as ketone ethers, ester ethers and dialkyl ethers such as diisopropyl ether, diethyl ether, dibutyl ether, methyl tert-butyl ether, diethylene glycol diethyl ether and ethylene glycol diethyl ether; aliphatic and aromatic hydrocarbons such as toluene, xylene, heptane, octane, and mineral oil fractions such as naphtha, white spirit, petroleum ether or benzine; halogenated hydrocarbons such as methylene chloride; and N-alkylated lactams, for example N-methylpyrrolidone, N-cyclohexylpyrrolidone or N-dodecylpyrrolidone. The solvents content is especially in the range from 10 to 90% by weight, preferably 20 to 80% by weight, based on the overall composition.

In addition, the curable composition in the application as a paint, coating material or primer may comprise further constituents, especially triisocyanates such as tris(4-isocyanatophenyl)methane and tris(4-isocyanato-phenyl)thiophosphate; aminosilanes, for example 3-aminopropyltrimethoxysilane, N-(2-aminoethyl)-3-aminopropyltrimethoxysilane, bis[3-(trimethoxysilyl)-propyl]amine, 3-aminopropyldimethoxymethylsilane, 3-amino-2-methylpropyltrimethoxysilane, N-(2-amino-ethyl)-3-aminopropyldimethoxymethylsilane, 4-aminobutyltrimethoxysilane, 4-aminobutyldimethoxymethylsilane, 4-amino-3-methylbutyltrimethoxysilane, 4-amino-3,3-dimethylbutyltrimethoxysilane, 4-amino-3,3-dimethylbutyldimethoxymethylsilane, [3-(2-aminoethyl-amino)propyl]trimethoxysilane (=4,7,10-triazadecyl-trimethoxysilane), 2-aminoethyltrimethoxysilane, 2-aminoethyldimethoxymethylsilane, aminomethyl-trimethoxysilane, aminomethyldimethoxymethylsilane, aminomethylmethoxydimethylsilane, 7-amino-4-oxaheptyl-dimethoxymethylsilane, N-(methyl)-3-aminopropyl-trimethoxysilane, N-(n-butyl)-3-aminopropyltrimethoxy-silane; tris[3-(trimethoxysilyl)propyl]amine, 1,3,5-tris[3-trimethoxysilyl)propyl]-1,3,5-triazine-2,4,6(1H,3H,5H)-trioneurea (=tris(3-(trimethoxysilyl)-propyl)isocyanurate) and the corresponding analogs in which the methoxy group is replaced by an ethoxy or isopropoxy group; mercaptosilanes, for example 3-mercaptopropyltrimethoxysilane or 3-mercaptopropyl-triethoxysilane, epoxysilanes, for example 3-glycidyl-oxypropyltrimethoxysilane, 3-glycidyloxypropyl-triethoxysilane; ureidoalkylsilanes and adducts of amino- and/or mercaptosilanes with epoxides or epoxysilanes, for example with 3-glycidyloxypropyl-silanes; titanates, preferably those which have at least one substituent bonded to the titanium atom via an oxygen-titanium bond, especially an alkoxy group, sulfonate group, carboxylate group, dialkyl phosphate group, dialkyl pyrophosphate group or acetylacetonate group, where a plurality of substituents may all be the same or mixed with one another. Examples of suitable titanates are the Kenrich Petrochemicals products available under the trade name Ken-React® KR TTS, KR 7, KR 9S, KR 12, KR 26S, KR 33DS, KR 38S, KR 39DS, KR44, KR 1345, KR 138S, KR 158FS, KR212, KR 238S, KR 262ES, KR 138D, KR 158D, KR238T, KR 238M, KR238A, KR238J, KR262A, LICA 38J, KR 55, LICA 01, LICA 09, LICA 12, LICA 38, LICA 44, LICA 97, LICA 99, KR OPPR and KR OPP2, and the DuPont products available under the trade name Tyzor® ET, TPT, NPT, BTM, AA, AA-75, AA-95, AA-105, TE, ETAM and OGT.

The paints, coating materials or primers described advantageously comprise at least one adhesion promoter in the form of the silanes or titanates already mentioned.

The paints, coating materials or primers described advantageously comprise at least one of the catalysts already mentioned.

The paints, coating materials or primers described are typically applied to the substrate by means of a brush, felt, cloth, sponge or spray gun. This application can be effected manually or automatically, especially by means of robots.

The paints, coating materials or primers described react on contact with water, especially in the form of air humidity, in the manner already described, in the course of which further components reactive with water, for example compounds containing titanate or silane groups, likewise react with water. In addition, on completion of application of the coating, any volatile solvents present therein begin to evaporate. As a consequence, a solid film with good adhesion forms on the substrate. The layer thickness thereof is advantageously about 5-100 µm, especially 10-50 µm.

A primer is advantageously used as a tiecoat for polymer compositions in the form of adhesives, sealants or coatings, for example floor coverings, especially polymer compositions based on polyurethanes with isocyanate groups and/or silane groups.

A further aspect of the present invention relates to a process for bonding a substrate S1 to a substrate S2, which comprises the steps of:
 i) applying an above-described curable composition to a substrate S1;
 ii) contacting the composition applied with a substrate S2 within the open time of the composition;
 or
 i') applying an above-described composition to a substrate S1 and to a substrate S2;
 ii') contacting the compositions applied with one another within the open time of the composition;
 the substrate S2 consisting of the same material as, or a different material than, the substrate S1.

A further aspect of the present invention relates to a process for sealing. This comprises the step of:
 i″) applying an above-described curable composition between a substrate S1 and a substrate S2, such that the composition is in contact with the substrate S1 and the substrate S2;
 the substrate S2 consisting of the same material as, or a different material than, the substrate S1.

The sealant is typically injected into a joint.

A further aspect of the present invention relates to a process for coating a substrate S1. This comprises the step of:
 i‴) applying an above-described curable composition to a substrate S1 within the open time of the composition.

In these three processes, suitable substrates S1 and/or S2 are, for example, inorganic substrates such as glass, glass ceramic, concrete, mortar, brick, tile, gypsum and natural stone such as granite or marble; metals or alloys such as aluminum, steel, nonferrous metals, galvanized metals; organic substrates such as leather, fabrics, paper, wood, resin-bound woodbase materials, resin-textile composite materials, plastics such as polyvinyl chloride (rigid and flexible PVC), acrylonitrile-butadiene-styrene copolymers (ABS), SMC (sheet molding composites), polycarbonate (PC), polyamide (PA), polyesters, PMMA, polyesters, epoxy resins, polyurethanes (PU), polyoxymethylene (POM), polyolefins (PO), especially surface-plasma-, -corona- or -flame-treated polyethylene (PE) or polypropylene (PP), ethylene/propylene copolymers (EPM) and ethylene/propylene-diene terpolymers (EPDM); coated substrates such as powder-coated metals or alloys; and paints and coating materials, especially automotive coating materials.

The substrates can be pretreated before the application of the composition if required. Such pretreatments include especially physical and/or chemical cleaning processes, for example grinding, sandblasting, brushing or the like, or treatment with detergents or solvents, or the application of an adhesion promoter, of an adhesion promoter solution or of a primer.

In the case of a two-component composition, the two components K1 and K2 are mixed with one another just before the application.

In the case of a heat-curing composition, the composition applied is then baked onto the adhesive bond, the seal or the coating, by heating it to a suitable temperature.

The curable composition can be applied within a broad temperature spectrum. For example, the composition can be applied at room temperature, as is typical of an elastic adhesive or a sealant. The composition can, however, also be applied at lower or else higher temperatures. The latter is advantageous especially when the composition comprises high-viscosity or meltable components as are typically present in meltable adhesives, for example warm-melt adhesives or hot-melt adhesives. The application temperatures for warm-melts are, for example, in the range from 40 to 80° C., in the case of hot-melts in the range from 85 to 200° C.

The described processes for adhesive bonding, sealing or coating—or the use of one of the compositions described as a one- or two-component adhesive, sealant, potting composition, coating, floor covering, paint, coating material, primer or foam—give rise to an article.

This article is especially a built structure, especially a built structure in construction or civil engineering, or an industrial good or a consumer good, especially a window, a domestic appliance, or a mode of transport, especially a water or land vehicle, preferably an automobile, a bus, a truck, a train or a ship, or an installable component of a mode of transport, or an article in the furniture, textile or packaging industry.

EXAMPLES

1. Description of the Test Methods

The viscosity was measured on a Physica UM thermostated cone-plate viscometer (cone diameter 20 mm, cone angle 1°, cone tip-plate distance 0.05 mm, shear rate 10 to 1000 $s^{-1}$).

The amine content, i.e. the total content of free amino groups and blocked amino groups (aldimino groups) in the compounds prepared, was determined by titrimetric means (with 0.1N $HClO_4$ in glacial acetic acid, against crystal violet) and is always reported in mmol N/g.

The $pK_a$ for the conjugated acid of a Mannich base was determined approximately using the half-neutralization potential in the potentiometric titration of approx. 1 mmol of Mannich base in 50 ml of water or, where not possible, in 50 ml of 1/1 water/isopropanol, with 0.1N HCl, and the values measured in water/isopropanol were converted to the expected values in pure water using reference substances.

Infrared spectra were measured on a Perkin-Elmer 1600 FT-IR instrument, solid substances as KBr pressings in a direct beam, liquids and oils as undiluted films (if necessary by dissolving the substance in $CH_2Cl_2$ and evaporating the solvent) on a horizontal ATR analysis unit with a ZnSe crystal; the absorption bands are reported in wavenumbers ($cm^{-1}$) (measurement window: 4000-650 $cm^{-1}$); the addition sh indicates a band which appears as a shoulder, the addition br a broad band.

$^1$H NMR spectra were measured on a Bruker DPX-300 spectrometer at 300.13 MHz; the chemical shifts δ are reported in ppm relative to tetramethylsilane (TMS), coupling constants J are reported in Hz; true and pseudo coupling patterns were not distinguished.

2. Preparation of Aldehydes 2,2-Dimethyl-3-(N-pyrrolidino)propanal

A round-bottom flask under a nitrogen atmosphere was initially charged with 51.0 g (0.72 mol) of pyrrolidine which were dissolved in 100 ml of abs. ethanol. With good stirring and ice cooling, 40.6 g (0.40 mol) of 96% sulfuric acid were slowly added dropwise from a dropping funnel, in the course of which it was ensured that the temperature of the suspension which formed did not rise above 50° C. Then 23.8 g (0.79 mol) of paraformaldehyde and 54.5 g (0.76 mol) of isobutyraldehyde were added, and the reaction mixture was stirred under reflux in an oil bath at 120° C. over 2 hours. The clear reaction mixture was cooled to room temperature, taken up in 500 ml of 10% sodium sulfite solution and basified with 10N NaOH. The organic phase was removed in a separating funnel and put aside. The aqueous phase was extracted twice with 50 ml each time of ethyl acetate, and the extracts were dried over anhydrous $Na_2SO_4$ and concentrated. The organic phases were combined and fractionated under reduced pressure. Yield: 79.2 g (71% of theory) as a colorless, clear liquid with an amine-like odor, an amine content of 6.34 mmol N/g and a viscosity of 3 mPa·s at 20° C.

Alternative Preparation:

A round-bottom flask under a nitrogen atmosphere was initially charged with 59.8 g (0.72 mol) of 36% aqueous formaldehyde and 53.8 g (0.75 mol) of isobutyraldehyde. With good stirring and ice cooling, 51.0 g (0.72 mol) of pyrrolidine were slowly added dropwise from a dropping funnel, in the course of which it was ensured that the temperature of the reaction mixture did not rise above 20° C. On completion of addition, the mixture was left to stir at room temperature for one hour. The turbid, colorless reaction mixture which formed was stirred under reflux in an oil bath at 100° C. over 18 hours and cooled to room temperature, and the phases were separated in a separating funnel. The organic phase was fractionated under reduced pressure without further processing. The product distilled at a top temperature of 80° C. and a pressure of 17 mbar. Yield: 95.9 g (86% of theory) of colorless, clear liquid with an amine content of 6.34 mmol N/g.

$pK_a$≈9.2.

IR: 2962, 2928sh, 2873, 2782, 2692 (CHO), 1724 (C=O), 1460, 1400, 1362, 1351, 1327, 1293, 1238, 1202, 1141, 1114, 1059, 1036, 1002, 965, 916, 906, 874, 774.

$^1$H NMR ($CDCl_3$, 300 K): δ 9.56 (s, 1H, CHO), 2.63 (s, 2H, $NCH_2C(CH_3)_2$), 2.49 (m, 4H, $NCH_2CH_2^{cycl.}$), 1.71 (m, 4H, $NCH_2CH_2^{cycl.}$), 1.08 (s, 6H, $CH_2C(CH_3)_2$).

2,2-Dimethyl-3-(N-morpholino)propanal

A round-bottom flask under a nitrogen atmosphere was initially charged with 83.1 g (1.00 mol) of 36% aqueous formaldehyde and 75.0 g (1.04 mol) of isobutyraldehyde. With good stirring and ice cooling, 87.1 g (1.00 mol) of morpholine were slowly added dropwise from a dropping funnel, in the course of which it was ensured that the temperature of the reaction mixture, did not rise above 20° C. On completion of addition, the mixture was stirred at room temperature for one hour. The clear, colorless reaction mixture which formed was stirred under reflux in an oil bath at 100° C. over 18 hours and cooled to room temperature, and the phases were separated in a separating funnel. The organic phase was fractionated under reduced pressure without further processing. The product distilled at a top temperature of 97° C. and a pressure of 14 mbar. Yield: 145.5 g (85% of theory) as a colorless, clear, almost odorless liquid with an amine content of 5.72 mmol N/g and a viscosity of 11 mPa·s at 20° C.

$pK_a$≈6.3.

IR: 2958, 2981, 2850, 2803, 2695 (CHO), 1979, 1722 (C=O), 1455, 1402, 1374, 1361, 1319, 1280, 1268, 1206, 1137, 1115, 1070, 1035, 1015, 951, 906, 864, 801, 774.

$^1$H NMR ($CDCl_3$, 300 K): δ 9.55 (s, 1H, CHO), 3.63 (d, J=9.4, 4H, $OCH_2^{cycl.}$), 2.47 (s, 2H, $NCH_2C(CH_3)_2$), 2.44 (m, 4H, $NCH_2^{cycl.}$), 1.08 (s, 6H, $CH_2C(CH_3)_2$).

2,2-Dimethyl-3-(N-(2,6-dimethyl)morpholino)propanal

Under the same conditions as for the preparation of 2,2-dimethyl-3-(N-morpholino)propanal, 41.7 g (0.50 mol) of 36% aqueous formaldehyde were reacted with 37.9 g (0.53 mol) of isobutyraldehyde and 57.6 g (0.50 mol) of 2,6-dimethylmorpholine (BASF; isomer mixture), and worked up. The product distilled at a top temperature of 104° C. and a pressure of 20 mbar. Yield: 80.8 g (81% of theory) as a colorless, clear liquid with a slight amine-like odor, which had an amine content of 4.99 mmol N/g.

$pK_a \approx 5.9$.

IR: 2970, 2933, 2868, 2799, 2771sh, 2727, 2700sh (CHO), 2627, 1724 (C=O), 1456, 1403, 1373, 1362sh, 1320, 1281, 1240, 1216sh, 1178, 1144, 1077, 1042, 1003, 967, 946, 916, 887sh, 879, 860, 837, 799, 773.

$^1$H NMR (CDCl$_3$, 300 K): δ 9.55 (s, 1H, CHO), 3.59 (ddq, J=10.0/6.3/2.3, 2H, OCH$_2$CH$_3$), 2.57 (qd, J=10.5/2.1, 2×1H of CH(CH$_3$)—CH$_2$N), 2.44 (s, 2H, NCH$_2$C(CH$_3$)$_2$), 1.86 (dd, J=11.4/10.0, 2×1H of CH(CH$_3$)—CH$_2$N), 1.11 (d, J=6.3, 6H, OCHCH$_3$), 1.06 (s, 6H, NCH$_2$C(CH$_3$)$_2$).

2,2-Dimethyl-3-(N-benzylmethylamino)propanal

Under the same conditions as for the preparation of 2,2-dimethyl-3-(N-morpholino)propanal, 39.2 g (0.47 mol) of 36% aqueous formaldehyde were reacted with 35.6 g (0.49 mol) of isobutyraldehyde and 57.0 g (0.47 mol) of N-benzylmethylamine, and worked up. The product distilled at a top temperature of 74° C. and a pressure of 4·10$^{-2}$ mbar. Yield: 80.6 g (83% of theory) as a colorless, clear and almost odorless liquid which had an amine content of 4.83 mmol N/g.

$pK_a \approx 7.2$.

IR: 3084, 3060, 3026, 2962, 2928, 2870, 2840, 2784, 2700 (CHO), 1950, 1876, 1808, 1722 (C=O), 1654, 1602, 1584, 1542, 1494, 1452, 1420, 1398, 1362, 1316, 1290, 1256, 1172, 1118, 1074, 1038, 1024, 1002, 976, 948, 916, 910, 880, 856, 826, 774, 738, 698, 670.

$^1$H NMR (CDCl$_3$, 300 K): δ 9.52 (s, 1H, CHO), 7.33-7.20 (m, 5H, Ph-H), 3.51 (s, 2H, Ph-CH$_2$—N), 2.59 (s, 2H, NCH$_2$C(CH$_3$)$_2$), 2.16 (s, 3H, NCH$_3$), 1.07 (s, 6H, NCH$_2$C(CH$_3$)$_2$).

2,2-Dimethyl-3-(N-benzylisopropylamino)propanal

Under the same conditions as for the preparation of 2,2-dimethyl-3-(N-morpholino)propanal, 28.0 g (0.34 mol) of 36% aqueous formaldehyde were reacted with 25.4 g (0.35 mol) of isobutyraldehyde and 50.0 g (0.34 mol) of N-benzylisopropylamine, and worked up. The product distilled at a top temperature of 100° C. and a pressure of 4·10$^{-2}$ mbar. Yield: 48.6 g (62% of theory) as a pale yellow, clear and almost odorless liquid which had an amine content of 4.28 mmol N/g.

$pK_a \approx 6.6$.

IR: 3084, 3060, 3026, 2962, 2929, 2869, 2823sh, 2806, 2699 (CHO), 1948, 1869, 1722 (C=O), 1602, 1584, 1540, 1494, 1460, 1452, 1398, 1385, 1362, 1320, 1252, 1234, 1207, 1164, 1118, 1093, 1074, 1056, 1027, 1003, 965, 906, 877, 826, 772, 730, 697, 668.

$^1$H NMR (CDCl$_3$, 300 K): δ 9.39 (s, 1H, CHO), 7.32-7.17 (m, 5H, Ph-H), 3.53 (s, 2H, Ph-CH$_2$—N), 2.73 (sept., J=6.6, 1H, NCH(CH$_3$)$_2$), 2.59 (s, 2H, NCH$_2$C(CH$_3$)$_2$), 1.00 (s, 6H, NCH$_2$C(CH$_3$)$_2$), 2.73 (d, J=6.6, 6H, NCH(CH$_3$)$_2$).

2,2-Dimethyl-3-(N-cyclohexylmethylamino)propanal

Under the same conditions as for the preparation of 2,2-dimethyl-3-(N-morpholino)propanal, 36.8 g (0.44 mol) of 36% aqueous formaldehyde were reacted with 33.4 g (0.46 mol) of isobutyraldehyde and 50.0 g (0.44 mol) of N-cyclohexylmethylamine, and worked up. The product distilled at a top temperature of 69° C. and a pressure of 4·10$^{-2}$ mbar. Yield: 65.8 g (76% of theory) as a colorless, clear liquid smelling of amine, which had an amine content of 4.94 mmol N/g.

$pK_a \approx 8.4$.

IR: 2925, 2851, 2796, 2685 (CHO), 1723 (C=O), 1464, 1450, 1422, 1396, 1376, 1381, 1344, 1319sh, 1262, 1200, 1177, 1143, 1110, 1072, 1057sh, 1045, 1025, 1004, 987, 960, 916, 890, 878, 859, 836, 784, 772.

$^1$H NMR (CDCl$_3$, 300 K): δ 9.55 (s, 1H, CHO), 2.55 (s, 2H, NCH$_2$C(CH$_3$)$_2$), 2.22 (m, 1H, NCH$^{cycl.}$), 2.20 (s, 3H, NCH$_3$), 1.74 (m, 4 Cy-H), 1.60 (m, 1 Cy-H), 1.28-1.08 (m, 5 Cy-H), 1.06 (s, 6H, CH$_2$C(CH$_3$)$_2$).

N-(2,2-Dimethyl-3-oxopropyl)-N-methylpyrrolidinium iodide

Under a nitrogen atmosphere, 1.18 g (7.5 mmol) of 2,2-dimethyl-3-(N-pyrrolidino)propanal and 1.06 g (7.5 mmol) of methyl iodide were weighed into a pill bottle which was closed and upturned repeatedly. The mixture became turbid immediately; after a few minutes, a white precipitate began to collect at the base of the bottle. The pill bottle was left to stand at room temperature. After 90 minutes, the entire contents were permeated with snow-white crystals.

IR (KBr pressing): 3042, 3002, 2982, 2958, 2890, 2874, 2838, 2734, 1754, 1720 (C=O), 1682, 1478, 1466, 1450, 1436, 1424, 1400, 1382, 1364, 1344, 1310, 1276, 1234, 1182, 1166, 1150, 1108, 1058, 1032, 1000, 974, 944, 916, 878, 820, 768, 732.

$^1$H NMR (D$_2$O, 300 K): δ 9.65 (s, 1H, CHO), 3.81 (s, 2H, NCH$_2$C(CH$_3$)$_2$), 3.69 and 3.53 (2×m, 2×2H, NCH$_2$CH$_2^{cycl.}$), 2.93 (s, 3H, NCH$_3$), 2.22 (m, 4H, NCH$_2$CH$_2^{cycl.}$), 1.34 (s, 6H, CH$_2$C(CH$_3$)$_2$).

N-(2,2-Dimethyl-3-oxopropyl)-N-methylmorpholinium iodide

Under a nitrogen atmosphere, 1.03 g (5.9 mmol) of 2,2-dimethyl-3-(N-morpholino)propanal and 0.83 g (5.9 mmol) of methyl iodide were weighed into a pill bottle which was closed and upturned repeatedly. The mixture became turbid within 10 seconds; after a few minutes, a white precipitate began to collect at the base of the bottle. The pill bottle was left to stand at room temperature for one hour and then heated to 60° C. After 2 hours, the entire contents were permeated with snow-white crystals.

IR (KBr pressing): 3018, 2976, 2958, 2872, 2812, 2724, 1768sh, 1722 (C=O), 1685, 1476, 1462, 1420, 1400, 1384, 1370, 1312, 1280, 1248, 1220, 1176, 1144, 1120, 1082, 1066, 1039, 1016, 988, 952, 914, 900, 884, 868, 812, 772.

$^1$H NMR (D$_2$O, 300 K): δ 9.64 (s, 1H, CHO), 4.06 (m, 4H, OCH$_2^{cycl.}$) 3.87 (s, 2H, NCH$_2$C(CH$_3$)$_2$), 3.72 (m, 4H, NCH$_2^{cycl.}$), 3.21 (s, 3H, NCH$_3$), 1.37 (s, 6H, CH$_2$C(CH$_3$)$_2$).

3. Preparation of Aldimines

Example 1

Aldimine A-1

A round-bottom flask under a nitrogen atmosphere was initially charged with 23.3 g of 1,6-hexamethylene-diamine (70% in water; amine content 12.16 mmol N/g). With vigorous stirring, 47.0 g of 2,2-dimethyl-3-(N-morpholino)propanal were added from a dropping funnel.

Then the volatile constituents were removed under reduced pressure (10 mbar, 80° C.). Yield: 57.2 g of a clear, colorless oil with an amine content of 10.10 mmol N/g and a viscosity of 45 mPa·s at 20° C. IR: 2961, 2926, 2872, 2858, 2804sh, 2779, 1665 (C=N), 1459, 1446sh, 1392, 1360, 1338, 1292, 1239, 1199, 1191, 1139, 1116, 1060, 1032, 1001, 964, 937, 905, 875, 727.

$^1$H NMR (CDCl$_3$, 300 K): δ 7.55 (t, J=1.2, 2H, CH=N), 3.34 (txd, J=1.2/7.1, 4H, CH=N—CH$_2$), 2.49 (m, 12H, $^{cycl.}$CH$_2$CH$_2$NCH$_2$C(CH$_3$)), 1.71 (m, 8H, $^{cycl.}$CH$_2$CH$_2$NCH$_2$C(CH$_3$)), 1.56 (m, 4H, CH=N—CH$_2$CH$_2$), 1.29 (m, 4H, CH=N—CH$_2$CH$_2$CH$_2$), 1.07 (s, 12H, CH$_2$C(CH$_3$)$_2$).

Example 2

Aldimine A-2

Under the same conditions as described in example 1, 31.8 g of 1,6-hexamethylenediamine (70% in water; amine content 12.16 mmol N/g) were reacted with 71.0 g of 2,2-dimethyl-3-(N-morpholino)propanal. Yield: 86.3 g of a clear, colorless oil with an amine content of 9.19 mmol N/g and a viscosity of 145 mPa·s at 20° C. IR: 2954, 2926, 2849, 2805, 2762sh, 2687, 1980, 1665 (C=N), 1454, 1395, 1375, 1358, 1332, 1317, 1282, 1267, 1204, 1135, 1117, 1070, 1036, 1012, 944, 933, 882, 864, 802, 776sh, 728.

$^1$H NMR (CDCl$_3$, 300 K): δ 7.53 (t, J=1.2, 2H, CH=N), 3.64 (d, J=9.3, 8H, OCH$_2$$^{cycl.}$), 3.34 (m, 4H, CH=N—CH$_2$), 2.46 (m, 8H, NCH$_2$$^{cycl.}$), 2.34 (s, 4H, NCH$_2$C(CH$_3$)$_2$), 1.57 (m, 4H, CH=N—CH$_2$CH$_2$), 1.28 (m, 4H, CH=N—CH$_2$CH$_2$CH$_2$), 1.06 (s, 12H, CH$_2$C(CH$_3$)$_2$).

Example 3

Aldimine A-3

Under the same conditions as described in example 1, 13.4 g of polyetherdiamine (polyoxypropylenediamine with a mean molecular weight of approx. 240 g/mol; Jeffamine® D-230, Huntsman; amine content 8.29 mmol N/g) were reacted with 20.0 g of 2,2-dimethyl-3-(N-morpholino)propanal. Yield: 31.4 g of a clear, colorless oil with an amine content of 7.14 mmol N/g and a viscosity of 170 mPa·s at 20° C.

IR: 2961, 2926, 2887, 2850, 2803, 2763sh, 2690, 1980, 1663 (C=N), 1454, 1373, 1316, 1282, 1268, 1204, 1135sh, 1114, 1070, 1036, 1012, 1001sh, 946sh, 929, 897, 882, 864, 802, 775, 665.

$^1$H NMR (CDCl$_3$, 300 K): δ 7.57 (s, 2H, CH=N), 3.64 (m, 8H, OCH$_2$$^{cycl.}$), 3.6-3.1 (m, approx. 12H, OCH$_2$CH(CH$_3$)), 2.46 (m, 8H, NCH$_2$$^{cycl.}$), 2.34 (s, 4H, NCH$_2$C(CH$_3$)$_2$), 1.18-0.97 (m, approx. 24H, OCH$_2$CH(CH$_3$) and CH$_2$C(CH$_3$)$_2$).

Example 4

Aldimine A-4

Under the same conditions as described in example 1, 14.55 g of 1-amino-3-aminomethyl-3,5,5-trimethylcyclo-hexane (isophoronediamine or IPDA; Vestamin® IPD, Degussa; amine content 11.67 mmol N/g) were reacted with 30.00 g of 2,2-dimethyl-3-(N-morpholino)propanal. Yield: 40.9 g of a clear, colorless oil with an amine content of 8.29 mmol N/g and a viscosity of 6.8 Pa·s at 20° C.

IR: 2952, 2914, 2908, 2894, 2849, 2805, 2764sh, 1980, 1663 (C=N), 1454, 1396sh, 1377, 1361, 1352sh, 1332, 1317, 1282, 1267, 1204, 1136, 1116, 1070, 1051, 1036, 1012, 968, 928, 881, 864, 802.

$^1$H NMR (CDCl$_3$, 300 K): δ 7.61 and 7.60 (2×s, ratio approx. 3/1, 1H, CH=N [isomers]), 7.49 (2×s, ratio approx. 3/1, 1H, CH=N [isomers]), 3.64 (m, 8H, OCH$_2$$^{cycl.}$), 3.30 (m, 1H, CH=N—CH$^{ncycl.}$) 3.12 and 3.01 (2×d, J=11.1, 2H, CH=N—CH$_2$$^{cycl.}$) 2.47 (m, 8H, NCH$_2$$^{cycl.}$), 2.34 (s, 4H, NCH$_2$C(CH$_3$)$_2$), 1.53-0.85 (m, 27H, CH$_2$$^{cycl.}$ and CH$_3$).

Example 5

Aldimine A-5

Under the same conditions as described in example 1, 6.25 g of 1-amino-3-aminomethyl-3,5,5-trimethylcyclo-hexane (isophoronediamine or IPDA; Vestamin® IPD, Degussa; amine content 11.67 mmol N/g) were reacted with 15.00 g of 2,2-dimethyl-3-(N-(2,6-dimethyl)morpholino)propanal. Yield: 19.7 g of a clear, colorless oil with an amine content of 7.33 mmol N/g and a viscosity of 10.5 Pa·s at 20° C.

IR: 2968, 2952, 2930, 2907, 2862, 2808, 2769sh, 2731, 2624, 1727, 1664 (C=N), 1456, 1396sh, 1374, 1363, 1320, 1280, 1248, 1230, 1216, 1178, 1144, 1082, 1040, 1000, 968, 939, 916, 878, 864, 838, 803, 774.

$^1$H NMR (CDCl$_3$, 300 K): δ 7.61 and 7.48 (2×m, 2×1H, CH=N), 3.62 (m, 4H, OCHCH$_3$), 3.31 (s, approx. 0.5H, CH=N—CH$_2$C$^{cycl.}$ [isomer]), 3.28 (m, 1H, CH=N—CH$^{cycl.}$) 3.11 and 3.01 (2×d, J=11.1, approx. 1.5H, CH=N—CH$_2$C$^{cycl.}$ [isomer]), 2.62 (d, J=10.0, 4H of NCH$_2$$^{cycl.}$) 2.32 and 2.31 (2×s, 4H, NCH$_2$C(CH$_3$)$_2$), 1.89 and 1.81 (2×d, J=10.0, 4H of NCH$_2$$^{cycl.}$), 1.6-0.8 (m, 39H, CH$_2$$^{cycl.}$ and all CH$_3$).

Example 6

Aldimine A-6

Under the same conditions as described in example 1, 6.07 g of 1-amino-3-aminomethyl-3,5,5-trimethylcyclo-hexane (isophoronediamine or IPDA; Vestamin® IPD, Degussa; amine content 11.67 mmol N/g) were reacted with 15.00 g of 2,2-dimethyl-3-(N-benzylmethylamino)-propanal. Yield: 19.7 g of a clear, colorless oil with an amine content of 7.24 mmol N/g and a viscosity of 2.8 Pa·s at 20° C.

IR: 3084, 3060, 3026, 2948, 2916, 2864, 2838, 2806, 2782, 2708, 1944, 1871, 1807, 1726, 1664 (C=N), 1602, 1585, 1541, 1494, 1452, 1418, 1386, 1377, 1362, 1322, 1260, 1249sh, 1203sh, 1188, 1168, 1120, 1074, 1036, 1026, 1000, 974, 939sh, 904, 890, 858, 824, 736, 696, 670.

$^1$H NMR (CDCl$_3$, 300 K): δ 7.63 and 7.50 (2×s, ratio approx. 3/1, 1H, CH=N [isomers]), 7.49 (m, 1H, CH=N), 7.34-7.18 (m, 10 Ph-H), 3.52 and 3.51 (2×s, 2×2H, PhCH$_2$N), 3.30 (s, approx. 0.5H, CH=N—CH$_2$C$^{cycl.}$ [isomer]), 3.27 (m, 1H, CH=N—CH$^{cycl.}$) 3.10 and 2.99 (2×d, J=11.1, approx. 1.5H, CH=N—CH$_2$C$^{cycl.}$ [isomer]), 2.47 and 2.46 (2×s, 2×2H, NCH$_2$C(CH$_3$)$_2$), 2.17 and 2.16 (2×s, 2×2H, NCH$_3$), 1.6-0.8 (m, 27H, CH$_2$$^{cycl.}$ and all C—CH$_3$).

Example 7

Aldimine A-7

Under the same conditions as described in example 1, 5.34 g of 1-amino-3-aminomethyl-3,5,5-trimethylcyclo-hexane (isophoronediamine or IPDA; Vestamin® IPD, Degussa;

amine content 11.67 mmol N/g) were reacted with 15.00 g of 2,2-dimethyl-3-(N-benzylisopropyl-amino)propanal. Yield: 19.2 g of a clear, pale yellow honey with an amine content of 6.56 mmol N/g and a viscosity of 150 Pa·s at 20° C.

IR: 3082, 3060, 3024, 2958, 2922, 2864, 2816, 2710, 1944, 1872, 1805, 1662 (C=N), 1602, 1585, 1494, 1460, 1452sh, 1386, 1362, 1320, 1299, 1240, 1205sh, 1164, 1116, 1092, 1074, 1054, 1026, 998, 966, 940, 890, 845, 826, 774, 728, 696.

$^1$H NMR (CDCl$_3$, 300 K): δ 7.56 and 7.53 (2×s, ratio approx. 3/1, 1H, CH=N [isomers]), 7.41 (m, 1H, CH=N), 7.34-7.14 (m, 10 Ph-H), 3.59 and 3.57 (2×s, 2×2H, PhCH$_2$N), 3.18 (m, 1H, CH=N—CH$^{cycl.}$), 2.98 and 2.89 (2×d, J=11.0, 2H, CH=N—CH$_2$C$^{cycl.}$), 2.77 (m, 2H, NCH(CH$_3$)$_2$), 2.44 (s, 4H, NCH$_2$C(CH$_3$)$_2$), 1.6-0.8 (m, 39H, CH$_2^{cycl.}$ and all CH$_3$).

Example 8

Aldimine A-8

Under the same conditions as described in example 1, 6.31 g of 1-amino-3-aminomethyl-3,5,5-trimethylcyclo-hexane (isophoronediamine or IPDA; Vestamin® IPD, Degussa; amine content 11.67 mmol N/g) were reacted with 15.00 g of 2,2-dimethyl-3-(N-cyclohexylmethyl-amino)propanal. Yield: 19.6 g of a clear, colorless honey with an amine content of 7.38 mmol N/g and a viscosity of 28 Pa·s at 20° C.

IR: 2924, 2850, 2807, 1726, 1664 (C=N), 1462sh, 1450, 1378, 1362, 1345sh, 1315sh, 1260, 1200, 1176, 1140, 1116, 1103sh, 1071sh, 1044, 1026, 1001sh, 986, 971sh, 940sh, 917, 890, 860, 836, 785.

$^1$H NMR (CDCl$_3$, 300 K): δ 7.64 and 7.62 (2×s, ratio approx. 3/1, 1H, CH=N [isomers]), 7.50 (m, 1H, CH=N), 3.33 (s, approx. 0.5H, CH=N—CH$_2$C$^{cycl.}$ [isomer]), 3.28 (m, 1H, CH=N—CH$_2$C$^{cycl.}$), 3.13 and 3.01 (2×d, J=11.1, approx. 1.5H, CH=N—CH$_2$C$^{cycl.}$[isomer]), 2.40 (s, 4H, NCH$_2$C(CH$_3$)$_2$), 2.23 (m, 8H, N(CH$_3$)CH$^{cycl.}$), 1.74 (m, 8 Cy-H), 1.59 (m, 2 Cy-H), 1.4-0.9 (m, 37H, Cy-H and all C—CH$_3$).

Example 9

Aldimine A-9

Under the same conditions as described in example 1, 9.05 g of 2-(2-aminoethoxy)ethanol (DGA; Diglycolamine® Agent, Huntsman; amine content 9.39 mmol N/g) were reacted with 15.00 g of 2,2-dimethyl-3-(N-morpholino)propanal. Yield: 22.5 g of a clear, colorless oil with an amine content of 7.61 mmol N/g and a viscosity of 130 mPa·s at 20° C.

IR: 3415br (OH), 2953, 2919, 2887, 2850, 2805, 1665 (C=N), 1454, 1397, 1376, 1358, 1335, 1318, 1282, 1268, 1228br, 1206, 1115, 1068, 1036, 1012, 949, 927, 883, 863, 802.

$^1$H NMR (CDCl$_3$, 300 K): δ 7.63 (t, J=1.3, 1H, CH=N), 3.75-3.55 (m, 12H, OCH$_2^{cycl.}$ and HOCH$_2$CH$_2$OCH$_2$CH$_2$N=CH), 2.47 (m, 4H, NCH$_2^{cycl.}$), 2.43 (br s, 1H, OH), 2.36 (s, 2H, NCH$_2$C(CH$_3$)$_2$), 1.07 (S, 6H, CH$_2$C(CH$_3$)$_2$).

Example 10

Aldimine A-10

Under the same conditions as described in example 1, 17.38 g of N-cyclohexyl-1,3-propanediamine (BASF; amine content 12.84 mmol N/g) were reacted with 20.00 g of 2,2-dimethyl-3-(N-morpholino)propanal. Yield: 35.3 g of a clear, colorless oil with an amine content of 9.56 mmol N/g and a viscosity of 52 mPa·s at 20° C.

IR: 3304br (NH), 2952sh, 2924, 2849, 2808, 2687, 1726, 1664 (C=N), 1450, 1396, 1376sh, 1360, 1349sh, 1332, 1317, 1282, 1267, 1204, 1134, 1116, 1070, 1036, 1012, 932br, 886, 864, 846, 802, 735br.

Example 11

Aldimine A-11

In a small bulb flask, 2.15 g (7.1 mmol) of N-(2,2-dimethyl-3-oxopropyl)-N-methylpyrrolidinium iodide were dissolved under a nitrogen atmosphere in approx. 2 ml of water and the solution was admixed while stirring with 0.58 g (3.5 mmol) of 1,6-hexamethylenediamine (70% in water; amine content 12.16 mmol N/g). Subsequently, the resulting clear, colorless solution was heated in an oil bath and the volatile constituents were removed under reduced pressure (10 mbar, 80° C.). This gave a pale yellow, clear, glass-like product.

Alternative Preparation:

Under a nitrogen atmosphere, 1.00 g of aldimine A-1 was weighed, and weighed with 0.73 g (5.1 mmol) of methyl iodide into a pill bottle which was closed and upturned repeatedly. The mixture immediately became slightly turbid; after a few minutes, a precipitate in the form of a pale yellow oil began to collect at the base of the bottle. The pill bottle was left to stand at room temperature for one hour and then heated to 60° C. After 2 hours, the entire contents had solidified to a pale yellow, glassy oil.

IR: 2962, 2928, 2852, 2834sh, 2780sh, 1724 (C=O), 1664 (C=N), 1460, 1386, 1366, 1342, 1306, 1262, 1222, 1168, 1142, 1114, 1098, 1042, 1002, 970, 942, 928, 904, 890, 824, 789, 730.

$^1$H NMR (D$_2$O, 300 K): δ 7.88 (s, 2H, CH=N), 3.68 and 3.51 (2×m, 8H and 4H, $^{cycl.}$CH$_2$CH$_2$N(CH$_3$)CH$_2$C(CH$_3$)$_2$) 3.48 (t, J=7.0, 4H, CH=N—CH$_2$), 2.97 (s, 6H, NCH$_3$), 2.20 (br m, 8H, $^{cycl.}$CH$_2$CH$_2$N), 1.59 (m, 4H, CH=N—CH$_2$CH$_2$), 1.31 (m, 16H, CH=N—CH$_2$CH$_2$CH$_2$ and CH$_2$C(CH$_3$)$_2$).

Comparative Example 12

Aldimine A-12

A round-bottom flask under a nitrogen atmosphere was initially charged with 50.9 g (0.18 mol) of distilled 2,2-dimethyl-3-lauroyloxypropanal. With vigorous stirring, 10.0 g (0.17 mol of N) of 1,6-hexamethylenediamine (BASF; amine content 17.04 mmol N/g) were slowly added from a heated dropping funnel, in the course of which the mixture heated up and became increasingly turbid. Thereafter, the volatile constituents were removed under reduced pressure (10 mbar, 80° C.). Yield: 57.7 g of a clear, pale yellow oil with an amine content of 2.94 mmol N/g.

Comparative Example 13

Aldimine A-13

Under the same conditions as described in example 12, 74.3 g (0.26 mol) of distilled 2,2-dimethyl-3-lauroyloxypropanal were reacted with 30.0 g (0.25 mol of N) of polyetherdiamine (polyoxypropylenediamine with a mean molecular weight of approx. 240 g/mol; Jeffamine® D-230, Huntsman; amine content 8.29 mmol N/g). Yield: 99.5 g of a clear, pale yellow oil with an amine content of 2.50 mmol N/g.

Comparative Example 14

Aldimine A-14

Under the same conditions as described in example 12, 55.0 g (0.19 mol) of distilled 2,2-dimethyl-3-lauroyloxypropanal were reacted with 15.6 g (0.18 mol of N) of 1-amino-3-aminomethyl-3,5,5-trimethylcyclohexane (isophoronediamine or IPDA; Vestamin® IPD, Degussa; amine content 11.67 mmol N/g). Yield: 67.1 g of a clear, colorless oil with an amine content of 2.73 mmol N/g.

4. Preparation of a Compound AV1

Example 15

Aldimine A-15

In a first stage, 590 g of Acclaim® 4200 N polyol (polypropylene oxide diol, OH number 28.5 mg KOH/g; Bayer), 1180 g of Caradol® MD34-02 polyol (polypropylene oxide-polyethylene oxide triol, OH number 35.0 mg KOH/g; Shell) and 230 g of isophorone diisocyanate (IPDI; Vestanat® IPDI, Degussa) were converted by a known method at 80° C. to an NCO-terminated polyurethane polymer with a content, determined by titrimetric means, of free isocyanate groups of 2.1% by weight and a viscosity at 20° C. of 22 Pa·s.

1.31 g (5.0 mmol) of aldimine A-9 from example 9 were added at room temperature to 10.00 g of this polyurethane polymer (5.0 mequiv. of NCO), and the mixture was mixed intimately by means of a centrifugal mixer (SpeedMixer™ DAC 150, FlackTek Inc.) and then heated at 60° C. After 24 hours, the NCO band in the FT-IR spectrum (at 2265 cm$^{-1}$) was no longer detectable. This gave a clear, homogeneous and odorless liquid with an amine content of 0.44 mmol N/g and a viscosity at 20° C. of 110 Pa·s.

IR: 3340br (NH), 2967, 2929, 2893sh, 2864, 1720 (C=O), 1666 (C=N), 1529, 1454, 1372, 1344, 1299, 1282, 1239, 1094, 1013, 925, 908sh, 865, 835, 775, 660.

5. Preparation of Curable Compositions

Examples 16 to 20 and Comparative Example 21

In a screwtop polypropylene beaker, the polyurethane polymer 1, the preparation of which is described below, was mixed by means of a centrifugal mixer (SpeedMixer™ DAC 150, FlackTek Inc.; 1 min. at 2500 rpm) with an aldimine and with catalysts to give a homogeneous material, and the material thus obtained was immediately transferred into an internally coated aluminum tube which was sealed airtight. The aldimines used and the catalyst types are listed in parts by weight in table 1 for each of the examples.

The polyurethane polymer 1 was prepared as follows:

590 g of Acclaim® 4200 N polyol (polypropylene oxide diol, OH number 28.5 mg KOH/g; Bayer), 1180 g of Caradol® MD34-02 polyol (polypropylene oxide-polyethylene oxide triol, OH number 35.0 mg KOH/g; Shell) and 230 g of isophorone diisocyanate (IPDI; Vestanat® IPDI, Degussa) were converted by a known method at 80° C. to an NCO-terminated polyurethane polymer with a content, determined by titrimetric means, of free isocyanate groups of 2.1% by weight and a viscosity at 20° C. of 22 Pa·s.

The ratio between the isocyanate groups and the blocked amino groups for all examples is 1.0/0.7.

TABLE 1

Composition of examples 16 to 20 and of comparative example 21.

| | Example | | | | | |
|---|---|---|---|---|---|---|
| | 16 | 17 | 18 | 19 | 20 | 21 (comp.) |
| Polyurethane polymer 1 | 50.0 | 50.0 | 50.0 | 50.0 | 50.0 | 50.0 |
| Aldimine | A-4, 4.21 | A-5, 4.79 | A-6, 4.89 | A-7, 5.40 | A-8, 4.74 | — |
| Acid catalyst$^a$ | 0.05 | 0.05 | 0.05 | 0.05 | 0.05 | — |
| Tin catalyst$^b$ | 0.05 | 0.05 | 0.05 | 0.05 | 0.05 | 0.05 |

$^a$Salicylic acid.
$^b$5% by weight of dibutyltin dilaurate in diisodecyl phthalate.

The compositions thus obtained were tested for storage stability, skin formation time and for mechanical properties after curing.

The storage stability was determined via the change in viscosity during storage under hot conditions. To this end, the composition in the closed tube was stored at 60° C. in an oven and the viscosity at 20° C. was measured first after 4 hours of storage time and second after 7 days of storage time. The storage stability is calculated from the percentage increase of the second viscosity value compared to the first.

To measure the skin formation time ("tack-free time"), a small portion of the composition which had been stored at 60° C. over 4 hours was applied in a layer thickness of approx. 2 mm to cardboard, and the time taken, under standard climatic conditions (23±1° C., 50±5% relative air humidity), when the surface of the composition was tapped lightly using an LDPE pipette, for no residues to remain any longer on the pipette for the first time was determined.

To determine the mechanical properties, the main portion of the composition was used to produce films of thickness approx. 3 mm, by pouring the composition into a planar PTFE mold and curing under standard climatic conditions over 7 days. Clear, tack-free and elastic polyurethane films were obtained, which were completely free of bubbles. Dumbbells with a length of 75 mm, a central element length of 30 mm and a central element width of 4 mm were punched out of the films, and tested to DIN EN 53504 for tensile strength, elongation at break and modulus of elasticity (at extension 0.5-5%) (pulling speed: 200 mm/min).

The results of these tests are listed in table 2.

TABLE 2

Properties of examples 16 to 20 and of comparative example 21.

| | Example | | | | | |
|---|---|---|---|---|---|---|
| | 16 | 17 | 18 | 19 | 20 | 21 (comp.) |
| Viscosity after 4 h (Pa·s) | 21.8 | 21.0 | 21.5 | 23.1 | 24.5 | 19.0 |
| Viscosity after 7 d (Pa·s) | 23.6 | 21.7 | 21.7 | 23.8 | 26.5 | 19.9 |
| Viscosity increase (%)$^a$ | 8 | 3 | 1 | 3 | 8 | 5 |
| Skin formation time (min.) | 60 | 65 | 70 | 75 | 60 | >480 |

TABLE 2-continued

Properties of examples 16 to 20 and of comparative example 21.

| | Example | | | | | |
|---|---|---|---|---|---|---|
| | 16 | 17 | 18 | 19 | 20 | 21 (comp.) |
| Tensile strength (MPa) | 4.1 | 3.9 | 3.4 | 3.6 | 3.6 | n.d.[b] |
| Elongation at break (%) | 520 | 500 | 510 | 530 | 590 | n.d.[b] |
| Modulus of elasticity (MPa) | 1.7 | 1.3 | 1.3 | 1.4 | 1.2 | n.d.[b] |

[a] = ((Viscosity after 7 d/viscosity after 4 h) − 1) × 100%.
[b] Not determined.

Examples 22 to 27

Elastic 1K Sealants (For Example for Dilatation Joints)

For each example, the particular constituents according to table 3 were processed in the parts by weight specified, without preceding drying, in a vacuum mixer with exclusion of moisture to give a lump-free homogeneous paste, which was immediately transferred into an internally coated aluminum cartridge which was sealed airtight.

The polyurethane polymer 1 was prepared as described in example 16.

The urea thickener was prepared as follows:

A vacuum mixer was initially charged with 3000 g of diisodecyl phthalate (DIDP; Palatinol® Z, BASF) and 480 g of 4,4'-methylenediphenyl diisocyanate (MDI; Desmodur® 44 MC L, Bayer) and heated gently. Then 270 g of monobutylamine were slowly added dropwise with vigorous stirring. The paste which formed was stirred under vacuum while cooling for a further hour.

The ratio between the isocyanate groups and the sum of the blocked amino groups (oxazolidino groups being counted double) is 1.0/0.67 for all examples.

TABLE 3

Composition of the elastic 1K PU sealants.

| | Example | | | | | |
|---|---|---|---|---|---|---|
| | 22 | 23 | 24 (comp.) | 25 (comp.) | 26 (comp.) | 27 (comp.) |
| Polyurethane polymer 1 | 24.0 | 24.0 | 24.0 | 24.0 | 24.0 | 24.0 |
| Aldimine | A-3, 2.25 | A-4, 1.93 | A-13, 3.22 | A-14, 2.95 | — | — |
| Oxazolidine[a] | — | — | — | — | 0.99 | — |
| Plasticizer[b] | 2.15 | 2.47 | 1.18 | 1.45 | 3.41 | 4.7 |
| Chalk | 38.0 | 38.0 | 38.0 | 38.0 | 38.0 | 38.0 |
| Thickener[c] | 28.0 | 28.0 | 28.0 | 28.0 | 28.0 | 28.0 |
| Titanium dioxide | 4.5 | 4.5 | 4.5 | 4.5 | 4.5 | 4.5 |
| Epoxysilane[d] | 0.2 | 0.2 | 0.2 | 0.2 | 0.2 | 0.2 |
| Acid catalyst[e] | 0.6 | 0.6 | 0.6 | 0.6 | 0.6 | — |
| Tin catalyst[f] | 0.3 | 0.3 | 0.3 | 0.3 | 0.3 | 0.6 |

[a] OZ hardener, Bayer; amine content = 4.05 mmol/g.
[b] Diisodecyl phthalate (DIDP; Palatinol ® Z, BASF).
[c] Urea thickener.
[d] 3-Glycidoxypropyltriethoxysilane (Dynasylan ® GLYEO, Degussa).
[e] Salicylic acid (5% by weight in dioctyl adipate).
[f] Dibutyltin dilaurate (5% by weight in diisodecyl phthalate).

The sealants thus obtained were tested for skin formation time, through-curing rate, tack, staining and mechanical properties after curing.

The skin formation time was determined as described in example 16.

The through-curing rate was determined by applying the sealant by means of a cartridge gun through a round tip (orifice 10 mm) as a horizontal, free-hanging cone with a length of approx. 50 mm and a thickness in the middle of 30 mm to a piece of cardboard secured to a wall, left under standard climatic conditions for 7 days and then cut vertically down the middle, and the thickness of the cured layer was measured with a ruler.

The tack was determined by pressing the thumb onto the Shore A test specimen stored over one day or 3 days with the finger, and then it was assessed purely qualitatively how long the test specimen remained adhering to the thumb when the hand was raised (high/moderate/low/zero).

Staining was assessed on the basis of the size (large/moderate/small/none) of the grease ring which had formed one week after the application of a Shore A test specimen to a sheet of paper to which the sample had been applied fresh.

To determine mechanical properties after curing, the Shore A hardness, the tensile strength, the elongation at break and the extension stress at 100% were measured. The Shore A hardness was determined to DIN 53505 on test specimens cured under standard climatic conditions over 14 days. To test the further mechanical properties, the sealant, 2 hours after preparation, was pressed by means of a press to a film of thickness approx. 2 mm, and the film was cured under standard climatic conditions over 14 days and tested to DIN EN 53504 for tensile strength, elongation at break and extension stress at 100% (pulling speed: 200 mm/min).

The results of the tests are shown in table 4.

TABLE 4

Properties of the elastic 1K PU sealants.

| | Example | | | | | |
|---|---|---|---|---|---|---|
| | 22 | 23 | 24 (comp.) | 25 (comp.) | 26 (comp.) | 27 (comp.) |
| Skin formation time (min.) | 50 | 90 | 165 | 245 | 90 | >480 |
| Through-curing (mm) | 10 | 8 | 6 | 6 | 15 | 8* |
| Tack after 1 day | moderate | zero | high | low | high | high |
| Tack after 3 days | moderate | zero | high | zero | moderate | high |
| Staining | none | none | moderate | moderate | moderate | large |
| Shore A hardness | 28 | 36 | 21 | 31 | 35 | 27 |
| Tensile strength (MPa) | 2.7 | 3.0 | 2.5 | 2.6 | 1.4 | 1.9 |
| Elongation at break (%) | 1000 | 930 | 1040 | 1000 | 530 | 1000 |
| Extension stress at 100% extension (MPa) | 0.5 | 0.6 | 0.4 | 0.4 | 0.6 | 0.4 |

*significant bubble formation.

Example 28 and Comparative Examples 29 to 31

Elastic 1K Adhesives (For Example for Construction, Assembly)

For each example, the particular constituents according to table 5 in the parts by weight specified were processed without preceding drying in a vacuum mixer with exclusion of moisture to give a lump-free, homogeneous paste which was immediately transferred into an internally coated aluminum cartridge which was sealed airtight.

The polyurethane polymer 1 and the urea thickener were prepared as described in example 16 and in example 22 respectively.

The ratio between the isocyanate groups and the sum of the blocked amino groups (oxazolidino groups being counted double) is 1.0/0.52 for all examples.

TABLE 5

Composition of the elastic 1K PU adhesives.

| | Example | | | |
|---|---|---|---|---|
| | 28 | 29 (comp.) | 30 (comp.) | 31 (comp.) |
| Polyurethane polymer 1 | 35.0 | 35.0 | 35.0 | 35.0 |
| Aldimine | A-4, 2.73 | A-14, 4.17 | — | — |
| Oxazolidine$^a$ | — | — | 1.40 | — |
| Plasticizer$^b$ | 0.8 | 0.8 | 0.8 | 0.8 |
| Chalk | 27.0 | 27.0 | 27.0 | 27.0 |
| Thickener$^c$ | 28.27 | 26.83 | 29.60 | 31.50 |
| Titanium dioxide | 4.5 | 4.5 | 4.5 | 4.5 |
| Epoxysilane$^d$ | 0.2 | 0.2 | 0.2 | 0.2 |
| Acid catalyst$^e$ | 1.0 | 1.0 | 1.0 | — |
| Tin catalyst$^f$ | 0.5 | 0.5 | 0.5 | 1.0 |

$^a$OZ hardener, Bayer; amine content = 4.05 mmol/g.
$^b$HDI trimer (Desmodur ® N-3600, Bayer), NCO content = 23.0% by weight.
$^c$Urea thickener.
$^d$3-Glycidoxypropyltriethoxysilane (Dynasylan ® GLYEO, Degussa).
$^e$Salicylic acid (5% by weight in dioctyl adipate).
$^f$Dibutyltin dilaurate (5% by weight in diisodecyl phthalate).

The adhesives thus obtained were tested as described in example 22 for skin formation time, through-curing rate, staining and mechanical properties after curing, except that the modulus of elasticity (at 0.5-50 extension) is reported instead of the tension at 1000 extension stress. The results of the tests are shown in table 6.

TABLE 6

Properties of the elastic 1K PU adhesives.

| | Example | | | |
|---|---|---|---|---|
| | 28 | 29 (comp.) | 30 (comp.) | 31 (comp.) |
| Skin formation time (min.) | 70 | 190 | 50 | >480 |
| Through-curing (mm) | 8 | 8 | 12 | 9 |
| Staining | none | small | small | large |
| Shore A hardness | 43 | 43 | 43 | 45 |
| Tensile strength (MPa) | 2.5 | 2.2 | 1.4 | n.m.* |
| Elongation at break (%) | 620 | 640 | 320 | n.m.* |
| Modulus of elasticity (MPa) | 3.7 | 3.0 | 3.7 | n.m.* |

*not measurable owing to significant bubble formation.

Examples 32 to 37 and Comparative Examples 38 to 40

2K Potting Compositions

For each example, the particular constituents of component K2 according to table 7 were weighed in the parts by weight specified without preceding drying into a screwtop polypropylene beaker and mixed by means of a centrifugal mixer (SpeedMixer™ DAC 150, FlackTek Inc.; 2 min. at 3000 rpm) to give a homogeneous cream.

TABLE 7

Composition of the two-component PU potting compositions.

| | Example | | | | | | | | |
|---|---|---|---|---|---|---|---|---|---|
| | 32 | 33 | 34 | 35 | 36 | 37 | 38 (comp.) | 39 (comp.) | 40 (comp.) |
| Comp. K1: | | | | | | | | | |
| PMDI[a] | 30.4 | 30.8 | 29.7 | 30.2 | 32.8 | 31.8 | 29.2 | 28.9 | 29.7 |
| Comp. K2: | | | | | | | | | |
| Castor oil[b] | 22.5 | 22.5 | 22.5 | 22.5 | 22.5 | 22.5 | 22.5 | 22.5 | 22.5 |
| Dimer fatty acid diol[c] | 17.5 | 17.5 | 17.5 | 17.5 | 17.5 | 17.5 | 17.5 | 17.5 | 22.5 |
| Triol[d] | 4.75 | 4.75 | 4.75 | 4.75 | 4.75 | 4.75 | 4.75 | 4.75 | 4.75 |
| Aldimine | A-1, 5.0 | A-2, 5.0 | A-3, 5.0 | A-4, 5.0 | A-9, 5.0 | A-10, 5.0 | A-12, 5.0 | A-13, 5.0 | — |
| Acid catalyst[e] | 0.25 | 0.25 | 0.25 | 0.25 | 0.25 | 0.25 | 0.25 | 0.25 | 0.25 |
| Chalk[f] | 50.0 | 50.0 | 50.0 | 50.0 | 50.0 | 50.0 | 50.0 | 50.0 | 50.0 |

[a]Desmodur ® VKS 20 F, Bayer; NCO content = 30.0% by weight.
[b]OH number = 165 mg KOH/g.
[c]Sovermol ® 908, Cognis; OH number = 200 mg KOH/g.
[d]Desmophen ® 4011 T, Bayer; OH number = 550 mg KOH/g.
[e]Salicylic acid (5% by weight in dioctyl adipate).
[f]Omyacarb ® 5-GU, Omya.

To this were added the parts by weight of PMDI specified in table 7 as component K1, which were mixed in (30 sec. at 3000 rpm). The ratio between the isocyanate groups of component K1 and the sum of the reactive groups (hydroxyl and aldimino groups) of component K2 is always 1.1.

The two-component polyurethane potting compositions thus obtained were tested for curing rate, mechanical properties and bubble formation.

Indications of the curing rate were obtained firstly by measuring the tack-free time which was measured in the same way as the skin formation time as described in example 16. Secondly, the further course of the curing was monitored by periodically measuring the Shore D hardness to DIN 53505.

The tensile strength, elongation at break and modulus of elasticity (at 0.5-3% extension) were measured to DIN EN 53504 on cast films of a thickness of approx. 2 mm, which were cured under standard climatic conditions over 7 days (pulling speed: 10 mm/min).

TABLE 8

Properties of the two-component PU potting compositions.

| | Example | | | | | | | | |
|---|---|---|---|---|---|---|---|---|---|
| | 32 | 33 | 34 | 35 | 36 | 37 | 38 (comp.) | 39 (comp.) | 40 (comp.) |
| Freedom from tack (min.)[a] | 10 | 20 | 30 | 22 | 30 | 38 | 38 | 58 | 48 |
| Shore D after 1 day | 81 | 84 | 81 | 82 | 88 | 77 | 58 | 60 | 60 |
| Shore D after 3 days | 87 | 93 | 90 | 87 | 92 | 92 | 72 | 73 | 75 |
| Shore D after 7 days | 91 | 94 | 93 | 91 | 96 | 94 | 83 | 84 | 82 |
| Shore D heat-treated[b] | 88 | 94 | 94 | 91 | 96 | 96 | 89 | 86 | 85 |
| Tensile strength (MPa) | 21.9 | 31.2 | 23.2 | 20.2 | 32.3 | 22.7 | 11.0 | 11.0 | 8.1 |
| Elongation at break (%) | 3 | 6 | 16 | 20 | 5 | 5 | 65 | 75 | 60 |
| Modulus of elasticity (MPa) | 610 | 740 | 570 | 505 | 830 | 640 | 100 | 85 | 100 |
| Bubble formation | none | none | none | none | none | none | none | none | many |

[a]Tack-free time.
[b]4 h at 105° C. of the test specimens cured under standard climatic conditions over 7 days.

Bubble formation was assessed qualitatively by the amount of bubbles which occurred in the course of curing of a film with a layer thickness of 2 mm under standard climatic conditions.

The results of these tests are shown in table 8.

Examples 41 to 43

Semistructural 2K Adhesives

For each example, the particular constituents of component K2 according to table 9 were weighed in the parts by weight specified without preceding drying into a screwtop polypropylene beaker and mixed by means of a centrifugal mixer (SpeedMixer™ DAC 150, FlackTek Inc.; 2 min. at 3000 rpm) to give a homogeneous cream. To this were added the parts by weight of PMDI specified in table 9 as component K1, which were mixed in (30 sec. at 3000 rpm).

TABLE 9

Composition of the semistructural 2K PU adhesives.

| | Example | | |
|---|---|---|---|
| | 41 | 42 | 43 |
| Component K1: | | | |
| PMDI[a] | 25.0 | 25.4 | 25.0 |
| Component K2: | | | |
| Castor oil[b] | 22.5 | 22.4 | 22.4 |
| Dimer fatty acid diol[c] | 7.5 | — | — |
| PPG 1000[d] | 12.5 | 22.4 | 22.4 |
| Triol[e] | 2.25 | 2.25 | 2.25 |
| Aldimine | A-2, 5.0 | A-4, 5.0 | A-9, 5.0 |
| Acid catalyst[f] | 0.25 | 0.25 | 0.25 |
| Chalk[g] | 50.0 | 50.0 | 50.0 |

[a]Desmodur ® VKS 20 F, Bayer; NCO content = 30.0% by weight.
[b]OH number = 165 mg KOH/g.
[c]Sovermol ® 908, Cognis; OH number = 200 mg KOH/g.
[d]Desmophen ® 1112 BD, Bayer; OH number = 112 mg KOH/g.
[e]Desmophen ® 4011 T, Bayer; OH number = 550 mg KOH/g.
[f]Salicylic acid (5% by weight in dioctyl adipate).
[g]Omyacarb ® 5-GU, Omya.

The ratio between the isocyanate groups of component K1 and the sum of the reactive groups (hydroxyl and aldimino groups) of component K2 is always 1.1.

The two-component polyurethane adhesives thus obtained were tested as described in example 32 for curing rate, mechanical properties and bubble formation. The results of the tests are shown in table 10.

TABLE 10

Properties of the semistructural 2K PU adhesives.

| | Example | | |
|---|---|---|---|
| | 41 | 42 | 43 |
| Freedom from tack (min.)[a] | 23 | 37 | 35 |
| Shore D after 1 day | 54 | 49 | 56 |
| Shore D after 3 days | 74 | 72 | 71 |
| Shore D after 7 days | 79 | 78 | 81 |
| Shore D heat-treated[b] | 72 | 74 | 75 |
| Tensile strength (MPa) | 10.2 | 9.5 | 10.2 |
| Elongation at break (%) | 53 | 86 | 64 |
| Modulus of elasticity (MPa) | 85 | 49 | 91 |
| Bubble formation | none | none | none |

[a]Tack-free time in minutes.
[b]4 h at 105° C. of the test specimens cured under standard climatic conditions over 7 days.

Examples 44 to 45 and Comparative Example 46

Elastic 1K Coatings (For Example for Floor Covering)

For each example, the particular constituents of the coating material according to table 11 were weighed in the parts by weight specified without preceding drying into a screwtop polypropylene beaker and mixed by means of a centrifugal mixer (Speedmixer™ DAC 150, FlackTek Inc.; 1 min. at 2500 rpm), and the mixture was transferred immediately into an internally coated aluminum tube which was sealed airtight. The particular ratio between the aldimino groups and the isocyanate groups (aldimine/NCO ratio) is reported in table 11.

The polyurethane polymer 2 was prepared as follows: 1060 g of polyoxypropylenediol (Desmopheri® 1111 BD, Bayer; OH number 111.4 mg KOH/g), 650 g of polyoxypropylenediol (Desmophen® 2061 BD, Bayer; OH number 56.1 mg KOH/g), 770 g of isophorone diisocyanate (Vestanat® IPDI, Degussa) and 0.25 g of dibutyltin dilaurate were reacted at 80° C. to give an NCO-terminated polyurethane polymer with a content of free isocyanate groups of 6.8% by weight.

TABLE 11

Composition of the one-component PU coating materials.

| | Example | | |
|---|---|---|---|
| | 44 | 45 | 46 (comp.) |
| Polyurethane polymer 2 | 50.0 | 50.0 | 50.0 |
| IPDI trimer[a] | 24.0 | 24.0 | 24.0 |
| Aldimine | A-2, 21.0 | A-4, 21.0 | A-12, 21.0 |
| Acid catalyst[b] | 1.5 | 1.5 | 1.5 |
| Amine catalyst[c] | 0.75 | 0.75 | 0.75 |
| Tin catalyst[d] | 0.75 | 0.75 | 0.75 |
| Defoamer[e] | 2.0 | 2.0 | 2.0 |
| Aldimine/NCO ratio | 0.75 | 0.70 | 0.49 |

[a]45% by weight of IPDI trimer (Vestanat ® T 1890/100, Degussa; NCO content = 17.3% by weight) in xylene.
[b]Salicylic acid (5% by weight in dioctyl adipate).
[c]2,2'-Dimorpholinodiethyl ether (DABCO ® DMDEE Catalyst, Air Products).
[d]10% by weight of dibutyltin dilaurate in diisodecyl phthalate.
[e]BYK-088 (BYK-Chemie/ALTANA).

The one-component polyurethane coating materials thus obtained were tested for storage stability, skin formation time, mechanical properties, bubble formation and odor formation.

The storage stability was determined by comparing the viscosity of the coating material before and after the storage thereof at elevated temperature. To this end, the coating material was stored in the closed tube in an oven at 40° C. and the viscosity thereof was measured first 2 hours after the preparation, second after 24 days of storage time.

The skin formation time was measured as described in example 16. The mechanical properties were likewise measured as described in example 16, except that the curing rate of the Shore test specimens was 28 days, and that of the films 21 days under standard climatic conditions.

The odor formation was assessed qualitatively by smelling with the nose at a distance of 10 cm over a cured film.

The results of these tests are listed in table 12.

TABLE 12

Properties of the one-component PU coating materials.

| | Example | | |
|---|---|---|---|
| | 44 | 45 | 46 (comp.) |
| Viscosity before storage (mPa · s) | 380 | 640 | 220 |
| Viscosity after storage (mPa · s) | 780 | 1120 | 350 |
| Skin formation time (min.) | 31 | 78 | 160 |
| Shore hardness (A or D) | 87A | 55D | 69A |
| Tensile strength (MPa) | 15.9 | 23.0 | 8.8 |
| Elongation at break (%) | 350 | 260 | 310 |
| Modulus of elasticity (MPa) | 85 | 260 | 18 |
| Bubble formation | none | none | some |
| Odor formation | none | none | none |

Example 47

Elastic 2K Coatings (for Example for Floor Covering)

To prepare component K1, 64 parts by weight (PW) of polyurethane polymer 2, 32 PW of a solution of 45% by weight of IPDI trimer in xylene (Vestanat® T 1890/100, Degussa; with 17.3% by weight of NCO), 1 PW of acid catalyst (5% by weight of salicylic acid in dioctyl adipate), 0.5 PW of amine catalyst (2,2'-dimorpholinodiethyl ether, DABCO® DMDEE Catalyst, Air Products), 1 PW of tin catalyst (10% by weight of dibutyltin dilaurate in diisodecyl phthalate) and 1.5 PW of defoamer (BYK-088, BYK-Chemie/ALTANA) were weighed without preceding drying in a polypropylene cartridge and mixed by means of a centrifugal mixer (SpeedMixer™ DAC 150, FlackTek Inc., 30 sec. at 2500 rpm). To this were added 19.5 PW of the aldimine A-5 as component K2, which were mixed in (30 sec. at 2500 rpm). The ratio between the isocyanate groups of component K1 and the sum of the reactive groups (hydroxyl and aldimino groups) of component K2 is 1.1.

The polyurethane polymer 2 was prepared as described in example 44.

The two-component polyurethane coating material thus obtained was tested for tack-free time, for mechanical properties after curing and for bubble formation and odor formation.

The tack-free time was measured in the same way as the skin formation time in example 16. The mechanical properties were likewise measured as described in example 16, except that the curing time of the Shore test specimens was 28 days, and that of the films 14 days under standard climatic conditions. Bubble formation and odor formation were measured as described in example 44.

The results of these tests are shown in table 13.

TABLE 13

Properties of the two-component PU coating material.

| | Example 47 |
|---|---|
| Tack-free time (min.) | 135 |
| Shore A hardness | 87 |
| Tensile strength (MPa) | 9.5 |
| Elongation at break (%) | 370 |
| Modulus of elasticity (MPa) | 34 |
| Bubble formation | none |
| Odor formation | none |

Example 48

1K Paint (Suitable as a Coating Material or Primer)

A mixture of 1.00 g of polyurethane polymer 3, the preparation of which is described below, 0.29 g of aldimine A-4, 0.10 g of 3-glycidoxypropyltrimethoxy-silane and a spatula-tip of salicylic acid was diluted with ethyl acetate to solids content 50% by weight.

The polyurethane polymer 3 was prepared as follows:

1.00 g of polyoxypropylenediol (Desmophen® 1112 BD, Bayer; OH number 112 mg KOH/g), 4.06 g of IPDI trimer (Vestanat® T 1890/100, Degussa) and 5.06 g of ethyl acetate were converted by a known method at 60° C. to a polyurethane polymer with a content, determined by titrimetric means, of free isocyanate groups of 5.7% by weight.

A small portion of the solution obtained was applied by means of a brush in a thin layer to a glass plate which had been cleaned beforehand with heptane (float glass; from Rocholl, Schonbrunn, Germany) and left to stand under standard climatic conditions. After 30 minutes, a tack-free, shiny, transparent film with good adhesion and a completely dry surface had formed. After 3 days, the film had a pencil hardness (Wolff-Wilborn scratch hardness, measured to ISO 15184) of 6H . . . 7H. The adhesion of the film on the glass was excellent (no splintering when scratched with a pencil of 9H hardness).

A further portion of the solution was applied in the manner described to a further glass plate and left to stand under standard climatic conditions. After 30 minutes, a one-component polyurethane adhesive (SikaTack® Ultrafast, obtainable from Sika Schweiz AG) was applied in the form of a triangular bead to the film applied, and the glass plate was stored under standard climatic conditions over 7 days, in the course of which the adhesive cured. Then the adhesion of the adhesive bead on the substrate was tested by incising the bead down to just above the substrate by means of a cutter, holding the incised end by hand and then cautiously and slowly pulling or tearing it away from the substrate, peeling in the direction of the other end of the bead, in the course of which the bead was regularly incised with the cutter at right angles to the pulling direction if it threatened to tear apart. The adhesion of the bead was excellent; there was 100% tearoff in the adhesive (cohesion fracture).

The remaining, unapplied solution was storable without a significant viscosity increase in an impervious vessel over several weeks.

The invention claimed is:

1. An aldimine of the formula (I)

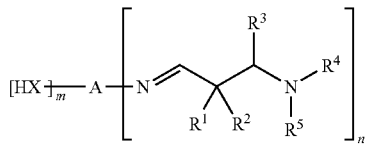
(I)

where

A is either
the radical of an amine after removal of n primary aliphatic amino groups and m HX groups, or
together with $R^7$ is an (n+2)-valent hydrocarbon radical which has 3 to 20 carbon atoms and optionally contains at least one heteroatom;

n is 1 or 2 or 3 or 4, and
m is 0 or 1 or 2 or 3 or 4,
with the proviso that m+n is 2 or 3 or 4 or 5;

$R^1$ and $R^2$ are either
each independently a monovalent hydrocarbon radical having 1 to 12 carbon atoms, or
together are a divalent hydrocarbon radical having 4 to 12 carbon atoms which is part of an optionally substituted carbocyclic ring having 5 to 8 carbon atoms;

$R^3$ is a hydrogen atom or an alkyl group or an arylalkyl group or an alkoxycarbonyl group;

$R^4$ and $R^5$ are either
each independently a monovalent aliphatic, cycloaliphatic or arylaliphatic radical which has 1 to 20 carbon atoms and is free of hydroxyl groups and optionally contains heteroatoms in the form of ether oxygen or tertiary amine nitrogen, or
together are a divalent aliphatic radical which has 3 to 20 carbon atoms and is part of an optionally substituted heterocyclic ring having 5 to 8 ring atoms, this ring being free of hydroxyl groups and, as well as the nitrogen atom, optionally containing further heteroatoms in the form of ether oxygen or tertiary amine nitrogen; and X is O or S or N—$R^6$ or N—$R^7$, where $R^6$ is either
a monovalent hydrocarbon radical which has 1 to 20 carbon atoms and optionally has at least one carboxylic ester, nitrile, nitro, phosphonic ester, sulfone or sulfonic ester group, or
a substituent of the formula (II)

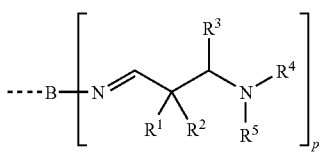
(II)

where
p is 0 or an integer from 1 to 10 000, and
B is a (p+1)-valent hydrocarbon radical which optionally contains ether oxygen, tertiary amine nitrogen, hydroxyl groups, secondary amino groups or mercapto groups;

wherein, when m=0 and n=3, $R^4$ and $R^5$ do not contain any tertiary amine nitrogen.

2. An aldimine of the formula (I) as claimed in claim 1, wherein m=1 or 2 or 3 or 4.

3. An aldimine of the formula (I) as claimed in claim 2, wherein it is an aldimine of the formula (Ia)

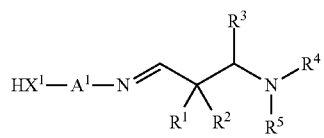
(Ia)

where
$A^1$ does not have any active hydrogen or any primary amino groups and is either
a divalent hydrocarbon radical which has 2 to 20 carbon atoms and optionally contains at least one heteroatom, or
together with $R^9$ is a trivalent hydrocarbon radical which has 3 to 20 carbon atoms and optionally contains at least one heteroatom;

$X^1$ is O or S or N—$R^8$ or N—$R^9$, where $R^8$ is either
a monovalent hydrocarbon radical which has 1 to 20 carbon atoms and optionally has at least one carboxylic ester, nitrile, nitro, phosphonic ester, sulfone or sulfonic ester group, or
a substituent of the formula (IIa)

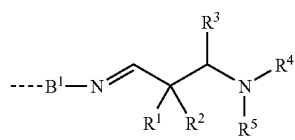
(IIa)

where $B^1$ is a divalent hydrocarbon radical which has 2 to 12 carbon atoms and optionally has ether oxygen or tertiary amine nitrogen; and $R^9$ together with $A^1$ is a trivalent hydrocarbon radical which has 3 to 20 carbon atoms and optionally contains at least one heteroatom.

4. An aldimine of the formula (I) as claimed in claim 1, wherein m=0.

5. An aldimine of the formula (I) as claimed in claim 4, wherein it is an aldimine of the formula (Ib)

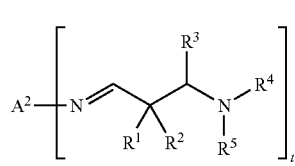
(Ib)

where
t is 2 or 3; and
$A^2$ is the radical of a polyamine with t primary amino groups after removal of t primary amino groups and does not contain any active hydrogen.

6. An aldimine of the formula (I) as claimed in claim 1, wherein $R^1$ and $R^2$ are each methyl.

7. An aldimine of the formula (I) as claimed in claim 1, wherein R³ is hydrogen.

8. An aldimine of the formula (I) as claimed in claim 1, wherein R⁴ and R⁵ are either
   each independently ethyl, propyl, isopropyl, butyl, 2-ethylhexyl, cyclohexyl or benzyl, or
   together—including the nitrogen atom—a ring, which ring is optionally substituted.

9. An aldimine of the formula (I) as claimed in claim 1, wherein A is a radical of an amine selected from the group consisting of N-methyl-1,2-ethanediamine, N-ethyl-1,2-ethanediamine, N-cyclohexyl-1,2-ethanediamine, N-methyl-1,3-propanediamine, N-ethyl-1,3-propanediamine, N-butyl-1,3-propanediamine, N-cyclohexyl-1,3-propanediamine, 4-aminomethylpiperidine, 3-(4-aminobutyl)piperidine, diethylenetriamine (DETA), dipropylenetriamine (DPTA), bishexamethylenetriamine (BHMT), N-cocoalkyl-1,3-propanediamine, N-oleyl-1,3-propanediamine, N-soyaalkyl-1,3-propanediamine and N-tallowalkyl-1,3-propanediamine, 5-amino-1-pentanol, 6-amino-1-hexanol, 4-(2-aminoethyl)-2-hydroxyethylbenzene, 3-aminomethyl-3,5,5-trimethylcyclohexanol, 2-(2-aminoethoxy)ethanol, triethylene glycol monoamine, 3-(2-hydroxyethoxy)propylamine, 3-(2-(2-hydroxyethoxy)ethoxy)propylamine, and 3-(6-hydroxyhexyloxy)propylamine.

10. An aldimine of the formula (I) as claimed in claim 1, wherein A is a radical of an amine selected from the group consisting of 1,6-hexamethylenediamine, 1,5-diamino-2-methylpentane (MPMD), 1,3-pentanediamine (DAMP), 1-amino-3-aminomethyl-3,5,5-trimethylcyclohexane (=isophoronediamine or IPDA), 2,2,4- and 2,4,4-trimethylhexamethylenediamine (TMD), 1,3-xylylenediamine, 1,3-bis(aminomethyl)cyclohexane, bis(4-aminocyclohexyl)methane, bis(4-amino-3-methylcyclohexyl)methane, 3(4),8(9)-bis(aminomethyl)tricyclo[5.2.1.0²,⁶]decane, 1,2-, 1,3- and 1,4-diaminocyclohexane, 1,4-diamino-2,2,6-trimethylcyclohexane, 3,6-dioxaoctane-1,8-diamine, 4,7-dioxadecane-1,10-diamine, 4-aminomethyl-1,8-octanediamine, polyoxyalkylenepolyamines having two or three amino groups, and mixtures thereof.

11. An aldimine of the formula (IX)

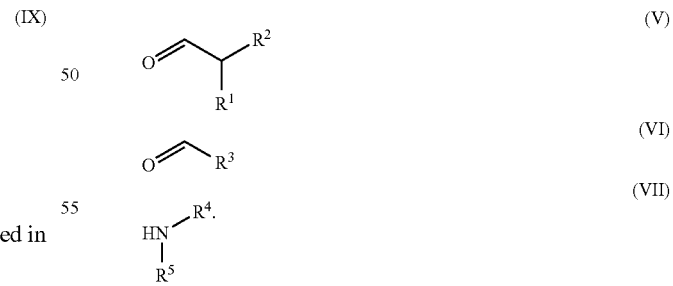

obtained from an aldimine of the formula (I) as claimed in claim 1 by protonation or alkylation, where
   R¹⁰ is a hydrogen atom or an alkyl, cycloalkyl or arylalkyl radical having 1 to 20 carbon atoms;
   X² is O or S or N—R¹¹ or N—R⁷; and
   R¹¹ is either
      a monovalent hydrocarbon radical which has 1 to 20 carbon atoms and optionally has at least one carboxylic ester, nitrile, nitro, phosphonic ester, sulfone or sulfonic ester group, or
      a substituent of the formula (IX')

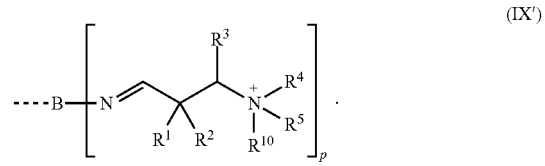

12. A process for preparing an aldimine of the formula (I) as described in claim 1, wherein an aldehyde ALD of the formula (IV) is reacted with an amine of the formula (III) in a condensation reaction $$[HX^a]_m\text{—}A\text{—}[NH_2]_n \quad (III)$$

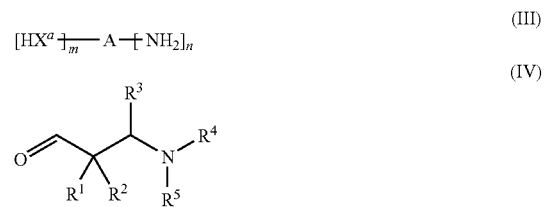

where
   $X^a$ is O or S or N—R⁶ᵃ or N—R⁷, and
   $R^{6a}$ is either
      a monovalent hydrocarbon radical which has 1 to 20 carbon atoms and optionally has at least one carboxylic ester, nitrile, nitro, phosphonic ester, sulfone or sulfonic ester group, or
      a substituent of the formula (III')

13. The process as claimed in claim 12, wherein the aldehyde ALD of the formula (IV) is obtained by reacting an aldehyde Y1 of the formula (V), an aldehyde Y2 of the formula (VI) and a secondary amine C of the formula (VII) with one another with elimination of water 14. The process for preparing an aldehyde ALD of the formula (IV) as claimed in claim 13, wherein
   the aldehyde Y1 of the formula (V) used is isobutyraldehyde,
   the aldehyde Y2 of the formula (VI) used is formaldehyde, and
   the amine C of the formula (VII) used is an amine selected from the group consisting of dimethylamine, diethylamine, diisopropylamine, dibutylamine, diisobutylamine, N-methylcyclohexylamine, N-methylbenzylamine, N-isopropylbenzylamine, N-tert-butylbenzylamine, dibenzylamine, pyrrolidine, piperidine, morpholine and 2,6-dimethylmorpholine.

15. A curable composition comprising at least one aldimine as claimed in claim 1, and at least one polyisocyanate.

16. A cured composition obtained by the reaction of a curable composition as claimed in claim 15 and water.

17. A method of treating an object comprising: combining the aldimine as claimed in claim 1, with adhesives, sealants, potting compositions, coatings, floor coverings, paints, coating materials, primers or foams.

18. A method of treating an object comprising providing a curable composition as claimed in claim 15 as a one- or two-component adhesive, sealant, potting composition, coating, floor covering, paint, coating material, primer or foam.

19. An article obtained by the method as claimed in claim 18.

20. The article as claimed in claim 19, wherein the article is
a built structure,
or an industrial good or a consumer good,
or a mode of transport,
or an installable component on a mode of transport,
or an article in the furniture, textile or packaging industry.

21. The aldamine of claim 1, wherein R3 has from 1 to 12 carbon atoms.

22. The aldamine of claim 1, wherein $R^7$ together with A is an (n+2)-valent hydrocarbon radical which has 3 to 20 carbon atoms and contains at least one heteroatom in the form of ether oxygen or tertiary amine nitrogen.

23. The aldimine of claim 3, wherein $A^1$ contains at least one heteroatom in the form of ether oxygen or tertiary amine nitrogen.

24. An aldimine of the formula (I) as claimed in claim 1, wherein $R^4$ and $R^5$ are together—including the nitrogen atom—a pyrrolidine, piperidine, morpholine, or N-alkylpiperazine ring, which ring is optionally substituted.

25. A cured composition obtained by the reaction of a curable composition as claimed in claim 15 and air humidity.

26. The article as claimed in claim 19, wherein the article is a built structure in construction or civil engineering, a window, a domestic appliance, an automobile, a bus, a truck, a train, or a ship.

\* \* \* \* \*